(12) United States Patent
Rothstein et al.

(10) Patent No.: US 11,612,608 B2
(45) Date of Patent: *Mar. 28, 2023

(54) METHODS OF TREATING ORAL MUCOSITIS

(71) Applicant: Galera Labs, LLC, Creve Coeur, MO (US)

(72) Inventors: David M. Rothstein, Lexington, MA (US); Chris Murphy, Upton, MA (US); Vivien Wong, Scarsdale, NY (US); Glenn Kazo, Lexington, MA (US)

(73) Assignee: galera labs, llc, Creve Coeur, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/802,916

(22) Filed: Feb. 27, 2020

(65) Prior Publication Data

US 2020/0215077 A1 Jul. 9, 2020

Related U.S. Application Data

(63) Continuation of application No. 15/841,586, filed on Dec. 14, 2017, now Pat. No. 10,610,533, which is a continuation of application No. 11/871,848, filed on Oct. 12, 2007, now Pat. No. 9,855,279.

(60) Provisional application No. 60/829,291, filed on Oct. 12, 2006.

(51) Int. Cl.
*A61K 31/555* (2006.01)

(52) U.S. Cl.
CPC .................. *A61K 31/555* (2013.01)

(58) Field of Classification Search
CPC .................................................... A61K 31/555
See application file for complete search history.

(56) References Cited

U.S. PATENT DOCUMENTS

| | | | |
|---|---|---|---|
| 3,930,867 A | 1/1976 | Bigelow | |
| 4,001,212 A | 1/1977 | Richman | |
| 4,702,998 A | 10/1987 | Tanaka et al. | |
| 5,096,724 A | 3/1992 | Zenner et al. | |
| 5,610,293 A | 3/1997 | Riley et al. | |
| 5,637,578 A | 6/1997 | Riley et al. | |
| 5,874,421 A | 2/1999 | Riley et al. | |
| 5,976,498 A | 11/1999 | Newumann et al. | |
| 6,040,330 A | 3/2000 | Hausheer et al. | |
| 6,084,093 A | 7/2000 | Riley et al. | |
| 6,177,419 B1 | 1/2001 | Campbell et al. | |
| 6,180,620 B1 | 1/2001 | Salvemini | |
| 6,204,259 B1 | 3/2001 | Riley et al. | |
| 6,214,817 B1 | 4/2001 | Riley et al. | |
| 6,245,758 B1 | 6/2001 | Stern et al. | |
| 6,395,725 B1 | 5/2002 | Salvemini | |
| 6,525,041 B1 | 2/2003 | Neumann et al. | |
| 6,781,231 B2 | 8/2004 | Minervini | |
| 6,916,799 B2 | 7/2005 | Fridovich et al. | |
| 7,102,214 B1 | 9/2006 | Miks et al. | |
| 7,166,910 B2 | 1/2007 | Minervini | |
| 7,242,089 B2 | 7/2007 | Minervini | |
| 7,407,645 B2 | 8/2008 | Neumann et al. | |
| 7,445,641 B1 | 11/2008 | Ornberg et al. | |
| 7,981,421 B2 | 7/2011 | Zhou et al. | |
| 8,263,568 B2 | 9/2012 | Slomczynska et al. | |
| 8,444,856 B2 | 5/2013 | Slomczynska et al. | |
| 8,808,545 B2 | 8/2014 | Slomczynska et al. | |
| 9,149,483 B2 | 10/2015 | Keene et al. | |
| 9,642,861 B2 | 5/2017 | Rothstein et al. | |
| 9,738,669 B2 | 8/2017 | Keene et al. | |
| 9,738,670 B2 | 8/2017 | Keene et al. | |
| 9,855,279 B2 | 1/2018 | Rothstein et al. | |
| 10,137,133 B2 | 11/2018 | Keene et al. | |
| 10,493,081 B2 | 12/2019 | Keene et al. | |
| 10,597,415 B2 | 3/2020 | Keene et al. | |
| 11,066,433 B2 | 4/2021 | Keene et al. | |
| 11,219,614 B2 | 1/2022 | Beardsley et al. | |
| 11,246,950 B2 | 2/2022 | Beardsley et al. | |
| 2002/0072512 A1 | 6/2002 | Salvemini | |
| 2002/0128248 A1 | 9/2002 | Salvemini | |
| 2003/0050297 A1 | 3/2003 | Crapo | |
| 2004/0132706 A1 | 7/2004 | Salvemini | |
| 2004/0219138 A1 | 11/2004 | Salvemini | |
| 2005/0101581 A1 | 5/2005 | Reading et al. | |
| 2005/0171198 A1 | 8/2005 | Salvemini | |
| 2005/0175580 A1 | 8/2005 | Salvemini | |
| 2005/0222250 A1 | 10/2005 | Rezvani | |
| 2006/0081994 A1 | 4/2006 | Craig et al. | |
| 2006/0089710 A1 | 4/2006 | Ornberg et al. | |

(Continued)

FOREIGN PATENT DOCUMENTS

| | | |
|---|---|---|
| CN | 1215919 | 5/1999 |
| CN | 2870352 | 2/2007 |

(Continued)

OTHER PUBLICATIONS

Shadad et al. World J Gastroenterol. Jan. 14, 2013; 19(2): 185-198. (Year: 2013).*
Yu et al. Transl Cancer Res. Oct. 1, 2013; 2(5): 384-396. (Year: 2013).*
Riley et al., Toward the rational design of superoxide dismutase mimics: mechanistic studies for the elucidation of substituent effects on the catalytic activity of macrocyclic manganese(II) complexes, JACS, 1997, 119(28): 6522-6528.
Salvemini et al., A nonpeptidyl mimic of superoxide dismutase with therapeutic activity in rats, Science, 1999, 286: 304-306 1999.

(Continued)

*Primary Examiner* — Jeffrey S Lundgren
*Assistant Examiner* — Chris E Simmons
(74) *Attorney, Agent, or Firm* — Bryan Cave Leighton Paisner LLP

(57) ABSTRACT

Methods and kits for treating oral mucositis are disclosed. The treatment comprises administering to a patient in need thereof a Reactive Oxygen Species scavenger in a pharmaceutically acceptable formulation.

14 Claims, 12 Drawing Sheets

(56) References Cited

U.S. PATENT DOCUMENTS

| | | |
|---|---|---|
| 2006/0140953 A1 | 6/2006 | Newell et al. |
| 2006/0199792 A1 | 9/2006 | Groves et al. |
| 2006/0223808 A1 | 10/2006 | Chackalamannil et al. |
| 2007/0148154 A1 | 6/2007 | Weill et al. |
| 2008/0161324 A1 | 7/2008 | Johansen et al. |
| 2008/0166000 A1 | 7/2008 | Hsiao |
| 2008/0269185 A1 | 10/2008 | Rothstein et al. |
| 2008/0318917 A1 | 12/2008 | Salvemini et al. |
| 2009/0131377 A1 | 5/2009 | Salvemini |
| 2009/0221622 A1 | 9/2009 | Teja et al. |
| 2009/0257979 A1 | 10/2009 | Beigelman et al. |
| 2010/0304415 A1 | 12/2010 | Slomczynska et al. |
| 2011/0136756 A1 | 6/2011 | Keene et al. |
| 2013/0079317 A1 | 3/2013 | Keene et al. |
| 2014/0142065 A1 | 5/2014 | Che et al. |
| 2017/0044193 A1 | 2/2017 | Keene et al. |
| 2018/0237462 A1 | 8/2018 | Keene et al. |
| 2019/0151331 A1 | 5/2019 | Beardsley et al. |
| 2019/0209524 A1 | 7/2019 | Beardsley et al. |
| 2020/0215077 A1 | 7/2020 | Rothstein et al. |
| 2021/0338686 A1 | 11/2021 | Keene et al. |
| 2021/0347796 A1 | 11/2021 | Keene et al. |
| 2021/0361701 A1 | 11/2021 | Keene et al. |
| 2022/0088030 A1 | 3/2022 | Keene et al. |
| 2022/0118119 A1 | 4/2022 | Beardsley et al. |

FOREIGN PATENT DOCUMENTS

| | | |
|---|---|---|
| CN | 103906756 | 7/2014 |
| EA | 010834 | 12/2008 |
| EP | 0524161 | 1/1993 |
| EP | 0598753 | 3/1998 |
| EP | 2760874 | 8/2014 |
| EP | 3388082 | 10/2018 |
| JP | H06509566 | 10/1994 |
| JP | 1996040941 | 2/1996 |
| JP | 2002506445 | 2/2002 |
| JP | 2002534382 | 10/2002 |
| JP | 2003509423 | 3/2003 |
| JP | 2004507487 | 3/2004 |
| JP | 2004517113 | 6/2004 |
| JP | 2011513333 | 4/2011 |
| JP | 2011516610 | 5/2011 |
| JP | 2014526562 | 10/2014 |
| RU | 2313368 | 9/2011 |
| WO | 199110645 | 7/1991 |
| WO | 1993002090 | 2/1993 |
| WO | 1994015925 | 7/1994 |
| WO | 95028968 | 11/1995 |
| WO | 1996039396 | 12/1996 |
| WO | 97006830 | 2/1997 |
| WO | 98058636 | 12/1998 |
| WO | 00072893 | 12/2000 |
| WO | 01019823 | 3/2001 |
| WO | 200158458 | 8/2001 |
| WO | 02053142 | 7/2002 |
| WO | 2002058686 | 8/2002 |
| WO | 2002071054 | 9/2002 |
| WO | 2002100395 | 12/2002 |
| WO | 2003024434 | 3/2003 |
| WO | 2005042718 | 5/2005 |
| WO | 2006078713 | 7/2006 |
| WO | 2006083508 | 8/2006 |
| WO | 2007139897 | 12/2007 |
| WO | 2008027547 | 3/2008 |
| WO | 2008045559 | 4/2008 |
| WO | 2009111294 | 9/2009 |
| WO | 2009134616 | 11/2009 |
| WO | 2009143454 | 11/2009 |
| WO | 2011113019 | 9/2011 |
| WO | 2013048965 | 4/2013 |
| WO | 2017027728 | 2/2017 |
| WO | 2017192740 | 11/2017 |
| WO | 2018191676 | 10/2018 |

OTHER PUBLICATIONS

Sishc et al., The radioprotector GC4419 ameliorates radiation induced lung fibrosis while enhancing the response of non-small cell lung cancer tumors to high dose per fraction radiation exposures, American Association of Cancer Research, 1 pg. 2018.

Sichc et al. The superoxide dismutase mimetic GC4419 enhances tumor killing when combined with stereotactic ablative radition, BioRxiv Mar. 11, 2020.

Zhu et al. Lysine 68 acetylation directs MnSOD as a tetrameric detoxification complex versus a monomeric tumor promoter. Nature Communications Jun. 3, 2019.

European Patent Office, Extended European Search Report for 20168046.96, 16 pages dated Oct. 16, 2020.

Jiang et al., Role of IL-2 in cancer immunotherapy, Oncoimmunology, 5(6);E1163462 Apr. 25, 2016.

Lasry et al., Inflammatory networks underlying colorectal cancer, Nature Immunology, 17(3):230-240 Feb. 16, 2016.

Mikirova et al., Effect of high-dose intravenous vitamin C on inflammation in cancer patients, Journal of Translational Medicine, 10(189): 2 pages 2012.

Riley et al., Manganese Macrocyclic Ligand Complexes as Mimics of Superoxide Dismutase, J. Am. Chem. Soc. 116:387-388 1994.

Pannala et al., Mechanistic Characterization of the Thioredoxin System in the Removal of Hydrogen Peroxide, Free Radic Biol Med., 78:42-55 2015.

Kelso et al., A Mitochondria-Targeted Macrocyclic Mn(II) Superoxide Dismutase Mimetic, Chemistry & Biology, 19:1237-1246 2012.

European Patent Office, Extended European Search Report issued for 18785213.2, 16 pages dated Feb. 8, 2021.

Wagner, B. A., et al., Myeloperoxidase is involved in $H_2O_2$-induced apoptosis of HL-60 human leukemia cells, J. Biol. Chem, 2000, 272(29), 22461-9.

Chen, Q., et al., Pharmacologic ascorbic acid concentrations selectively kill cancer cells: action as a pro-drug to deliver hydrogen peroxide to tissues, PNAS, 2005, 102(38), 13604-9.

Rodriguez, et al., Mitochondrial or cytosolic catalase reverses the MnSOD-dependent inhibition of proliferation by enhancing respiratory chain activity, net ATP production, and decreasing the steady state levels of $H_2O_2$, Free Rad. Bio. & Med.

Alexandre, J., et al., Novel Action of Paclitaxel against Cancer Cells: Bystander Effect Mediated by Reactive Oxygen Species, Cancer Research, 2007, 67(8), 3512-3517.

Muscoli, C., et al., On the selectivity of superoxide dismutase mimetics and its importance in pharmacological studies, British Journal of Pharmacology, 2003, 140(3), 445-460.

Sawyer, D. T. et al., How super is superoxide?, Acc. Chem. Res., 1981, 14, 393-400.

Li, S., et al., The Role of Cellular Glutathione Peroxidase Redox Regulation in the Suppression of Tumor Cell Growth by Manganese Superoxide Dismutase, Cancer Res., 2000, 60(14), 3927-3939.

Buettner, G. R., et al., A New Paradigm: Manganese Superoxide Dismutase Influences the Production of $H_2O_2$ in Cells and Thereby Their Biological State, Free Radical Biology and Medicine, 2006, 41(8), 1338-50.

Day, B. J., Catalase and glutathione peroxidase mimics, Biochem Pharmacol, 2009, 77(3), 285-296.

Day, B. J. et al., Manganic Porphyrins Possess Catalase Activity and Protect Endothelial Cells against Hydrogen Peroxide-Mediated Injury, Arch. Biochem. & Biophysics, 1997, 347(2), 256-262.

Oberley, L. W., Mechanism of the tumor suppressive effect of MnSOD overexpression, Biomedicine & Pharmacotherapy, 2005, 59, 143-48 Mar. 19, 2005.

Rocklage et al., Manganese(II) N ,N'-Dipyridoxylethylenediamine-N,N'-diacetate 5,5'- Bis(phosphate). Synthesis and Characterization of a Paramagnetic Chelate for Magnetic Resonance Imaging Enhancement, Inorg. Chem., 1989, 28, 477-485 Sep. 29, 1988.

European Patent Office, Extended Search Report issued for 12835035.2, dated Mar. 9, 2015.

Masini et al., Prevention of antigen-induced early obstruction reaction by inhaled M40419 in actively sensitized guinea-pigs, American Journal of Respiratory and Critical Case Medicine, American Lung Associations, New York, NY, Jan. 1, 2002.

(56) References Cited

OTHER PUBLICATIONS

McCarthy, A., Metaphore Pharmaceuticals, Chemistry & Biology, 2003, 10(12): 1139-1140.
MacArthur et al., Modulation of serum cytokine levels by a novel superoxide dismutase mimetic, M40401, in an *Escherichia coli* model of septic shock: Correlation with preserved circulating catecholamines, Crit. Care Med., 2003, 31(1): 237245.
Aston et al., Computer-Aided Design (CAD) of Mn(II) Complexes: Superoxide Dismutase Mimetics with Catalytic Activity Exceeding the Native Enzyme, Inorg. Chem., 2001, 40: 1779-1789.
Salvemini et al., Nonpeptidyl mimetics of superoxide dismutase in clinical therapies for diseases, Cell and Mol Life Sci, 2000, 57: 1489-1492.
MacArthur et al., Inactivation of catecholamines by superoxide gives new insights on the pathogenesis of septic shock, PNAS, 2000, 97(17): 9753-9758.
Riley, P.A., Free radicals in biology: oxidative stress and the effects of ionizing radiation, Int. J. Radiat. Biol, 1994, 65 (1): 27-33.
Shimizu et al., Neuroprotection against hypoxia-ischemia in neonatal rat brain by novel superoxide dismutase mimetics, Neuroscience Letters, 2003, 346: 41-44.
Tuder et al., Oxidative Stress and Apoptosis Interact and Cause Emphysema Due to Vascular Endothelial Growth Factor Receptor Blockade, Am. J. Respir. Cell Mol. Biol., 2003, 29: 88-97.
Fike et al., Reactive oxygen species from NADPH oxidase contribute to altered pulmonary vascular responses in piglets with chronic hypoxia-induced pulmonary hypertension, 2008, 295(5): L881-L888.
Batinic-Haberle et al., The ortho effect makes manganese(III) meso-tetrakis(N-methylpyridinium-2-yl)porphyrin a powerful and potentially useful superoxide dismutase mimic, J Biol Chem, 1998, 273: 24521-24528.
Batinic-Haberle et al., Pure MnTBAP selectively scavenges peroxynitrite over superoxide: , Free Radic Biol Med, 2009, 46:192-201.
Day et al., Metalloporphyrins are potent inhibitors of lipid peroxidation, Free Radic Biol Med, 1999, 26: 730-736.
Day et al., A metalloporphyrin superoxide dismutase mimetic protects against paraquat-induced endothelial cell injury, In vitro, J Pharmacol Exp Ther, 1995, 275:1227-1232.
Ferrer-Sueta et al., Reactions of Manganese Porphyrins with Peroxynitrite and Carbonate Radical Anion, J Biol Chem, 2003, 278: 27432-27438.
Kachadourian et al., Flavin-dependent antioxidant properties of a new series of meso-N,N'-dialkyl-imidazolium substituted manganese(III) porphyrins, Biochem Pharmacol, 2004, 67:77-85.
Szabo et al., Evaluation of the relative contribution of nitric oxide and peroxynitrite to the suppression of mitochondrial respiration in immunostimulated macrophages using a manganese, FEBS Letters, 1996, 381:82-86.
Murphy et al., Efficacy of Superoxide Dismutase Mimetic M40403 in Attenuating Radiation-Induced Oral Mucositis in Hamsters, Clin Cancer Res, 2008, 14(13): 4292-4297.
Salvemini et al., A nonpeptidyl mimic of superoxide dismutase with therapeutic activity in rats, Science, 1999, 286: 304-306.
Thompson et al., The manganese superoxide dismutase mimetic, M40403, protects adult mice from lethal total body irradiation, Free Radical Research, 2010; 44(5): 529-540.
Patent Cooperation Treaty, International Search Report issued for PCT/US2012/056921 dated Feb. 22, 2013, 5 pages.
Simic et al., Oxygen radicals in biology and medicine, Basic Life Sciences, 1988, vol. 49, Plenum Press, New York and London.
Weiss et al., Catalytic Efficacies of agents that dismutate superoxide, 1991, J. Cell, Biochem, Suppl. 15C, 216 Abstract C110.
Petkau, Scientific basis for the clinical use of superoxide dismutase, 1986, Cancer Treat. Rev. 13, 17.
McCord, Superoxide dismutase: Rationale for use in ruperfusion injury and inflammation, 1986, J. Free Radicals Biol. Med, 2, 307.
Bannister et al., Aspects of the structure, function, and applications of superoxide dismutase, 1987, Crit. Rev. Biochem., 22, 111.

Gryglewski et al., Superoxide anion is involved in the breakdown of endothelium-derived vascular relaxing factor, 1986, Nature, 320, 454-456.
Palmer et al., Nitric oxide release accounts for the biological activity of endothelium derived relaxing factor, 1987, Nature, 327, 523-526.
Samlowski et al., A nonpeptidyl mimic of superoxide dismutase, M40403, inhibits does-limiting hyptension associated with interleukin-2 and increases its antitumor effects, 2003, Nature Medicine, 9, 750-755.
Riley et al., Structure-activity studies and the design of synthetic superoxide dismutase (SOD) mimetics as therapeutics, 2006, Advances in Inorganic Chemistry, 59, 233-263.
Riley et al., Synthesis, characterization, and stability of manganese(II) C-Substituted 1, 4, 7, 10, 12-Pentaazacyclopentadecane complexes exhibity superoxide dismutase activity, J. Inorg. Chem. 1996, 35: 5213-5231.
Salvemini et al., M40403: Superoxied dismutase mimic, Drugs of the Future, 2000, 25(10): 1027-1033.
Salvemini et al., SOD Mimetics are coming of age, Nature Reviews, 2002, 1: 367-374.
Aykin-Burns et al., Increased levels of superoxide and H2O2 mediate the differential susceptibility of cancer cells versus normal cells to glucose deprivation, Biochem J., 2009, 418: 29-37 2009.
Fretland et al., Superoxide Dismutase (SOD) Modulates Acetic Acid-Induced Colitis in Rodents, Gastroenterology, 1991, 100: A581 1991.
Newton et al., Synthesis and characterization of the Mn(II) complexof [15]aneN.sub.5, J. Coord. Chem., 1988, 19: 265-277 1988.
Bradshaw et al., A simple crab-like cyclization procedure to prepare polyaza-crowns and cyclams with one or two unsubstitute macroring Nitrogen atoms or with a Hydroxy group, J. Heterocyclic Chem, 1989, 26: 1431-1435 1989.
Krakowiak et al., Preparation of Triaza-, Tetraaza- and Peraza-Crown Compounds containing Aminoalkyl Side Groups or Unsubstituted Rin Nitrogen Atoms, J. Org. Chem, 1990, 55(10): 3364-3368 1990.
Riley et al., Stopped-flow Kinetic Analysis for Monitoring superoxide decay in aqueous systems, Analystical Biochemistry, 1991, 196: 344-349 1991.
Weiss et al., Catalytic efficacies of agents that dismutate superoxide, J. Cell. Biochem., 1991, Supplement 15C: 216 1991.
Eldor et al., Perturbation of endothelial functions by ionizing irradiation: effects on prostaglandins, chemoattractants and mitogens, Semin Thromb Hemost, 1989, 15(2): 215-225 1989.
Escribano et al., Aerosol Orgotein (Ontosein) for the Prevention of Radiotherapy-Induced Adverse Effects in Head and Neck Cancer Patients: A feasibility study, Neoplasma, 2002, 49(3): 201-209 2002.
Gridley et al., Chapter 16, Therapeutic Application of Superoxide Dismutase (SOD) (Salvemini and Cuzzocrea, eds.), 2004, 1-20 2004.
Guo et al., Prevention of Radiation-Induced Oral Cavity Mucositis by Plasmid/Liposome Delivery of the Human Manganese Superoxide Dismutase (SOD2) Transgene, Radiat. Red., 2003, 159(3): 361-370 2003.
Knox, et al., Chemotherapy-induced oral mucositis. Prevention and Management, Drugs Aging, 2000, 17(4): 257-267 2000.
Leussink et al., Pathways of Proximal Tubular Cell Death in Bismuth Nephrotoxicity, Toxicol. Appl. Pharmacol., 2002, 180(2): 100-109 2002.
Orrell, R.W., AEOL-10150 (Aeolus), Current Opinion Investig. Drugs, 2006, 7(1): 70-80 2006.
Peterson, D. E. Research advances in oral mucositis. Current Opinion Oncol., 1999, 11(4): 261-266 1999.
Plevova, P. Prevention and treatment of chemotherapy- and radiotherapy-induced oral mucositis: a review. Oral Oncol. 1999; 35(5): 453-470 1999.
Salvemini et al., Amelioration of Joint Disease in a Rat Model of Collagen-Induced Arthritis by M40403, a Superoxide Dismutase Mimetic, Arthritis & Rheumatism, 2001, 44: 2909-2921 2001.
Slikkerveer et al., Pharmacokinetics and Toxicity of Bismuth Compounds, Med. Toxicol. Adverse Drug Exp, 1989, 4(5): 303-323 1989.

(56) References Cited

OTHER PUBLICATIONS

Sonis, Oral Mucositis in Cancer Therapy, Support. Oncol., 2004, 2 (supple.3): 3-8 2004.
Sonis et al., Mitigating Effects of Interleukin 11 on Consecutive Courses of 5-Fiuorouracil-Induced Ulcerative Mucositis in Hamsters, Cytokine, 1997, 9(8): 605-612 1997.
Ahmad et al., Mitochondrial $O_2$ and $H_2O_2$ Mediate Glucose Deprivation-induced Cytotoxicity and Oxidative Stress in Human Cancer Cells, J. Bio. Chem., 2005, 280(6): 4254-4263 2005.
Sonis et al., Transforming Growth Factor-B3 Mediated Modulation of Cell Cycling and Attenuation of 5-Fiuorouracil Induced Oral Mucositis, Oral Oncol., 1997, 33(1): 47-54 1997.
Sonis et al., Defining Mechanisms of action of interleukin-11 on the progression of radiation-induced oral mucositis in hamsters, Oral Oncology, 2000, 36(4): 373-381 2000.
Cuzzocrea et al., C. Tempol, a membrane-permeable radical scavenger, reduces dinitrobenzene sulfonic acid-induced colitis, Eur J Pharmacol., 2000, 406:127-137 2001.
Goodman & Gilman's The Pharmacological Basis of Therapeutics, 10th Edition, McGraw Hill, 1996 1996.
Suenderhauf et al., A Physiologically Based Pharmacokinetic Model of the Minipig: Data Compilation and Model Implementation, Pharm. Res., 2013, 30(1): 1-15 2013.
Cuzzocrea et al., Protective effects of M40401, a selective superoxide dismutase mimetic, on zymosan-induced nonseptic shock, Crit. Care Med., 2004, 21(1): 157-167 2004.
Cuzzocrea et al., Reduction in the development of Cerulein-induced acute pancreatitis by treatment with M40401, a new selective superoxide dismutase mimetic, Shock, 2004, 22(3): 254-261 2004.
Anderson, C., Phase 1 Trial of Superoxide Dismutase (SOD) Mimetic GC4419 to Reduce Chemoradiotherapy (CRT)-Induced Mucositis (OM) in Patients (pts) with Mouth or Oropharyngeal Carcinoma (OCC), Oral Mucositis Research Workshop, MASCC/ISOO Annual Meeting on Supportive Care in Cancer, Copenhagen, Denmark (Jun. 25, 2015) 2015.
Cotton et al., Advanced Inorganic Chemistry, Chapter 5, "Coordination Compounds", 2nd revised edn., Interscience Publishers, 1966, 139 1966.
Cotton et al., Advanced Inorganic Chemistry, Chapter 2, "Coordination Compounds", 2nd revised edn., Interscience Publishers, 1966, 35-36, 45-49 1966.
Wang et al., Evidence of d-phenylglycine as delivering tool for improving I-dopa absorption, J. Biomed. Sci., 2010, 17: 71-79 2010.
Wikipedia, Cefalexin, retrieved Nov. 2, 2016, from en.wikipedia.org/wiki/Cefalexin, 6 pages 2016.
Hironaka et al., Quantitative Evaluation of PEPT1 Contribution to Oral Absorption of Cephalexin in Rats, Pharm. Res., 2009, 26(1): 40-50 2009.
Knütter et al., Transport of Angiotensin-Converting Enzyme Inhibitors by H+/Peptide Transporters Revisited, J. Pharma. Exp. Thera., 2008, 327(2): 432-441 2008.
Patent Cooperation Treaty, International Search Report for PCT/US2016/046599, dated Nov. 17, 2016, 5 pages dated Nov. 17, 2016.
Park et al., Facility case volume and outcomes for intensity-modulated radiotherapy in head and neck cancer, Department of Therapeutic Radiology, Yale School of Medicine, 1 pg. Sep. 26, 2016.
Boero et al., Importance of Radiation Oncologist Experience Among Patients With Head-and-Neck Cancer Treated With Intensity-Modulated Radiation Therapy, Journal of Clinical Oncology, 2016, 34(7): 684-696 Mar. 1, 2015.
Ferreira et al., Effect of radiotherapy delay in overall treatment time on local control and survival in head and neck cancer: Review of the literature, Reports of Practical Oncology and Radiotherapy, 2015, 20: 328-339 May 24, 2015.
Anderson et al., Phase 1b Trial of Superoxide Dismutase Mimetic GC4419 to Reduce Chemoradiotherapy-induced Oral Mucositis in Patients with Oral Cavity or Oropharyngeal Carcinoma, Multidisciplinary Head and Neck Cancer Symposium, Scottsdale, Arizona, 17 pgs Feb. 18, 2016.
Hussan et al., A review on recent advances of enteric coating, Journal of Pharmacy, 2012, 2(6): 5-11 2012.
Strickley, R. G., Solubilizing Excipience in Oral and Injectable Formulations, Pharmaceutical Research, 2004, 21 (2): 201-230 2004.
Pardoll, D. M., The blockade of immune checkpoints in cancer immunotherapy, Nat Rev Cancer, 2012. 12(4): 252-264 Mar. 22, 2012.
Jin et al., Clinical Observation on Superoxide Dismutase in Respect of Resistance to Skin Damage Resulting from Radiation, Chinese Journal of Radiological Health, 1993, 2(3): 137 1993.
Masini et al., Reduction of antigen-induced respiratory abnormalities and airway inflammation in sensitized guinea pigs by a superoxide dismutase mimetic, Free Radical Biology & Medicine, 2005, 39: 520-531 2005.
Salvemini et al., Superoxide Dismutase Mimetics, Pulmonary Pharmocology & Therapeutics, 2002,15: 439-447 2002.
Weiss et al., Manganese-based Superoxide Dismutase Mimetics Inhibit Neutrophil Infiltration in Vivo, Journal of Biological Chemistry, 1996, 271(42): 26149-26156 1996.
Udipi et al., Modification of inflammatory response to implated biomedical materials in vivo by surface bound superoxide dismutase mimics, Journal of Biomedical Materials Research, 1999, 1-12 1999.
Cuzzocrea et al., Protective effects of M40403, a superoxide dismutase mimetic, in a rodent model of colitis, European Journal of Pharmacology, 2001, 432: 79-89 2001.
Salvemini et al., Protective effects of superoxied dismutase mimetic nd peroxynitrite decomposition catalyst in endotoxin-indueced intestinal damage, 1999, British Journal of Pharmacology, 127(3):685-692 1999.
European Patent Office, Extended European Search Report issued for App. No. 17166668.8, 11 pages Sep. 27, 2017.
Sindoni et al., Combination of immune checkpoint inhibitors and radiotherapy: Review of the literature, Critical Reviews in Oncology/Hematology, 2017, 113: 63-70 2017.
Patent Cooperation Treaty, International Search Report for PCT/US2017/049960, 5pgs. dated Feb. 21, 2019.
Fritz et al., Intravenous vitamin C and cancer: A systematic review, Integrative Cancer Therapies, 13(4): 280-300 2014.
McConnell et al., Ascorbate combination therapy: New tool in the anticancer toolbox?, Science Translational Medicine, 6(222): 1-3 2014.
Patent Cooperation Treaty, International Search Report for PCT/US2019/016071, 4pgs. dated May 14, 2019.
Mapuskar et al., Mitochondrial Superoxide Increases Age-Associated Susceptability of Human Dermal Fibroblasts to Radiation and Chemotherapy, Cancer Research, 77(18): 5054-5067 2017.
European Patent Office, Extended Search Report for EP App. 17847659.4, 12 pages dated Mar. 6, 2020.
Salvemini et al., Reply to "Role of manganese superoxide dismutase in cancer", Nature Medicine, 9(9): 1103-1103 Sep. 1, 2003.
Tovmasyan et al., Radiation-Mediated tumor growth inhibition is significantly enhanced with redox-active compounds that cycle with ascorbate, Antioxidants and Redox Signaling, 29(13): 1196-1214 Nov. 1, 2018.
Zhou et al., Experimental Study on Superoxide Dismutase for Prophylaxis and Treatment of Inflammatory Damage to Mouth Mucosa in Animals, West China Journal of Stomatology, 1996, 14(2) 1996.
Kasten et al., Potentiation of Nitric Oxide-Mediated Vascular Relaxation by SC52608, a Superoxide Dismustas Mimic, 1995.
Patent Cooperation Treaty, International Search Report for PCT/US2018/027588, 5 pages Aug. 27, 2018.
Park et al., Synthesis and SOD activity of manganese complexes of pentaaza macrocycles containing amino-and guanidino-auxiliary, Bulletin of the Korean Chemical Society, 32(10): 3787-3789 2011.
Patent Cooperation Treaty, International Search Report for PCT/US2018/018407, 6 pages dated Sep. 17, 2018.
Tabata et al., Ion-Pair Extraction of Metalloporphyrins into Acetonitrile for Determination of Copper(II), Anal. Chem., 68:758-762 1996.
Mazzucotelli, et al., Determination of trace amounts of Metalloprotein Species in Marine Mussel Samples by High Performance

(56) References Cited

OTHER PUBLICATIONS

Liquid Chromatography with Inductively Coupled Plasma Atomic Emission Spectrometric Detection, Analyst., 116: 605-608 1991.
Furuya et al., Determination of Pheophytinatoiron(III) Chlorides by Reverse Phase High Performance Liquid Chromatography, Analytical Sciences, 3: 353-357 1987.
Zhang et al., Quantitative determination of SC-68328 in dog plasma using flow injection and tandem mass spectroscopy, Journal of Mass Spectrometry, 35(3): 354-360 2000.
Sakai et al., Liquid-Chromatographic Separation and Determination of Coproporphyrins I & III in Urine, Clinical Chemistry, 29(2): 350-353 1983.
Riley, Functional Mimics of Supeoxide Dismutase Enzymes and Therapeutic Agents, Chem. Rev., 2572-2587 1999.
Berge et al., Pharmaceutical Salts, J. Pharm. Sci., 66: 1-19 1977.
European Patent Office, European Search Report issued for EP 10179542, 4 pages Aug. 5, 2011.
European Patent Office, Extended European Search Report for 16835928.9, publication 3334744, 10 pgs. Feb. 4, 2019.
Cornwell et al., Glyceryl monocaprylate/caprate as a moderate skin penetration enhancer, International Journal of Pharmaceutics, 171: 243-255 1998.
Eurasian Patent Office, Search Report for 201892510, 1 page dated May 28, 2019.
European Patent Office, Extended Search Report for EP App. 18215666.1, 12 pages dated Jul. 19, 2019.
Di Paolo et al., Reduced development of experimental periodontitis by treatment with M40403, a superoxide dismutase mimetic, European Journal of Pharmacology, 51: 151-157 2005.
McFadden et al., M40403, a superoxide dismutase mimetic, protects cochlear hair cells from gentamicin, but not cisplatin toxicity, Toxicology and Applied Pharmacology, 186: 46-54 2003.
European Patent Office, Extended Search Report for EP App. 17793268.8, 8 pages dated Nov. 29, 2019.
Fath et al., Enhancement of Carboplatin-Mediated Lung Cancer Cell Killing by Simultaneous Disruption of Glutathione and Thioredoxin Metabolism, Clinical Cancer Research, 17(19): 6206-6217 2011.
Jungwirth et al., Anticancer Activity of Metal Complexes: Involvement, Antioxidants & Redox Signaling, 15(4): 1085-1127 2011.
Cao et al., Mechanisms of ferroptosis, Cell. Mol. Life Sci., 2016, 11:2195-2209 2016.
Rodman III, et al., Enhancement of Radiation Response in Breast Cancer Stem Cells by Inhibition of Thioredoxin and Glutathione Dependent Metabolism, Radiat Res., 2016, 186(4): 385-395 2016.
Raj et al., Selective killing of cancer cells by a small molecule targeting the stress response to ROS, Nature, 475: 231-234 2016.
Samlowski et al., Evaluation of a Superoxide Dismutase Mimetic as an Adjunct to Interleukin 2 Based Cancer Therapy, Madame Curie Report, 230-249 2006.
Samlowski et al., A nonpeptidyl mimic of superoxide dismutase, M40403, inhibits dose-limiting hypotension associated with interleukin-2 and increases its antitumor effects. Nature Medicine, 9:750-755 2003.
Sishc et al., Superoxide dismutase mimetic GC4419 protects against radiation induced lung fibrosis, exhibits anti-tumor effects, and enhances radiation induced cell killing, 1 pg 2015.
Sishc et al, Superoxide dismutase mimetic GC4419 sensitizes non-small cell lung cancer tumors to high dose per fraction radiation and ameliorates radiation induced lung fibrosis, 1 pg 2016.
Scarbrough, P.M., Inhibitors of glucose and hydroperoxide metabolism potentiate 17AAG-induced cancer cell killing via metabolic oxidative stress, University of Iowa Theses and Dissertations 2011.
Sobhakumari et al., Susceptibility of Human Head and Neck Cancer Cells to Combined Inhibition of Glutathione and Thioredoxin Metabolism, PLOS, 7(10): e48175, 10 pgs 2012.
Elting et al., The Burdens of Cancer Therapy, Cancer, 98(7): 1531-1539 2003.
Epperly et al., Manganese Superoxide Dismutase-Plasmid/ Liposome (MnSOD-PL) Administration Protects Mice from Esophagitis Associated with Fractionated Radiation, Int. J. Cancer (Radiat. Oncol. Invest), 96: 221-231 2001.
Epperly et al., Intraoral Manganese Superoxide Dismutase-Plasmid/ Liposome (MnSOD-PL) Radioprotective Gene Therapy Decreases Ionizing Irradiation-induced Murine Mucosal Cell Cycling and Apoptosis, In Vivo, 18:401-410 2004.
Guo et al., Gene Transfer of Human Manganese Superoxide Dismutase Protects Small Intestinal Villi From Radiation Injury, J Gastrointest Surg., 7(2): 229-235 2003.
Lalla et al., Treatment of Mucositis, Including New Medications, Palliative and Supportive Care, 12(5): 348-354 2006.
Zhang et al. Thioredoxin reductase inhibitors: a patent review, Expert Opinion on Therapeutic Patents, 27(5): 547-556 2017.
Murakami, The Chemical Society of Japan, editions, Separation of Optical Isomer quarterly journal, chemical review No. 6, Scientific Societies Press, p. 212-213 (translation) 1989.
Anderson, et al. Two-Year Tumor Outcomes of Phase 2B, Randomized, Double-Blind Trial of Avasopasem Manganese (GC4419) Versus Placebo to Reduce Severe Oral Mucositis Due to Concurrent Radiation Therapy and Cisplatin for Head and Neck Cancer Published:Jun. 17, 2022DOI:https://doi.org/10.1016/j.ijrobp.2022. 06.063.
Anderson, et al. Phase IIb, Randomized, Double-Blind Trial of GC4419 Versus Placebo to Reduce Severe Oral Mucositis Due to Concurrent Radiotherapy and Cisplatin For Head and Neck Cancer, Journal of Clinical Oncology 37, No. 34 (Dec. 1, 2019) 3256-3265.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., vol. 100, Issue 2, p. 427-435, Feb. 1, 2018.
ASCO Abstract Effects of GC4419 (avasopasem manganese) on chronic kidney disease in head and neck cancer patients treated with radiation and cisplatin, American Society of Clinical Oncology, 2020 2 pages.
Mapuskar, et al. Mitochondrial Superoxide Dismutase in Cisplatin-Induced Kidney Injury, Antioxidants 2021, 10, 1329 16 pages.
O'Leary, et al. Loss of SOD3 (EcSOD) Expression Promotes an Aggressive Phenotype in Human Pancreatic Ductal Adenocarcinoma, Downloaded from www.clincancerres.aacrjournals.org on Jul. 17, 2020 pp. 1741-1751.
Sishc, et al. Avasopasem manganese synergizes with hypofractionated radiation to ablate tumors through the generation of hydrogen peroxide, Sci. Transl. Med. 13, May 12, 2021 pp. 1-13.
Sishc, et al. Avasopasem Manganese Protects Against Radiation Induced Oral Mucositis and Enhances the Response of Squomous Cell Carcinoma of the Head and Neck to Ionizing Radiation and Radioimmune Therapy, Astro, vol. 108, Issue 3, Suppl. S159, Nov. 1, 2020.
Sishc, et al. Abstract: The radioprotector GC4419 enhances the response of pancreatic ductal adenocarcinoma tumors to high dose per fraction radiation exposure, AACR PDAC Meeting 2019.
Steinbach, et al. Effects of GC4419 (Avasopasem Manganese) on Chronic Kidney Disease in Head and Neck Cancer Patients Treated with Radiation and Cisplatin, ASCO20 May 2020 1 pages.
Salvemini et al., Pharmacological manipulation of the in ammatory cascade by the superoxide dismutase mimetic, M40403, British Journal of Pharmacology, 2001, 132: 815-827 2001.
Laurent et al. Controlling Tumor Growth by Modulating Endogenous Production of Reactive Oxygen Species, Cancer Research, 65(3): 948-956 2005.
Tovmasyan et al., Anticancer therapeutic potential of Mn porphyrin/ ascorbate system, Free Radical Biology and Medicine, 89:1231-1247 2015.
Rawal et al., Manganoporphyrins Increase Ascorbate-Induced Cytotoxicity by Enhancing H2O2 Generation, Cancer Research, 73(16):5232-5241 2013.
Batinic-Haberle et al., An educational overview of the chemistry, biochemistry and therapeutic aspects of Mn porphyrins—From superoxide dismutation to H2O2-driven pathways, Redox Biology, 5:43-65 2015.

(56) References Cited

OTHER PUBLICATIONS

Marzano et al., Inhibition of thioredoxin reductase by auranofin induces apoptosis in cisplatin-resistant human ovarian cancer cells, Free Radical Biology & Medicine 42: 872-881 2007.
U.S. Department of Health and Human Services, Food and Drug Administration, Center for Drug Evaluation and Research (CDER), Guidance for Industry Estimating the Maximum Safe Starting Dose in Initial Clinical Trials for Therapeutics in Adult Healthy Volunteers, 30 pages 2005.
Qian et al., Advances in the study of effects of vitamin C on tumor prevention, Youjiang Medical Journal, 36(6): 741-743 2008.
Ghosh et al., A novel manganese complex, Mn-(II) N-(2-hydroxy acetophenone) glycinate overcomes multidrug-resistance in cancer, European Journal of Pharmaceutical Sciences, 49: 737-747 2013.
Serafim et al., Regulating mitochondrial respiration in cancer in: Kanner S. (eds) Tumor Metabolome Targeting and Drug Development, Cancer Drug Discovery and Development, 45 pages 2014.
Liu et al., Mechanisms of the CDK4/6 inhibitor palbociclib (PD 0332991) and its future application in cancer treatment (Review), Oncology Reports, 36: 901-911 2018.
Friend, D. R., Review article: Issues in oral administration of locally acting glucocorticosteroids for treatment of inflammatory bowl disease, Aliment Pharmacol Therapy, 12: 591-603 1198.
Anderson et al., Phase 1b/2a Trial of Superoxide (SO) Dismutase (SOD) Mimetic GC4419 to Reduce Chemoradiation Therapy-Induced Oral Mucositis (OM) in Patients With Oral Cavity or Oropharyngeal Carcinoma (OCC), Intl. J. Rad. Oncol., 2016, 94(4): 869-870 2016.
Kim et al., Antiproliferative effect of gold(I) compound auranofin through inhibition of STAT3 and telomerase activity in MDA-MB 231 human breast cancer cells, BMB Rep., 46(1): 59-64 2013.
Zou et al., Auranofin induces apoptosis by ROS-mediated ER stress and mitochondrial dysfunction and displayed synergistic lethality with piperlongumine in gastric cancer, Oncotarget, 6(34): 36505-36521 2015.
Mikirova, et al. "Effect of high-dose intravenous Vitamin C on inflammation in cancer patients," Journal of Translational Medicine 2012.
Declaration under 37 C.F.R. 1.132 of Dennis P. Riley, dated Mar. 7, 2014, and filed in U.S. Appl. No. 11/871,848, filed Mar. 3, 2014.
Declaration under 37 C.F.R. 1.132 of Douglas R. Spitz, dated Feb. 6, 2014, and filed in U.S. Appl. No. 11/871,848, filed Feb. 6, 2014.
Keene, J. L Declaration under 37 C.F.R. 1.132 May 14, 2014 May 14, 2014.
Mikirova, et al. CAS: 158, 290966, 2012 2012.
Alexandre, et al. "Improvement of the therapeutic index of anti-cancer drugs by the superoxide dismutase mimic mangafodipir," Journal of the National Cancer Institute, vol. 98, No. 4, Feb. 15, 2006, pp. 236-244 Feb. 15, 2006.
Belotte, et al. "Abstract B01: Superoxide dismutase significantly reversed the development of cisplatin resistance in epithelial ovarian cancer," Acquired Resistance, Feb. 13, 2015 pp. B01-B01 Feb. 13, 2015.
Karlsson, et al. "Calmangafodipir [Ca4Mn (DPDP) 5], mangafodipir (MnDPDP) and MnPLED with special reference to their SOD mimetic and therapeutic properties," Drug Discovery Today, vol. 20, No. 4, Apr. 1, 2015 Apr. 1, 2015.
Ahmed, et al. "Tempol, a Superoxide Dismutase Mimetic Agent, Ameliorates Cisplatin-Induced Nephrotoxicity through Alleviation of Mitochondrial Dysfunction in Mice," PLOS One, vol. 9, No. 10, Jan. 1, 2014 Jan. 1, 2014.
Wangila, et al. "Prevention of cisplatin-induced kidney epithelial cell apoptosis with a Cu superoxide dismutase-mimetic [copper 2^|^(3,5-ditertiarybutylsalicylate)"4(ethanol) "4], Toxicology In Vitro, Elsevier Science, vol. 20, No. 8 Dec. 1, 2006 pp. 1300-1312 Dec. 1, 2006.
Kobayashi, et al. "Enhancement of Anti-Cancer Activity of Cisdiaminedichloroplatinum by the Protein-Bound Polysaccharide of Coriolus Versicolor QUEL (PS-K) In Vitro," Cancer Biotherapy, vol. 9, No. 4 Jan. 1, 1994 pp. 351-358 Jan. 1, 1994.
Karlsson, et al. "First clinical expeirence with the magnetic resonance imaging contrast agent and superoxide dismutase mimetic mangafodipir as an adjunct in cancer chemotherapy-a translational study," Translational Oncology, Feb. 1, 2012 pp. 32-38 Feb. 1, 2012.
Karlsson, et al. "Superior therapeutic index of calmangafodipir in comparison to mangafodipir as a chemotherapy adjunct," Translational Oncology, Dec. 1, 2012 p. 492 Dec. 1, 2012.
Davis, et al. "Manganese Superoxide Dismutase Attenuates Cisplatin-Induced Renal Injury: Importance of Suproxide," Journal of the American Society of Nephrology, vol. 12, No. 12, Dec. 1, 2001 pp. 2683-2690 Dec. 1, 2001.
Mohanty, et al. "Abstract 2929: GC4419 enhances the response of non-small cell lung carcinoma cell lines to cisplatin and cisplatin plus radiation through a ROS-mediated pathway : Cancer Research," AACR Annual Meeting 2018, Jul. 1, 2018 pp. 1-4 Jul. 1, 2018.
Mapuskar, et al. "Mitochondrial Superoxide Dismutase in Cisplatin-Induced Kidney Injury," Antioxidants, vol. 10, No. 9, Aug. 24, 2021 p. 1329 Aug. 24, 2001.
European Patent Office, Extended European Search Report for 19747505.6 publication 3746085 21 pgs. Feb. 9, 2022 Feb. 9, 2022.
Galera Therapeutics, Inc., A Phase 1 Dose Escalation Study of GC4419 in Combination With Chemoradiation for Squamous Cell Cancer of the Head & Neck, NIH U.S. National Library of Medicine, ClinicalTrials.gov,, 8 pages 2013.
Dyck et al., Immune checkpoints and their inhibition in cancer and infectious diseases, European Journal of Immunology, 47: 765-779 2017.
Du et al., Glutathione and glutaredoxin act as a backup of human thioredoxin reductase 1 to reduce thioredoxin 1 preventing cell death by aurothioglucose, J. Biol Chem, 287(45), 38210-38219 2012.
Fan et al., Enhancement of auranofin-induced lung cancer cell apoptosis by selenocystine, a natural inhibitor of TrxR1 in vitro and in vivo, Cell Death & Disease, 5, e1191 2018.
Kurosawa et al., Cytotoxicity induced by inhibition of thioredoxin reductases via multiple signaling pathways: Role of cytosolic phospholipase A2alpha-dependent and -independent release of arachidonic acid, Journal of Cell Physiology, 219(3): 606-616 2009.
Li et al., Auranofin-mediated inhibition of PI3K/AKT/mTOR axis and anticancer activity in non-small cell lung cancer cells. Oncotarget, 7(3): 3548-3558 2016.

* cited by examiner

Figure 1. Study timeline.

FIG. 2

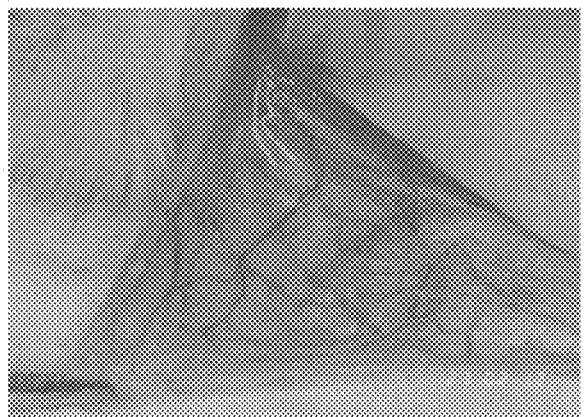

A. Score of 0. The pouch is completely healthy with no erythema or vasodilation.

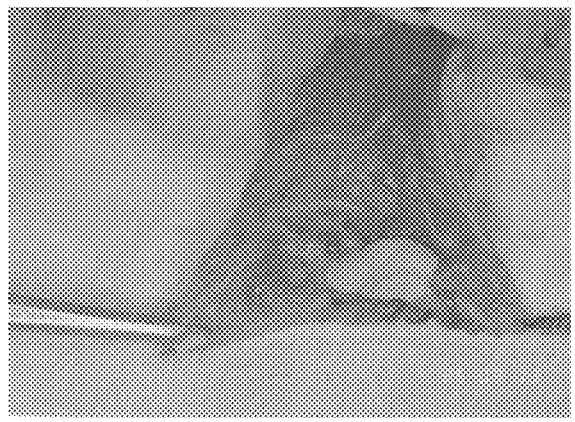

D. Score of 3. Formation of ulcer occupying ¼ or less of the pouch.

B. Score of 1. Light to severe erythema and vasodilation with no erosion of the mucosa.

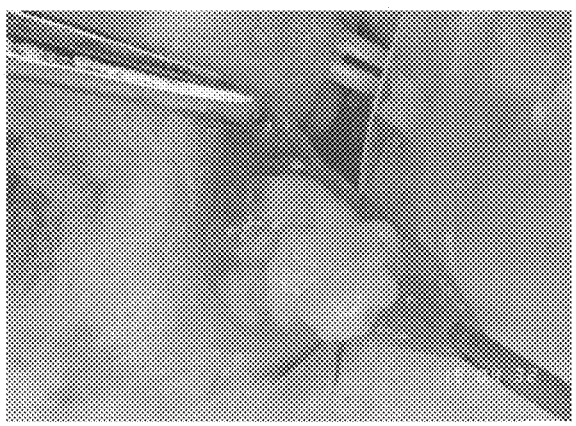

E. Score of 4. Total size of ulcer occupies ½ of the Pouch with loss of pliability.

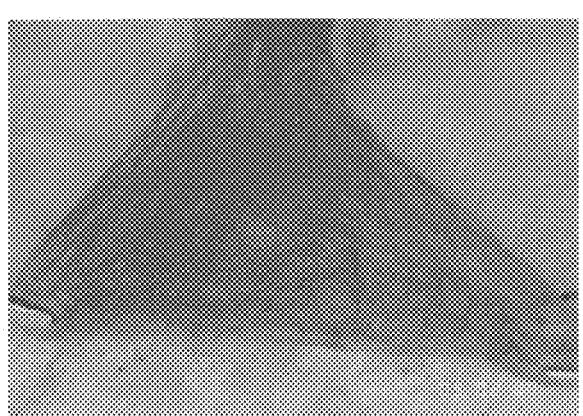

C. Score of 2. Severe erythema and vasodilation with erosion and decreased stippling of superficial mucosa leaving denuded areas.

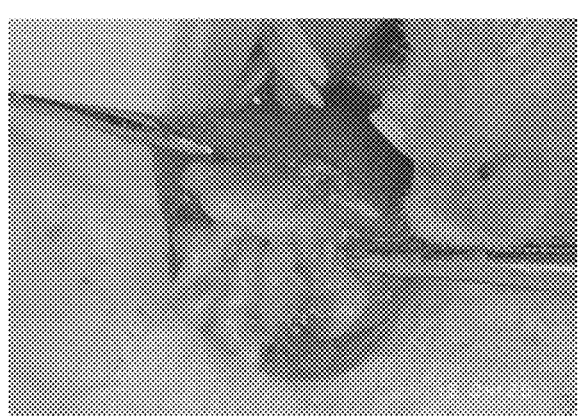

F. Score of 5. Ulceration to virtually all of the pouch. Pouch can only be partially everted.

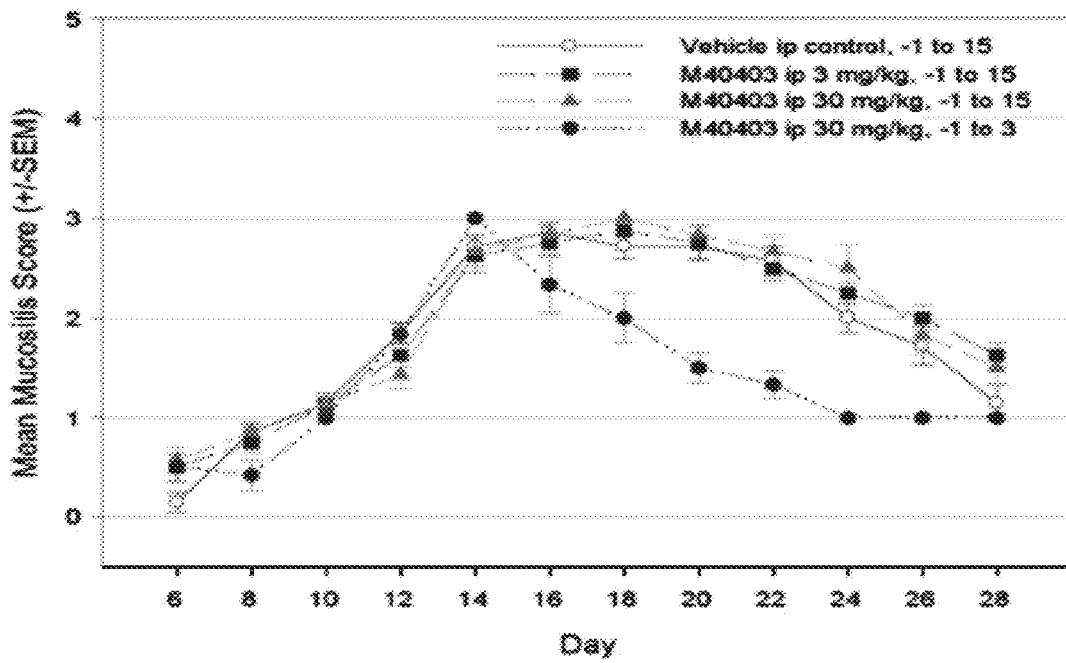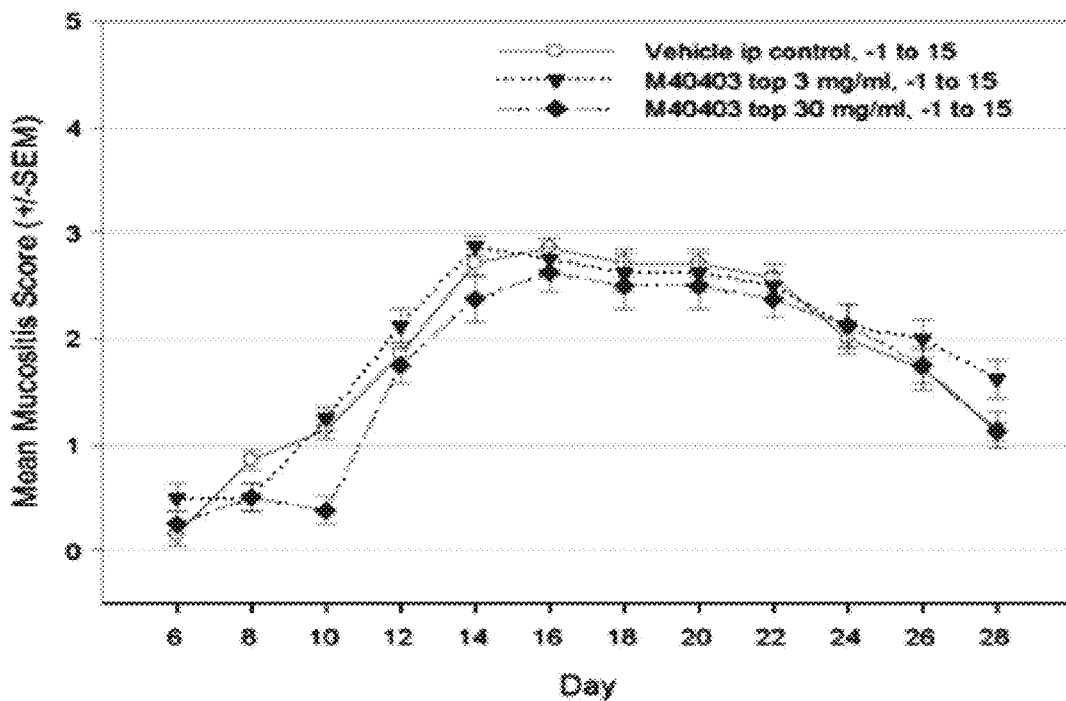
FIG. 5

FIG. 8

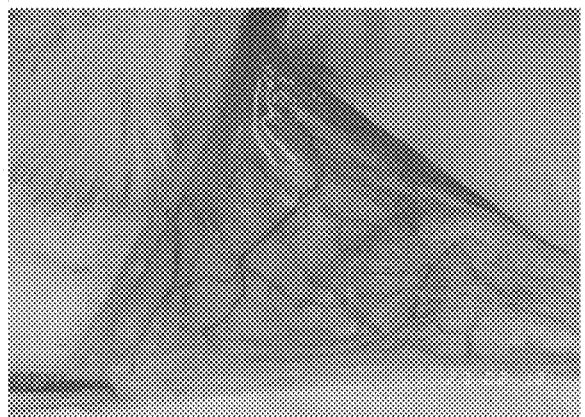

A. Score of 0. The pouch is completely healthy with no erythema or vasodilation.

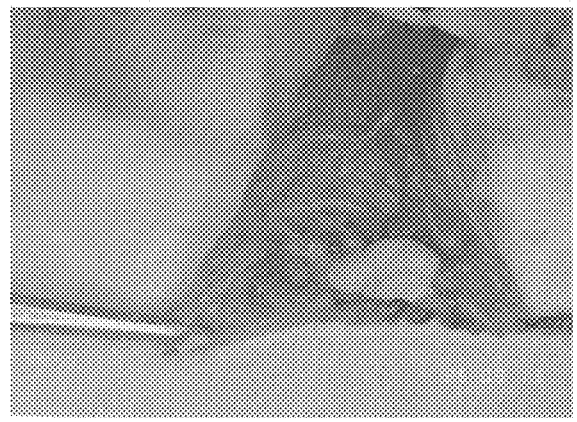

D. Score of 3. Formation of ulcer occupying ¼ or less of the pouch.

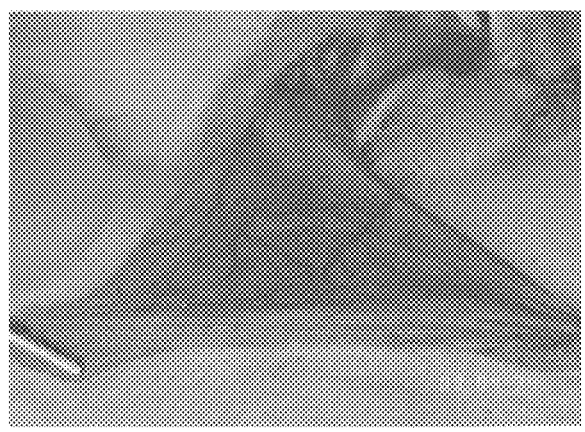

B. Score of 1. Light to severe erythema and vasodilation with no erosion of the mucosa.

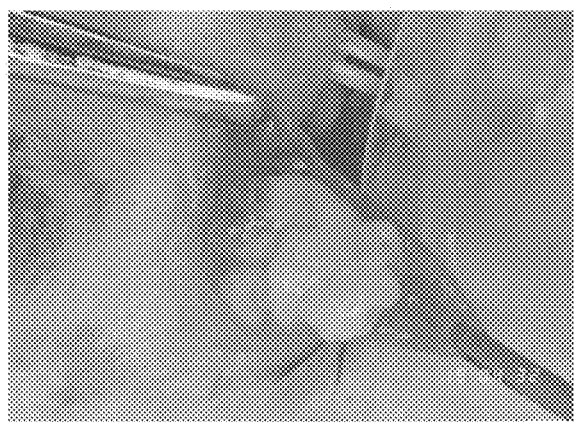

E. Score of 4. Total size of ulcer occupies ½ of the Pouch with loss of pliability.

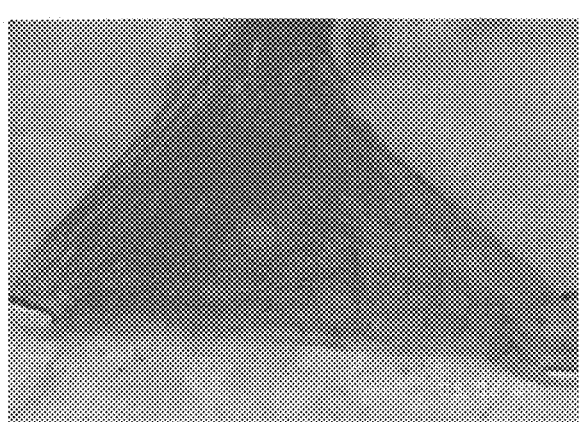

C. Score of 2. Severe erythema and vasodilation with erosion and decreased stippling of superficial mucosa leaving denuded areas.

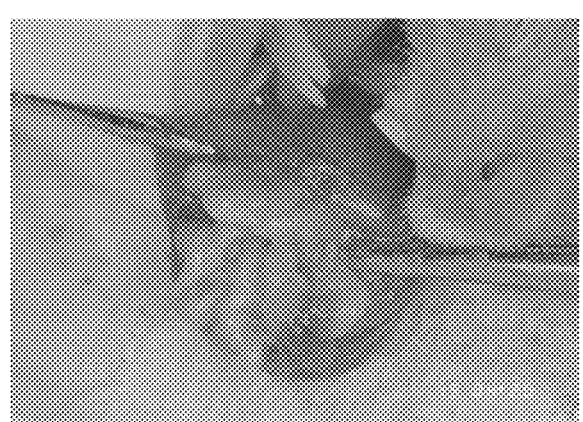

F. Score of 5. Ulceration to virtually all of the pouch. Pouch can only be partially everted.

A
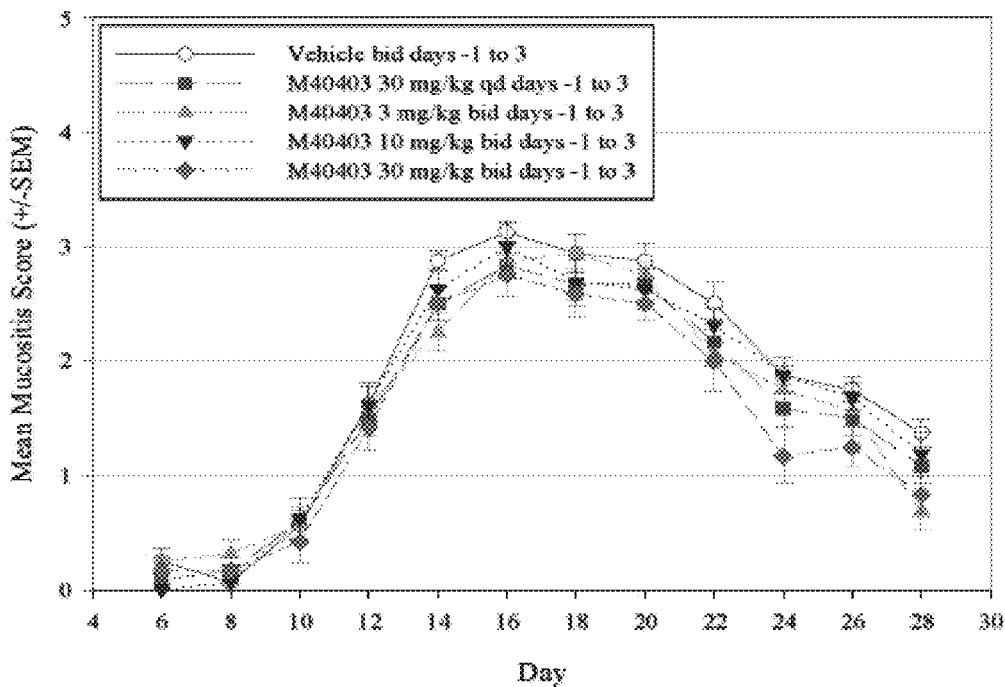
B
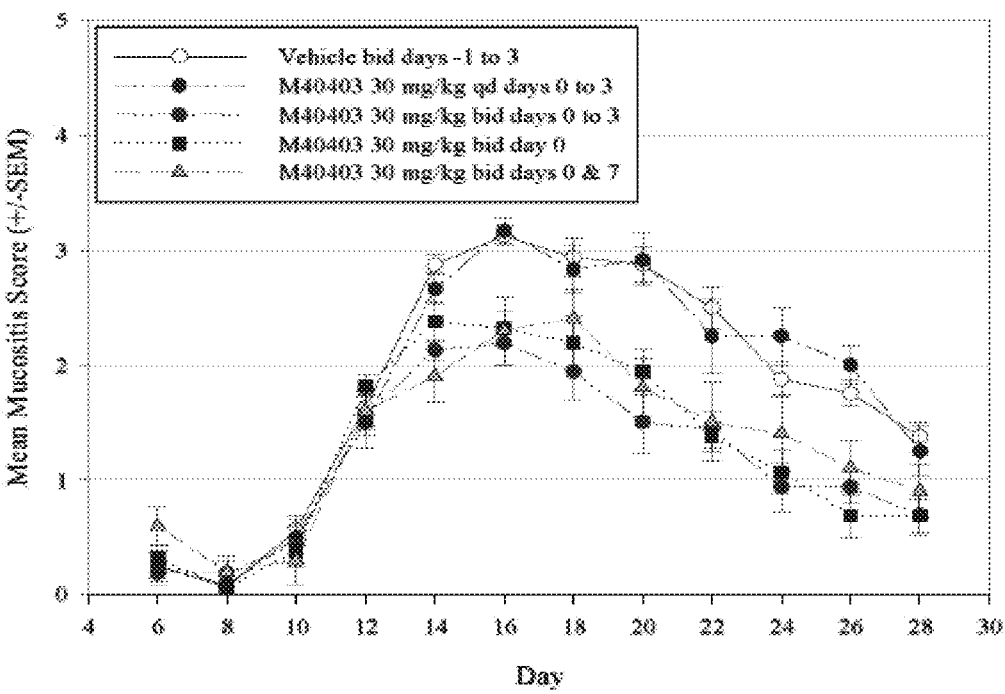
FIG. 11

METHODS OF TREATING ORAL MUCOSITIS

CROSS-REFERENCE TO RELATED APPLICATIONS

This application claims priority from U.S. patent application Ser. No. 15/841,586 filed on Dec. 14, 2017, now U.S. Pat. No. 10,610,533, which claims priority from U.S. patent application Ser. No. 11/871,848 filed on Oct. 12, 2007, now U.S. Pat. No. 9,855,279, which claims priority from U.S. Provisional Application Ser. No. 60/829,291 filed Oct. 12, 2006, each of which are incorporated herein by reference.

STATEMENT REGARDING FEDERALLY SPONSORED RESEARCH OR DEVELOPMENT

Not Applicable.

INCORPORATION-BY-REFERENCE OF MATERIAL SUBMITTED ON A COMPACT DISC

Not Applicable.

BACKGROUND OF THE INVENTION

1. Field of the Invention

This invention relates generally to the treatment of oral mucositis and, more particularly, to methods for treating oral mucositis with a Reactive Oxygen Species ("ROS") scavenger. The compositions and methods are useful in treating oral mucositis.

2. Description of Related Art

Oral ulcerative mucositis is a common, painful, dose-limiting toxicity of drug and radiation therapy for cancer (1). The disorder is characterized by breakdown of the oral mucosa that results in the formation of ulcerative lesions. In granulocytopenic patients, the ulcerations that accompany mucositis are frequent portals of entry for indigenous oral bacteria often leading to sepsis or bacteremia (2). Mucositis occurs to some degree in more than one third of patients receiving anti-neoplastic drug therapy (3). The frequency and severity are significantly greater among patients who are treated with induction therapy for leukemia or with many of the conditioning regimens for bone marrow transplant (4). Among these individuals, moderate to severe mucositis can occur in more than three-quarters of patients. Moderate to severe mucositis occurs in virtually all patients who receive radiation therapy for tumors of the head and neck and typically begins with cumulative exposures of 15 Gy and then worsens as total doses of 60 Gy or more are reached (1-4).

Clinically mucositis progresses through three stages:
1. Atrophic changes accompanied by painful mucosal erythema, which can respond to local anesthetics.
2. Painful ulceration with pseudomembrane formation and, in the case of myelosuppressive treatment, potentially life-threatening sepsis, requiring antimicrobial therapy. Pain is often of such intensity as to require parenteral narcotic analgesia.
3. Spontaneous healing, occurring about 2-3 weeks after cessation of anti-neoplastic therapy.

Standard therapy for mucositis is predominantly palliative, including application of topical analgesics such as lidocaine and/or systemic administration of narcotics and antibiotics. At present, the only approved treatment for oral mucositis is palifermin (Kepivance) which is a member of the fibroblast growth factor (FGF) superfamily of molecules. Palifermin's approval is limited to the treatment of oral mucositis in the patients undergoing conditioning regimens prior to hematopoietic stem cell transplants for the treatment of hematologic malignancies.

The complexity of mucositis as a biological process has only been recently appreciated (5-7). It has been suggested that the condition represents a sequential interaction of oral mucosal cells and tissues, reactive oxygen species, pro-inflammatory cytokines, mediators of apoptosis and local factors such as saliva and the oral microbiota. While epithelial degeneration and breakdown ultimately result in mucosal ulceration, it appears that the early changes associated with radiation-induced mucosal toxicity occur within the endothelium, and connective tissue of the submucosa. For example, electron microscopic evaluation of mucosa within 1 week of radiation shows damage to both endothelium and connective tissue, but not epithelium. It appears that the overall mechanism for mucositis development is similar for both radiation and chemotherapy (8).

Recently, a superoxide dismutase mimetic, M40403, was shown to be effective in an animal models of inflammation (Salvemini et al., Science 286:304-306, 1999) and, more specifically, in an animal model of rheumatoid arthritis (Salvemini et al., Arthritis & Reumatism 44:2909-2921, 2001). Nevertheless, treatment of oral mucositis using M40403 has neither been reported nor suggested.

BRIEF SUMMARY OF THE INVENTION

The present teachings provide methods for treating oral mucositis. A method comprises administering to a patient in need thereof, a superoxide dismutase mimetic. In accordance with one aspect of the invention, the superoxide dismutase mimetic can be represented by the formula:

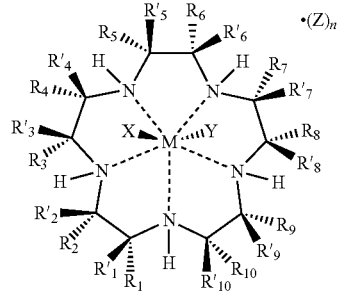

wherein
(i) $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ are independently:
($i^a$) hydrogen; or
(i) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon or α-amino acids; or

3

(i°) a moiety independently selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, —$OP(O)(OR_{11})(OR_{12})$, and substituents attached to the α-carbon of α-amino acids, wherein $R_{11}$ and $R_{12}$ are independently hydrogen or alkyl; and (ii) optionally, one or more of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, $R_9$ or $R'_9$ and $R_{10}$ or $R'_{10}$ together with the carbon atoms to which they are attached independently form a substituted or unsubstituted and saturated, partially saturated, or unsaturated cycle or heterocycle having 3 to 20 carbon atoms; and (iii) optionally, one or more of $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, $R_9$ and $R'_9$, and $R_{10}$ and $R'_{10}$, together with the carbon atom to which they are attached independently form a substituted or unsubstituted and saturated, partially saturated, or unsaturated cycle or heterocycle having 3 to 20 carbon atoms; and (iv) optionally, one or more of $R_{10}$ or $R'_{10}$ and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 3 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (v) optionally, one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, together with a different one of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, which is attached to a different carbon atom in the macrocyclic ligand may be bound to form a strap represented by the formula:

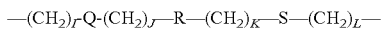

—$(CH_2)_I$-Q-$(CH_2)_J$—R—$(CH_2)_K$—S—$(CH_2)_L$— wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (vi) combinations of any of (i) through (v) above;

wherein

M is a transition metal;

X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol

4 carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof; or X, Y and Z are independently selected from the group consisting of charge-neutralizing anions which are derived from any monodentate or polydentate coordinating ligand and a ligand system and the corresponding anion thereof; or X, Y and Z are independently attached to one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$; and n is an integer from 0 to 3.

Preferably, M is selected from the group consisting of $Mn^{2+}$, $Mn^{3+}$, $Mn^{4+}$, $Mn^{6+}$, $Mn^{7+}$, $Fe^{2+}$, $Fe^{3+}$, $Fe^{4+}$, $Fe^{5+}$, $Ni^{2+}$, $Ni^{3+}$, $Cu^{1+}$, $Cu^{2+}$, $V^{2+}$, $V^{3+}$, $V^{4+}$, and $V^{5+}$.

In an alternative, the superoxide dismutase mimetic can be represented by the formula:

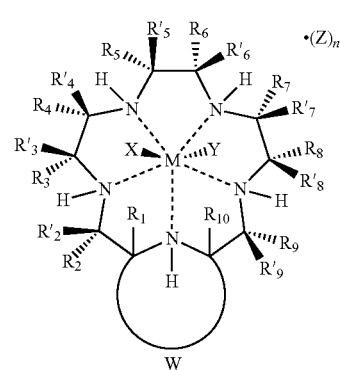

wherein (i) a nitrogen of the macrocycle and two adjacent carbon atoms to which the nitrogen is attached independently form a substituted or unsubstituted, saturated, partially saturated or unsaturated nitrogen-containing heterocycle W having 2 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (ii) one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$ are independently:

(ii$^a$) hydrogen; or (ii$^b$) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon or α-amino acids; or (ii$^c$) a moiety independently selected from the group consisting of $-OR_{11}$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, $-OP(O)(OR_{11})(OR_{12})$, and substituents attached to the α-carbon of α-amino acids, wherein $R_1$, and $R_{12}$ are independently hydrogen or alkyl; and (iii) optionally, one or more of $R_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, $R_9$ or $R'_9$ and $R_{10}$ together with the carbon atoms to which they are attached independently form a substituted or unsubstituted and saturated, partially saturated, or unsaturated cycle or heterocycle having 3 to 20 carbon atoms; and (iv) optionally, one or more of $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a substituted or unsubstituted and saturated, partially saturated, or unsaturated cycle or heterocycle having 3 to 20 carbon atoms; and (v) optionally, one or more of $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 3 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (vi) optionally, one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$, together with a different one of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$, which is attached to a different carbon atom in the macrocyclic ligand may be bound to form a strap represented by the formula:

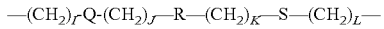

wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (vii) optionally, one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$, may be bound to an atom of heterocycle W to form a strap represented by the formula:

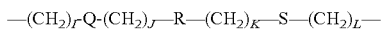

wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (viii) combinations of any of (i) through (vii) above;

wherein

M is a transition metal;

X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof; or X, Y and Z are independently selected from the group consisting of charge-neutralizing anions which are derived from any monodentate or polydentate coordinating ligand and a ligand system and the corresponding anion thereof; or X, Y and Z are independently attached to one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$; and n is an integer from 0 to 3.

Preferably, M is selected from the group consisting of $Mn^{2+}$, $Mn^{3+}$, $Mn^{4+}$, $Mn^{6+}$, $Mn^{7+}$, $Fe^{2+}$, $Fe^{3+}$, $Fe^{4+}$, $Fe^{6+}$, $Ni^{2+}$, $Ni^{3+}$, $Cu^{1+}$, $Cu^{2+}$, $V^{2+}$, $V^{3+}$, $V^{4+}$, and $V^{5+}$, and W is a substituted or unsubstituted pyridino moiety.

In yet another alternative, the superoxide dismutase mimetic can be represented by the formula:

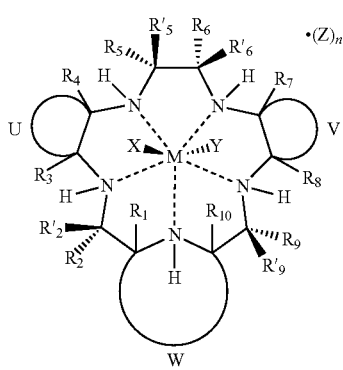

wherein (i) a nitrogen of the macrocycle and two adjacent carbon atoms to which the nitrogen is attached independently form a substituted or unsubstituted, saturated, partially saturated or unsaturated nitrogen-containing heterocycle W having 2 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (ii) two sets of two adjacent carbon atoms of the macrocycle independently form substituted or unsubstituted, saturated, partially saturated or unsaturated, cycles or heterocycles U and V having 3 to 20 carbon atoms; and (iii) $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently:

(iii$^a$) hydrogen; or (iii$^b$) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon or α-amino acids; or (iii$^c$) a moiety independently selected from the group consisting of —$OR_{11}$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, —$OP(O)(OR_{11})(OR_{12})$, and substituents attached to the α-carbon of α-amino acids, wherein $R_{11}$ and $R_{12}$ are independently hydrogen or alkyl; and (iv) optionally, one or more of $R_1$ and $R_2$ or $R'_2$, $R_5$ or $R'_5$ and $R_6$ or $R'_6$, $R_9$ or $R'_9$ and $R_{10}$ together with the carbon atoms to which they are attached independently form a substituted or unsubstituted and saturated, partially saturated, or unsaturated cycle or heterocycle having 3 to 20 carbon atoms; and (v) optionally, one or more of $R_2$ and $R'_2$, $R_5$ and $R'_5$, $R_6$ and $R'_6$, and $R_9$ and $R'_9$, together with the carbon atom to which they are attached independently form a substituted or unsubstituted and saturated, partially saturated, or unsaturated cycle or heterocycle having 3 to 20 carbon atoms; and (vi) optionally, one or more of $R_2$ or $R'_2$ and $R_3$, $R_4$ and $R_5$ or $R'_5$, $R_6$ or $R'_6$ and $R_7$, or $R_8$ and $R_9$ or $R'_9$ together with the carbon atoms to which they are attached independently form a substituted or unsubstituted nitrogen containing heterocycle having 3 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (vii) optionally, one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$, together with a different one of $R_1$, $R_2$, $R'_2$, $R_3$, $R_4$, $R_5$, $R'_5$, $R_6$, $R'_6$, $R_7$, Ra, $R_9$, $R'_9$, and $R_{10}$, which is attached to a different carbon atom in the macrocyclic ligand may be bound to form a strap represented by the formula:

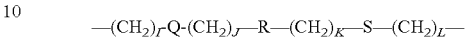

wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (viii) optionally, one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$, may be individually bound to an atom of heterocycles U, V and W to form a strap represented by the formula:

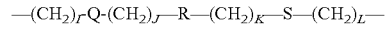

wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (ix) combinations of any of (i) through (viii) above;

wherein

M is a transition metal;

X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof; or X, Y and Z are independently selected from the group consisting of charge-neutralizing anions which are derived from any monodentate or polydentate coordinating ligand and a ligand system and the corresponding anion thereof; or X, Y and Z are independently attached to one or more of $R_1, R_2, R'_2, R_3, R_4, R_5, R'_5, R_6, R'_6, R_7, R_8, R_9, R'_9,$ and $R_{10}$; and n is an integer from 0 to 3.

Preferably, M is selected from the group consisting of $Mn^{2+}, Mn^{3+}, Mn^{4+}, Mn^{6+}, Mn^{7+}, Fe^{2+}, Fe^{3+}, Fe^{4+}, Fe^{6+}, Ni^{2+}, Ni^{3+}, Cu^{1+}, Cu^{2+}, V^{2+}, V^{3+}, V^{4+},$ and $V^{5+}$. In accordance with a futher aspect of the invention, U and V are saturated cycloalkyl heterocycles having 3 to 20 carbon atoms preferably saturated cycloalkyl heterocycles having 4 to 10 carbon atoms, and still more preferably U and V are trans-cyclohexanyl fused rings. In yet another aspect of the present invention, W is a substituted or unsubstituted pyridino moiety, more preferably, U and V are trans-cyclohexanyl fused rings and W is a substituted pyridino moiety. Preferably, the superoxide dismutase mimetic can be represented by the formula:

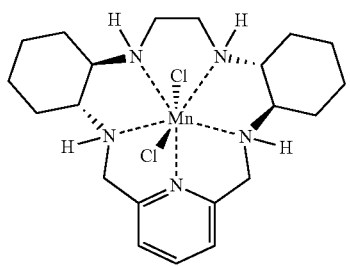

The ROS scavenger can be administered in an amount of at most 0.015 mg/kg, or preferably at most 2 mg/kg. In yet another aspect, the pharmaceutically acceptable formulation is a pharmaceutically acceptable oral formulation and administering comprises administering orally. Preferably, the patient is a human patient and the oral mucositis is a result of chemotherapy or radiation therapy.

Another aspect of the invention can be a method of treating a cancer, the method comprising: a) administering to a subject in need of cancer treatment a pharmaceutical composition comprising a superoxide dismutase mimetic; and b) administering to the subject an effective amount of a cancer treatment, whereby the superoxide dismutase mimetic prevents or reduces oral mucositis in the subject.

The cancer treatment can be comprised of radiation therapy and chemotherapy. In said method of treating a cancer, the superoxide dismutase mimetic can be a reactive oxygen species scavenger, and the pharmaceutical composition can further comprise at least one additional reactive oxygen species scavenger selected from the group consisting of amifostine and N-acetylcysteine. Additionally, the method of treating a cancer can further comprise administering a pharmaceutical composition which upregulates expression of at least one transcription factor which increases expression of one or more genes controlling at least one naturally occurring antioxidant pathway. The composition which upregulates expression of at least one transcription factor can be palifermin, and the transcription factor upregulated can be Nrf-2.

In yet another aspect of the present invention, a kit can be provided for treating oral mucositis, the kit comprising: (a) a ROS scavenger, wherein the ROS scavenger can be a superoxide dismutase; (b) one additional pharmaceutical compound selected from the group consisting of a chemotherapeutic agent; (c) a non-superoxide dismutase mimetic radical scavenger; and (d) instructions for administering the superoxide dismutase to a subject in need of cancer therapy. A chemotherapeutic agent can be selected from a group consisting of all-trans retinoic acid, azacitidine, azathioprine, bleomycin, carboplatin, capecitabine, cisplatin, chlorambucil, cyclophosphamide, cytarabine, daunorubicin, docetaxel, doxifluridine, doxorubicin, epirubicin, epothilone, etoposide, fluorouracil, gemcitabine, hydroxyurea, idarubicin, imatinib, mechlorethamine, mercaptopurine, methotrexate, mitoxantrone, oxaliplatin, paclitaxel, pemetrexed, teniposide, tiguanine, valrubicin, vinblastine, vincristine, vindesine, vinorelbine. A non-superoxide dismutase mimetic radical scavenger can be selected from the group of amifostine and N-acetylcysteine. A superoxide dismutase mimetic can be M40403.

These and other features, aspects and advantages of the present invention will become better understood with reference to the following description, examples and appended claims.

BRIEF DESCRIPTION OF THE DRAWINGS

FIG. 2 is a validated photographic scale for mucositis scoring.

FIG. 5 illustrates the mean daily mucositis scores the groups treated ip with M40403 (i.e. groups 1, 2, 3, and 6), including the control group, and for the groups treated topically with M40403 (i.e. groups 4 and 5).

FIG. 8 is a validated photographic scale for mucositis scoring.

FIG. 11 illustrates the mean daily mucositis scores the groups treated ip with M40403 (i.e. groups 2-9) and for the control group (i.e. group 1).

DETAILED DESCRIPTION OF THE INVENTION

Abbreviations and Definitions

Figure 1:
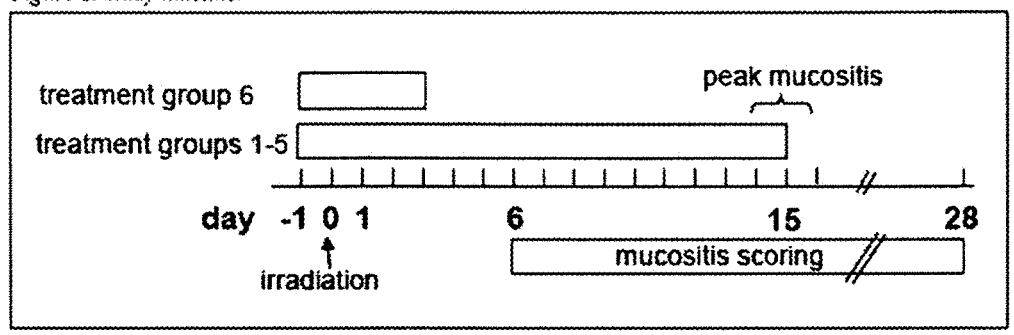
FIG. 1 is a timeline of a study for treatment groups 1-6 to evaluate the effect of M40403, administered by either ip or topical routes. The grade of mucositis was scored, beginning on day 6, and for every second day thereafter, through and including day 28.

To facilitate understanding of the invention, a number of terms and abbreviations as used herein are defined below as follows:

The term "alkenyl", alone or in combination, means an alkyl substituent having one or more double bonds. Examples of such alkenyl substituents include, but are not limited to, ethenyl, propenyl, 1-butenyl, cis-2-butenyl, trans-2-butenyl, iso-butylenyl, cis-2-pentenyl, trans-2-pentenyl, 3-methyl-1-butenyl, 2,3-dimethyl-2-butenyl, 1-pentenyl, 1-hexenyl, 1-octenyl, decenyl, dodecenyl, tetradecenyl, hexadecenyl, cis- and trans-9-octadecenyl, 1,3-pentadienyl, 2,4-pentadienyl, 2,3-pentadienyl, 1,3-hexadienyl, 2,4-hexadienyl, 5,8,11,14-eicosatetraenyl, and 9,12,15-octadecatrienyl.

The term "alkyl", alone or in combination, means a straight-chain or branched-chain alkyl substituent containing from 1 to about 22 carbon atoms, preferably from about 1 to about 18 carbon atoms, and most preferably from about 1 to about 12 carbon atoms. Examples of such substituents include, but are not limited to, methyl, ethyl, n-propyl, isopropyl, n-butyl, isobutyl, sec-butyl, tert-butyl, pentyl, iso-amyl, hexyl, octyl, nonyl, decyl, dodecyl, tetradecyl, hexadecyl, octadecyl and eicosyl.

The terms "alkylcycloalkyl" and "alkenylcycloalkyl" mean a cycloalkyl substituent as defined above which is substituted by an alkyl or alkenyl substituent as defined above. Examples of alkylcycloalkyl and alkenylcycloalkyl substituents include, but are not limited to, 2-ethylcyclobutyl, 1-methylcyclopentyl, 1-hexylcyclopentyl, 1-methylcyclohexyl, 1-(9-octadecenyl)cyclopentyl and 1-(9-octadecenyl)cyclohexyl.

The terms "alkylcycloalkenyl" and "alkenylcycloalkenyl" means a cycloalkenyl substituent as defined above which is substituted by an alkyl or alkenyl substituent as defined above. Examples of alkylcycloalkenyl and alkenylcycloalkenyl substituents include, but are not limited to, 1-methyl-2-cyclopentyl, 1-hexyl-2-cyclopentenyl, 1-ethyl-2-cyclohexenyl, 1-butyl-2-cyclohexenyl, 1-(9-octadecenyl)-2-cyclohexenyl and 1-(2-pentenyl)-2-cyclohexenyl.

The term "alkynyl", alone or in combination, means an alkyl substituent having one or more triple bonds. Examples of such alkynyl groups include, but are not limited to, ethynyl, propynyl (propargyl), 1-butynyl, 1-octynyl, 9-octadecynyl, 1,3-pentadiynyl, 2,4-pentadiynyl, 1,3-hexadiynyl, and 2,4-hexadiynyl.

The term "aralkyl", alone or in combination, means an alkyl or cycloalkyl substituent as defined above in which one hydrogen atom is replaced by an aryl substituent as defined above, such as benzyl, 2-phenylethyl, and the like.

The term "aryl", alone or in combination, means a phenyl or naphthyl substituent which optionally carries one or more substituents selected from alkyl, cycloalkyl, cycloalkenyl, aryl, heterocycle, alkoxyaryl, alkaryl, alkoxy, halogen, hydroxy, amine, cyano, nitro, alkylthio, phenoxy, ether, trifluoromethyl and the like, such as phenyl, p-tolyl, 4-methoxyphenyl, 4-(tert-butoxy)phenyl, 4-fluorophenyl, 4-chlorophenyl, 4-hydroxyphenyl, 1-naphthyl, 2-naphthyl, and the like.

The term "cycloalkenyl", alone or in combination, means a cycloalkyl substituent having one or more double bonds. Examples of cycloalkenyl substituents include, but are not limited to, cyclopentenyl, cyclohexenyl, cyclooctenyl, cyclopentadienyl, cyclohexadienyl and cyclooctadienyl.

The terms "cyclic", "cycle" or "cycylyl" means a ring structure containing 3 to 20 carbon atoms, preferably 5 to 10 carbon atoms, which may be heterocyclic. The cyclic, cycle or cycylyl can also contain more than one ring.

The term "cycloalkenylalkyl" means an alkyl substituent as defined above which is substituted by a cycloalkenyl substituent as defined above. Examples of cycloalkenylalkyl substituents include, but are not limited to, 2-cyclohexen-1-ylmethyl, 1-cyclopenten-1-ylmethyl, 2-(1-cyclohexen-1-yl)ethyl, 3-(1-cyclopenten-1-yl)propyl, 1-(1-cyclohexen-1-ylmethyl)pentyl, 1-(1-cyclopenten-1-yl)hexyl, 6-(1-cyclohexen-1-1-yl)hexyl, 1-(1-cyclopenten-1-yl)nonyl and 1-(1-cyclohexen-1-yl)nonyl.

The term "cycloalkyl", alone or in combination means a cycloalkyl radical containing from 3 to about 10, preferably from 3 to about 8, and most preferably from 3 to about 6, carbon atoms. Examples of such cycloalkyl substituents include, but are not limited to, cyclopropyl, cyclobutyl, cyclopentyl, cyclohexyl, cycloheptyl, cyclooctyl, and perhydronaphthyl.

The term "cycloalkylalkyl" means an alkyl substituent as defined above which is substituted by a cycloalkyl substituent as defined above. Examples of cycloalkylalkyl substituents include, but are not limited to, cyclohexylmethyl, cyclopentylmethyl, (4-isopropylcyclohexyl)methyl, (4-t-butyl-cyclohexyl)methyl, 3-cyclohexylpropyl, 2-cyclohexylmethylpentyl, 3-cyclopentylmethylhexyl, 1-(4-neopentylcyclohexyl)methylhexyl, and 1-(4-isopropylcyclohexyl)methylheptyl.

The term "cycloalkylcycloalkyl" means a cycloalkyl substituent as defined above which is substituted by another cycloalkyl substituent as defined above. Examples of cycloalkylcycloalkyl substituents include, but are not limited to, cyclohexylcyclopentyl and cyclohexylcyclohexyl.

The term "halide" means chloride, fluoride, iodide, or bromide.

The term "heterocyclic", "heterocycle" or "heterocycylyl" means a cyclic, cycle or cycylyl containing at least one other kind of atom, in addition to carbon, in the ring. Such atoms include, but are not limited to, nitrogen, oxygen and sulfur. The heterocyclic can also contain more than one ring. Examples of heterocyclics include, but are not limited to, pyrrolidinyl, piperidyl, imidazolidinyl, tetrahydrofuryl, tetrahydrothienyl, furyl, thienyl, pyridyl, quinolyl, isoquinolyl, pyridazinyl, pyrazinyl, indolyl, imidazolyl, oxazolyl, thiazolyl, pyrazolyl, pyridinyl, benzoxadiazolyl, benzothiadiazolyl, triazolyl and tetrazolyl groups.

The term "nitrogen containing heterocycle" means a ring structure in which 2 carbons and a nitrogen of the ring are shared with the fifteen-membered macrocyclic ligand. The nitrogen containing heterocycle can contain 2 to 20, preferably 4 to 10, carbon atoms, can be substituted or unsubstituted, saturated, partially saturated or unsaturated, and can also contain nitrogen, oxygen and/or sulfur atoms in the portion of the ring which is not also part of the fifteen-membered macrocyclic ligand.

The term "oral mucositis" shall also include stomatitis, small intestine-titis, large intestine-titis, proctitis, and similar conditions affecting the mucosal lining of the entire gastrointestinal tract, and related conditions.

The term "R groups" means the group of variable substituents designated as "R" attached to the carbon atoms of the macrocycle, i.e., $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$.

The term "saturated, partially saturated or unsaturated cycle or heterocycle" means a fused ring structure in which 2 carbons of the ring are also part of the fifteen-membered macrocyclic ligand in which the ring can contain no double bonds (in the case of a saturated ring structure) or at least one double bond, which may be conjugated or unconjugated with another double bond. The ring structure can contain 3 to 20 carbon atoms, preferably 5 to 10 carbon atoms, which may be heterocyclic. The cyclic can also contain more than one ring.

In addition, the following abbreviations have the following meanings:

| | |
|---|---|
| AUC | Area under the curve |
| bid | Twice daily |
| FGF | Fibroblast growth factor |
| g, mg, ml, kg | Gram, milligram, milliliter, kilogram |
| Gy | Gray |
| ip | Intraperitoneal |
| ma | Milliamp |
| mM | Millimolar |
| mm, cm | Millimeter, centimeter |
| SEM | Standard error of the mean |
| top | Topical |

Methods for Treating Oral Mucositis

The present invention involves the administration of a ROS scavenger in the treatment of oral mucositis. A ROS scavenger of the present invention is a superoxide dismutase mimetic, a non-proteinaceous molecule that catalyzes the conversion the of the superoxide radical, $O_2^-$, to molecular oxygen and hydrogen peroxide. Such a molecule can, like a native superoxide dismutase enzyme, reduce cell injury resulting from superoxide radical found in diseases involving oxidative stress such as inflammation (Salvemini et al, Arthritis & Rheumatism 44:2909-2921, 2001). The ROS scavengers of the present invention can be pentaaza-macrocyclic complexes, and more specifically, those compositions as disclosed in U.S. Pat. Nos. 5,610,293, 5,637,578, 5,874,421, 5,976,498, 6,084,093, 6,180,620, 6,204,259, 6,214,817, 6,245,758, 6,395,725, and 6,525,041, each of which is incorporated herein by reference in its entirety.

The superoxide dismutase mimetics of the present invention can be represented by the following formula:

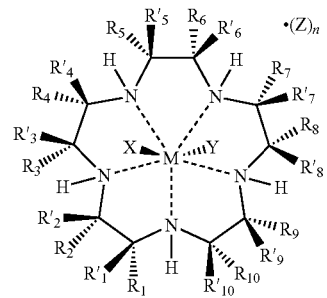

wherein (i) $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$ are independently:

($i^a$) hydrogen; or ($i^b$) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and aralkyl radicals and radicals attached to the α-carbon or α-amino acids heterocyclyl; or ($i^c$) a moiety independently selected from the group consisting of —$OR_1$, —$NR_{11}R_{12}$, —$COR_{11}$, —$CO_2R_{11}$, —$CONR_{11}R_{12}$, —$SR_{11}$, —$SOR_{11}$, —$SO_2R_{11}$, —$SO_2NR_{11}R_{12}$, —$N(OR_{11})(R_{12})$, —$P(O)(OR_{11})(OR_{12})$, —$P(O)(OR_{11})(R_{12})$, —$OP(O)(OR_{11})(OR_{12})$, and substituents attached to the α-carbon of α-amino acids, wherein $R_{11}$ and $R_{12}$ are independently hydrogen or alkyl; and (ii) optionally, one or more of $R_1$ or $R'_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and $R_8$ or $R'_8$, $R_9$ or $R'_9$ and $R_{10}$ or $R'_{10}$ together with the carbon atoms to which they are attached independently form a substituted or unsubstituted and saturated, partially saturated, or unsaturated cycle or heterocycle having 3 to 20 carbon atoms; and (iii) optionally, one or more of $R_1$ and $R'_1$, $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, $R_9$ and $R'_9$, and $R_{10}$ and $R'_{10}$, together with the carbon atom to which they are attached independently form a substituted or unsubstituted and saturated, partially saturated, or unsaturated cycle or heterocycle having 3 to 20 carbon atoms; and (iv) optionally, one or more of $R_{10}$ or $R'_{10}$ and $R_1$ or $R'_1$, $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 3 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (v) optionally, one or more of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, together with a different one of $R_1$, $R'_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, $R_{10}$, and $R'_{10}$, which is attached to a different carbon atom in the macrocyclic ligand may be bound to form a strap represented by the formula:

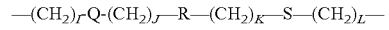

—$(CH_2)_r$-Q-$(CH_2)_j$—R—$(CH_2)_K$—S—$(CH_2)_L$— wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (vi) combinations of any of (i) through (v) above.

Thus, the pentaaza-macrocyclic ligand compositions useful in the present invention can have any combinations of substituted or unsubstituted R groups, saturated, partially saturated or unsaturated cyclics, heterocyclics, nitrogen containing heterocycles, or straps as defined above.

M can be a transition metal, preferably $Mn^{2+}$, $Mn^{3+}$, $Mn^{4+}$, $Mn^{6+}$, $Mn^{7+}$, $Fe^{2+}$, $Fe^{3+}$, $Fe^{4+}$, $Fe^{6+}$, $Ni^{2+}$, $Ni^{3+}$, $Cu^{1+}$, $Cu^{2+}$, $V^{2+}$, $V^{3+}$, $V^{4+}$, or $V^{5+}$. X, Y and Z can independently be selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof; or X, Y and Z are independently selected from the group consisting of charge-neutralizing anions which are derived from any monodentate or polydentate coordinating ligand and a ligand system and the corresponding anion thereof; or X, Y and Z are independently attached to one or more of $R_1$, $R'_1$, $R_2$, $R'_2$, $R_3$, $R'_3$, $R_4$, $R'_4$, $R_5$, $R'_5$, $R_6$, $R'_8$, $R_7$, $R'_7$, $R_8$, $R'_8$, $R_9$, $R'_9$, $R_{10}$, and $R'_{10}$. n is preferably an integer from 0 to 3.

Alternatively, the superoxide dismutase mimetic can be represented by the formula:

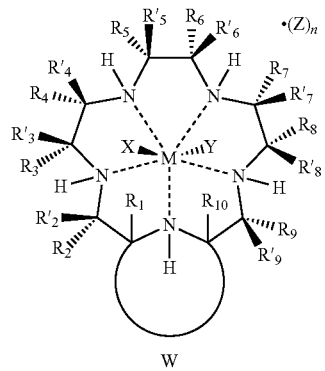

wherein (i) a nitrogen of the macrocycle and two adjacent carbon atoms to which the nitrogen is attached independently form a substituted or unsubstituted, saturated, partially saturated or unsaturated nitrogen-containing heterocycle W having 2 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (ii) one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$ are independently:

(ii$^a$) hydrogen; or (ii$^b$) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon or α-amino acids; or (ii$^c$) a moiety independently selected from the group consisting of $-OR_1$, $-NR_{11}R_{12}$, $-COR_{11}$, $-CO_2R_{11}$, $-CONR_{11}R_{12}$, $-SR_{11}$, $-SOR_{11}$, $-SO_2R_{11}$, $-SO_2NR_{11}R_{12}$, $-N(OR_{11})(R_{12})$, $-P(O)(OR_{11})(OR_{12})$, $-P(O)(OR_{11})(R_{12})$, $-OP(O)(OR_{11})(OR_{12})$, and substituents attached to the α-carbon of α-amino acids, wherein $R_{11}$ and $R_{12}$ are independently hydrogen or alkyl; and (iii) optionally, one or more of $R_1$ and $R_2$ or $R'_2$, $R_3$ or $R'_3$ and $R_4$ or $R'_4$, $R_5$ or $R'_5$ and $R_6$ or $R'_6$, $R_7$ or $R'_7$ and Ra or $R'_8$, $R_9$ or $R'_9$ and $R_{10}$ together with the carbon atoms to which they are attached independently form a substituted or unsubstituted and saturated, partially saturated, or unsaturated cycle or heterocycle having 3 to 20 carbon atoms; and (iv) optionally, one or more of $R_2$ and $R'_2$, $R_3$ and $R'_3$, $R_4$ and $R'_4$, $R_5$ and $R'_5$, $R_6$ and $R'_6$, $R_7$ and $R'_7$, $R_8$ and $R'_8$, and $R_9$ and $R'_9$, together with the carbon atom to which they are attached independently form a substituted or unsubstituted and saturated, partially saturated, or unsaturated cycle or heterocycle having 3 to 20 carbon atoms; and (v) optionally, one or more of $R_2$ or $R'_2$ and $R_3$ or $R'_3$, $R_4$ or $R'_4$ and $R_5$ or $R'_5$, $R_6$ or $R'_6$ and $R_7$ or $R'_7$, or $R_8$ or $R'_8$ and $R_9$ or $R'_9$ together with the carbon atoms to which they are attached independently form a substituted or unsubstituted nitrogen containing heterocycle having 3 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (vi) optionally, one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$, together with a different one of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$, which is attached to a different carbon atom in the macrocyclic ligand may be bound to form a strap represented by the formula:

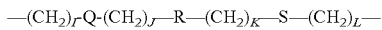

—(CH$_2$)$_I$-Q-(CH$_2$)$_J$—R—(CH$_2$)$_K$—S—(CH$_2$)$_L$— wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (vii) optionally, one or more of $R_1$, $R_2$, $R'_2$, $R_3$, $R'_3$, $R_4$, $R'_4$, $R_5$, $R'_5$, $R_6$, $R'_6$, $R_7$, $R'_7$, $R_8$, $R'_8$, $R_9$, $R'_9$, and $R_{10}$, may be bound to an atom of heterocycle W to form a strap represented by the formula:

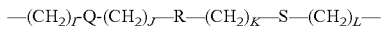

—(CH$_2$)$_I$-Q-(CH$_2$)$_J$—R—(CH$_2$)$_K$—S—(CH$_2$)$_L$— wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (viii) combinations of any of (i) through (vii) above.

Thus, the pentaaza-macrocyclic ligand compositions useful in the present invention can have any combinations of substituted or unsubstituted R groups, saturated, partially saturated or unsaturated cyclics, heterocyclics, nitrogen containing heterocycles, or straps as defined above, which may or may not independently connect the W loop and the pentaaza macrocycle.

M can be a transition metal, preferably $Mn^{2+}$, $Mn^{3+}$, $Mn^{4+}$, $Mn^{6+}$, $Mn^{7+}$, $Fe^{2+}$, $Fe^{3+}$, $Fe^{4+}$, $Fe^{6+}$, $Ni^{2+}$, $Ni^{3+}$, $Cu^{1+}$, $Cu^{2+}$, $V^{2+}$, $V^{3+}$, $V^{4+}$, or $V^{5+}$. X, Y and Z can independently be selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof. n is preferably an integer from 0 to 3. W can be a substituted or unsubstituted pyridino moiety.

In another alternative, the superoxide dismutase mimetic can be represented by the formula:

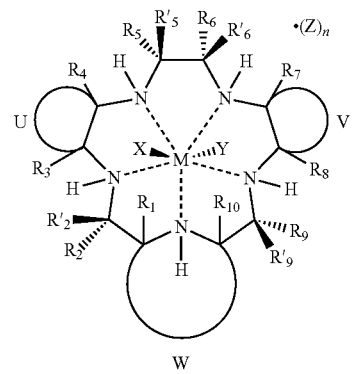

wherein (i) a nitrogen of the macrocycle and two adjacent carbon atoms to which the nitrogen is attached independently form a substituted or unsubstituted, saturated, partially saturated or unsaturated nitrogen-containing heterocycle W having 2 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (ii) two sets of two adjacent carbon atoms of the macrocycle independently form substituted or unsubstituted, saturated, partially saturated or unsaturated, cycles or heterocycles U and V having 3 to 20 carbon atoms; and (iii) $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are independently:

(iii$^a$) hydrogen; or (iii$^b$) a moiety independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, heterocyclyl, and aralkyl radicals and radicals attached to the α-carbon or α-amino acids; or (iii$^c$) a moiety independently selected from the group consisting of —OR$_1$, —NR$_{11}$R$_{12}$, —COR$_{11}$, —CO$_2$R$_{11}$, —CONR$_{11}$R$_{12}$, —SR$_{11}$, —SOR$_{11}$, —SO$_2$R$_{11}$, —SO$_2$NR$_{11}$R$_{12}$, —N(OR$_{11}$)(R$_{12}$), —P(O)(OR$_{11}$)(OR$_{12}$), —P(O)(OR$_{11}$)(R$_{12}$), —OP(O)(OR$_{11}$)(OR$_{12}$), and substituents attached to the α-carbon of α-amino acids, wherein R$_1$, and R$_{12}$ are independently hydrogen or alkyl; and (iv) optionally, one or more of R$_1$ and R$_2$ or R'$_2$, R$_5$ or R'$_5$ and R$_6$ or R'$_6$, R$_9$ or R'$_9$ and R$_{10}$ together with the carbon atoms to which they are attached independently form a substituted or unsubstituted and saturated, partially saturated, or unsaturated cycle or heterocycle having 3 to 20 carbon atoms; and (v) optionally, one or more of R$_2$ and R'$_2$, R$_5$ and R'$_5$, R$_6$ and R'$_6$, and R$_9$ and R'$_9$, together with the carbon atom to which they are attached independently form a substituted or unsubstituted and saturated, partially saturated, or unsaturated cycle or heterocycle having 3 to 20 carbon atoms; and (vi) optionally, one or more of R$_2$ or R'$_2$ and R$_3$, R$_4$ and R$_5$ or R'$_5$, R$_6$ or R'$_6$ and R$_7$, or R$_8$ and R$_9$ or R'$_9$ together with the carbon atoms to which they are attached independently form a substituted or unsubstituted nitrogen containing heterocycle having 3 to 20 carbon atoms, which may be an aromatic heterocycle in which case the hydrogen attached to the nitrogen which is both part of the heterocycle and the macrocycle and the R groups attached to the carbon atoms which are both part of the heterocycle and the macrocycle are absent; and (vii) optionally, one or more of R$_1$, R$_2$, R'$_2$, R$_3$, R$_4$, R$_5$, R'$_5$, R$_6$, R'$_6$, R$_7$, R$_8$, R$_9$, R'$_9$, and R$_{10}$, together with a different one of R$_1$, R$_2$, R'$_2$, R$_3$, R$_4$, R$_5$, R'$_5$, R$_6$, R'$_6$, R$_7$, R$_8$, R$_9$, R'$_9$, and R$_{10}$, which is attached to a different carbon atom in the macrocyclic ligand may be bound to form a strap represented by the formula:

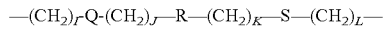

wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (viii) optionally, one or more of R$_1$, R$_2$, R'$_2$, R$_3$, R$_4$, R$_5$, R'$_5$, R$_6$, R'$_6$, R$_7$, R$_8$, R$_9$, R'$_9$, and R$_{10}$, may be individually bound to an atom of heterocycles U, V and W to form a strap represented by the formula:

wherein

I, J, K and L independently are integers from 0 to 10 and Q, R and S are independently selected from the group consisting of alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, aza, amide, ammonium, oxa, thia, sulfonyl, sulfinyl, sulfonamide, phosphoryl, phosphinyl, phosphino, phosphonium, keto, ester, alcohol, carbamate, urea, thiocarbonyl, borates, boranes, boraza, silyl, siloxy, silaza, and combinations thereof; and (ix) combinations of any of (i) through (viii) above;

Thus, the pentaaza-macrocyclic ligand compositions useful in the present invention can have any combinations of substituted or unsubstituted R groups, saturated, partially saturated or unsaturated cyclics, heterocyclics, nitrogen containing heterocycles, or straps as defined above, which may or may not independently connect the W, U or V loops and the pentaaza macrocycle.

M can be a transition metal, preferably Mn$^{2+}$, Mn$^{3+}$, Mn$^{4+}$, Mn$^{6+}$, Mn$^{7+}$, Fe$^{2+}$, Fe$^{3+}$, Fe$^{4+}$, Fe$^{6+}$, Ni$^{2+}$, Ni$^{3+}$, Cu$^{1+}$, Cu$^{2+}$, V$^{2+}$, V$^{3+}$, V$^{4+}$, or V$^{5+}$. X, Y and Z can independently be selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof. n is preferably an integer from 0 to 3. W can be a substituted or unsubstituted pyridino moiety. U and V can be independently saturated cycloalkyl heterocycles having 3 to 20 carbon atoms, more preferably 4 to 10 carbon atoms, still more preferably trans-cyclohexanyl fused rings. U and V can be trans-cyclohexanyl fused rings while W is a substituted pyridino moiety.

In certain embodiments, the superoxide dismutase mimetic can be the compound identified as M40403, which can be represented by the formula:

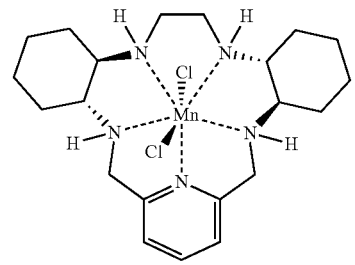

The present invention can involve administration of a ROS scavenger, in particular, M40403 or a suitable derivative or analog thereof as described above, to a patient in need thereof. Administration of the ROS scavenger, in particular M40403, can be by numerous routes of administration well known to those of skill in the art.

Administration of the ROS scavenger can be by any suitable route of administration such as, for example, oral, buccal, sublingual, intranasal, inhalation, rectal, intravaginal, transdermal, intradermal, subcutaneous, intramuscular, intraperitoneal, intravenous, intraarterial, intrasternal, intrathecal and the like.

Pharmaceutically acceptable formulations for parenteral or nonparenteral drug delivery are known in the art such as, for example, are set forth in Remington's Pharmaceutical Sciences, 18th Edition, Mack Publishing (1990). For pharmaceutical compositions and methods of treatment disclosed herein, dosage forms and administration regimes can be determined using standard methods known to skilled artisans, for example as set forth in standard references such as Remington: the Science and Practice of Pharmacy (Alfonso R. Gennaro ed. 19th ed. 1995); Hardman, J. G., et al., Goodman & Gilman's The Pharmacological Basis of Therapeutics, Ninth Edition, McGraw-Hill, 1996; and Rowe, R. C., et al., Handbook of Pharmaceutical Excipients, Fourth Edition, Pharmaceutical Press, 2003.

Pharmaceutical compositions can be formulated to be compatible with the intended route of administration. Solutions or suspensions used for parenteral, intradermal or subcutaneous application can include: a sterile diluent, such as water for injection, saline solution, fixed oils, polyethylene glycols, glycerine, propylene glycol or other synthetic solvents; antibacterial agents, such as benzyl alcohol or methyl parabens; antioxidants, such as ascorbic acid or sodium bisulfite; chelating agents, such as ethylenediaminetetraacetic acid (EDTA); buffers such as acetates, citrates or phosphates, and agents for the adjustment of tonicity, such as sodium chloride or dextrose. Suitable carriers include physiological saline, bacteriostatic water, Cremophor® EL (BASF, Parsippany, N.J.) or phosphate buffered saline (PBS). The compositions can be stable during manufacture and storage and preserved against contamination from microorganisms, such as bacteria and fungi.

Proper fluidity can be maintained, for example, by using a coating such as lecithin; by maintaining the required particle size in the case of dispersion, and by using surfactants. Various antibacterial and antifungal agents, such as parabens, chlorobutanol, phenol, ascorbic acid, and thimerosal, can control microorganism contamination. Isotonic agents, such as sugars, polyalcohols such as manitol, sorbitol, and sodium chloride can be included in the composition. Compositions that delay absorption can be prepared by including such agents as aluminum monostearate and gelatin.

Sterile injectable solutions can be prepared by incorporating the active compound (e.g., an SCMP) in an appropriate solvent with one or more ingredient, followed by sterilization. Generally, dispersions are prepared by incorporating the active compound into a sterile vehicle that contains a basic dispersion medium and any other required ingredients. Sterile powders for the preparation of sterile injectable solutions include vacuum- and freeze-drying that yield a powder containing the active ingredient and any desired ingredient from a sterile solution. The concentration of active drug, i.e. the ROS scavenger, can be from about 0.1% to about 90% by weight, from about 5% to about 20% by weight, from about 5% to about 17% by weight, from about 8% to about 14% by weight or, in certain embodiments, about 10% by weight.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally. Pharmaceutically compatible binding agents, and/or adjuvant materials can be included. Tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, primogel, or corn starch; a lubricant such as magnesium stearate or sterotes; a glidant such as colloidal silicon dioxide; a sweetening agent such as sucrose or saccharin; or a flavoring agent such as peppermint, methyl salicylate, or orange flavoring. The concentration of active drug, i.e. the ROS scavenger, can be from about 0.1% to about 99% by weight, from about 5% to about 95% by weight, from about 10% to about 90% by weight, from about 15% to about 85% by weight, from about 20% to about 80% by weight, from about 25% to about 75% by weight, from about 30% to about 70% by weight, from about 35% to about 64% by weight or from about 40% to about 60% by weight.

Administration by inhalation, can be by aerosol spray from a nebulizer or a pressurized container that contains a suitable propellant, e.g., a gas such as carbon dioxide.

Systemic administration can also be transmucosal or transdermal. For transmucosal or transdermal administration, penetrants that can permeate the target barrier(s) are selected. Transmucosal penetrants include detergents, bile salts and fusidic acid derivatives. Nasal sprays or suppositories can be used for transmucosal administration. For transdermal administration, the active compounds are formulated into ointments, salves, gels or creams.

The compounds can also be prepared as suppositories (with bases such as cocoa butter and other glycerides) or retention enemas for rectal delivery.

In various embodiments, the active compounds can be prepared with carriers that protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid (Alza Corporation; Mountain View, Calif. and Nova Pharmaceuticals, Inc.; Lake Elsinore, Calif.). Liposomal suspensions can also be used as pharmaceutically acceptable carriers (Eppstein, 1985).

Oral formulations or parenteral compositions in unit dosage form can be created to facilitate administration and dosage uniformity. Unit dosage form refers to physically discrete units suited as single doses for a subject to be treated, containing a therapeutically effective quantity of active compound in association with the required pharmaceutical carrier. The specification for unit dosage forms are dictated by, and directly dependent on, the unique characteristics of the active compound and the particular desired therapeutic effect, and the inherent limitations of compounding the active compound.

A typical dose of the ROS scavenger can be from about 0.1 mg up to about 1000 mg or from about 0.001 up to about 10 mg/kg body weight. Doses of 5 mg/kg and 10 mg/kg administered intraperitoneally have shown to produce beneficial effects in rats treated with type II collagen to induced arthritis (Salvemini et al., Arthritis & Rheumatism, 44:2909-2921, 2001). A dose of 2 mg/kg produced less of an effect that was nevertheless significantly different from that in placebo animals. Low doses of a ROS scavenger can be doses of less than about 5 mg/kg or doses equal to or less than about 2 mg/kg body weight, in particular, a dose of about 0.1 mg, about 0.2 mg, about 0.5 mg, about 0.8 mg, about 1 mg, about 2 mg, about 5 mg, about 8 mg, about 10 mg, about 20 mg, about 50 mg, about 80 mg, about 100 mg or about 200 mg or about 0.001 mg/kg, about 0.002 mg/kg, about 0.005 mg/kg, about 0.01 mg/kg, about 0.02 mg/kg, about 0.05 mg/kg, about 0.1 mg/kg, about 0.2 mg/kg, about 0.5 mg/kg, about 1 mg/kg, about 2 mg/kg, about 3 mg/kg or about 4 mg/kg body weight.

Total daily doses of the ROS scavenger can be administered in single or divided doses and in amounts such as, for example, from about 1 to about 2 mg/kg body weight daily and more usually about 0.05 to 1 mg/kg. Dosage unit compositions may contain such amounts of submultiples thereof to make up the total dose. However, one skilled in the art will recognize that the total dosage will vary on the particular composition the particular ROS scavenger administered.

Individuals receiving treatment are, typically, human patients, however, patients receiving treatment can also be animal including companion animal such as dogs and cats, farm animal such as cows, horses, swine as well as birds and exotic animal such as zoo animals.

The amount of active ingredients that may be combined with the carrier materials to produce a single dosage form can vary depending upon the host treated and the particular mode of administration. It will be appreciated that the unit content of active ingredients contained in an individual dose of each dosage form need not in itself constitute an effective amount, as the necessary effective amount could be reached by administration of a number of individual doses. The selection of dosage depends upon the dosage form utilized, the condition being treated, and the particular purpose to be achieved according to the determination of those skilled in the art.

The dosage regimen for treating a disease condition with the compounds and/or compositions of this invention can be selected in accordance with a variety of factors, including the type, age, weight, sex, diet and medical condition of the patient, the route of administration, pharmacological considerations such as the activity, efficacy, pharmacokinetic and toxicology profiles of the particular compound employed, whether a drug delivery system is utilized and whether the compound is administered as part of a drug combination. Thus, the dosage regimen actually employed can, therefore, can deviate from the preferred dosage regimen set forth above.

In various embodiments, the present invention can also involve kits. Such kits can include pharmaceutical compositions and, in addition in certain embodiments, instructions for administration. When supplied as a kit, the different components of the composition can be packaged in separate containers and admixed immediately before use. Such packaging of the components separately can, in certain instances, permit long-term storage without losing activity of the components. In addition, if more than one route of administration is intended or more than one schedule for administration is intended, the different components can be packaged separately and not mixed prior to use. In various embodiments, the different components can be packaged in one composition for administration together.

Kits may also include reagents in separate containers such as, for example sterile water or saline to be added to a lyophilized active component packaged separately. For example, sealed glass ampules may contain lyophilized ROS scavenger, sterile water, sterile saline or sterile each of which has been packaged under a neutral non-reacting gas, such as nitrogen. Ampules may consist of any suitable material, such as glass, organic polymers, such as polycarbonate, polystyrene, etc., ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, etc. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, etc.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, etc. Detailed instructions may not be physically associated with the kit; instead, a user may be directed to an internet web site specified by the manufacturer or distributor of the kit, or supplied as electronic mail.

EXAMPLES

Without further elaboration, it is believed that one skilled in the art can, using the preceding description, utilize the present invention to its fullest extent. The following specific examples are offered by way of illustration and not by way of limiting the remaining disclosure.

Example 1

Objective

The objective of this study is to evaluate the effect of M40403, administered by either ip or topical routes, with 2 different schedules, on the frequency, severity and duration of oral mucositis induced in hamsters by acute radiation.

Summary

M40403 was given as an intraperitoneal (ip) injection at a 30 mg/kg/dose twice daily (a) from day −1 to day 15, or (b) day −1 to day 3. M40403 was also given by ip injection at a dose of 3 mg/kg twice daily from day −1 to day 15. In addition, M40403 was given as a topical dose directed to the buccal mucosa in 0.2 ml doses of either 3 mg/ml or 30 mg/ml twice daily from day −1 to day 15. The greatest reduction in oral mucositis was seen in the group treated with M40403 at 30 mg/kg/dose ip twice daily from day −1 to day 3. This group had a statistically significant reduction in the number of animal days with a mucositis score of 3 or higher (P<0.001) and significantly lower mean mucositis scores than the control group on days 18 (P=0.041), 20 (P<0.001), 22 (P<0.001), 24 (P<0.001) and 26 (P=0.002). No other treatment groups in this study showed a reduction in mucositis either by long term (day-1 to day 15) ip dosing or by topical dosing. This study establishes a schedule-dependent dosing method for the treatment of oral mucositis with M40403.

Acute Radiation Model

The acute radiation model in hamsters, developed by the Principal Investigator, has proven to be an accurate, efficient and cost-effective technique to provide a preliminary evaluation of anti-mucositis compounds (9). The course of mucositis in this model is well defined and results in peak scores approximately 14-16 Days following radiation. The acute model has little systemic toxicity, resulting in few hamster deaths, thus permitting the use of smaller groups (N=7-8) for initial efficacy studies. It has also been used to study specific mechanistic elements in the pathogenesis of mucositis. Molecules that show efficacy in the acute radiation model may be further evaluated in the more complex models of fractionated radiation, chemotherapy, or concomitant therapy.

In this study, an acute radiation dose of 40 Gy on day 0 was administered locally to the cheek pouch. Clinically significant mucositis was observed on days 12 through 28.

Protocol Summary

Forty-eight male Syrian Golden Hamsters were divided randomly into 6 groups of 8 animals and given an acute radiation dose of 40 Gy directed to their left buccal cheek pouch. This was accomplished by anesthetizing the animals and everting the left buccal pouch, while protecting the rest of the animal with a lead shield. Test materials were given topically or by ip injection twice daily as detailed in Table 1. Mucositis was evaluated clinically starting on Day 6, and continued on alternate days until day 28.

Evaluation

Mucositis Evaluation

The grade of mucositis was scored, beginning on day 6, and for every second day thereafter, through and including day 28 (for scoring scheme, see Table 2 and FIG. 2). The effect on mucositis of each drug treatment compared to ip vehicle-treated controls was assessed according to the following parameters:

The difference in the number of days hamsters in each group have ulcerative (score ≥3) mucositis.

On each evaluation day, the number of animals with a blinded mucositis score of ≥3 in each drug treatment group was compared to the vehicle-treated control group. Differences were compared on a cumulative basis and statistical significance was determined by chi-square analysis. Efficacy, in this analysis, is defined as a significant reduction in the number of days that a group of animals had ulcerations (scores ≥3) when compared to the control group.

TABLE 2

Table 2 ACT-02: Mucositis Scoring.

| Score: | Description: |
| --- | --- |
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

Rank Sum Differences in Daily Mucositis Scores.

For each evaluation day the scores of the control group were compared to those of the treated groups using non-parametric rank sum analysis. Treatment success was considered as a statistically significant lowering of scores in the treated group on 2 or more days from day 6 to day 28.

Weights and Survival

All animals were weighed daily and their survival recorded, in order to assess possible differences in animal weight among treatment groups as an indication for mucositis severity and/or possible toxicity resulting from the treatments.

Study Design

All forty-eight (48) male Syrian Golden Hamsters were given an acute radiation dose of 40 Gy directed to their left buccal cheek pouch. This was accomplished by anesthetizing the animals and everting the left buccal pouch, while protecting the rest of the animal with a lead shield. Test materials were given either topically or by ip injection twice daily as detailed in Table 1. Mucositis was evaluated clinically starting on day 6, and continuing on alternate days until day 28. The study timeline is depicted in FIG. 1. Dose levels were determined based on the results of a previous acute toxicity study (data not shown), and the levels shown in Table 1.

TABLE 1

Table 1. ACT-02. Study Design

| Group Number | Number of Animals | Treatment | Treatment Schedule* | Volume (mL) |
| --- | --- | --- | --- | --- |
| 1 | 8 males | Vehicle, ip, bid | Day −1 to 15 | Adjust per body weigh |
| 2 | 8 males | M40403, ip, bid 3 mg/kg | Day −1 to 15 | Adjust per body weigh |
| 3 | 8 males | M40403, ip, bid 30 mg/kg | Day −1 to 15 | Adjust per body weigh |
| 4 | 8 males | M40403, topical, bid 3 mg/ml | Day −1 to 15 | 0.2 ml per dose |
| 5 | 8 males | M40403, topical, bid 30 mg/ml | Day −1 to 15 | 0.2 ml per dose |
| 6 | 8 males | M40403, ip, bid 30 mg/kg | Day −1 to 3 | Adjust per body weigh |

*The first close on day 0 was performed 30 minutes prior to radiation. The second dose was given at least 4 hours after radiation.

At the end of the study on day 28, the animals in group 1 were used in a modified pK study as follows: Two animals were injected with vehicle and blood was drawn 30 minutes after the injection. Six animals were injected with 30 mg/kg of M40403. At 15, 30 and 90 minutes post injection, 2 animals from this group were sacrificed and blood was obtained by cardiac puncture. Blood was collected in lithium heparin, kept on ice for 30 minutes and the plasma was obtained after centrifugation. Plasma was transferred to labeled tubes, snap frozen in liquid nitrogen and shipped to ActivBiotics.

Material and Methods

Location of Study Performance

The study was performed at Biomodels AAALAC accredited facility in Cambridge Mass. The IACUC approval number 04-0624-2 for this study was obtained from Biomodels IACUC.

Animals

Male LVG Syrian Golden Hamsters (Charles River Laboratories), aged 5 to 6 weeks, with average body weight of 84.1 g at study commencement, were used. Animals were individually numbered using an ear punch and housed in small groups of approximately 8 animals per cage. Animals were acclimatized prior to study commencement. During this period of 2 days, the animals were observed daily in order to reject animals that presented in poor condition.

Housing

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records were retained.

Diet

Animals were fed with a Purina Labdiet® 5061 rodent diet and water was provided ad libitum. Animal randomization and allocations.

Animals were randomly and prospectively divided into eight (8) treatment groups prior to irradiation. Each animal was identified by an ear punch corresponding to an individual number. For more consistent identification, ear punch numbering was used rather than tagging, since tags may become dislodged during the course of the study. A cage card was used to identify each cage and was marked with the study number, treatment group number and animal numbers.

Dosing and Drug Application

Dosing solutions were made immediately prior to use. Aseptic technique was used for all preparation procedures. A 26-mM sodium bicarbonate buffer solution was prepared as the vehicle. The resultant pH was approximately 8.1 to 8.3.

Mucositis Induction

Mucositis was induced using a standardized acute radiation protocol. A single dose of radiation (40 Gy/dose) was administered to all animals on day 0. Radiation was generated with a 250 kilovolt potential (15-ma) source at a focal distance of 50 cm, hardened with a 0.35 mm Cu filtration system. Irradiation targeted the left buccal pouch mucosa at a rate of 3.2 Gy/minute. Prior to irradiation, animals were anesthetized with an intra-peritoneal injection of Ketamine (160 mg/kg) and Xylazine (8 mg/kg). The left buccal pouch was everted, fixed and isolated using a lead shield.

Mucositis Scoring

The mucositis score, weight change and survival were measured throughout the study as described above. For the evaluation of mucositis, the animals were anesthetized with isoflurane and the left pouch everted. Mucositis was scored visually by comparison to a validated photographic scale (FIG. 2), ranging from 0 for normal, to 5 for severe ulceration (clinical scoring). In descriptive terms, this scale is defined as follows:

A score of 1-2 is considered to represent a mild stage of the disease, whereas a score of 3-5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above described scale (blinded scoring).

Results and Discussion

Survival

Five deaths occurred during this study. Two animals, hamsters 8 and 23, in the vehicle control group and the group treated with M40403 at 30 mg/kg twice a day from day −1 to day 15 died on day 0 from apparent anesthesia overdoses. In addition, two animals (hamsters 45 and 46) died in the group treated with M40403 at 30 mg/kg twice daily from day −1 to day 3. Hamster 45 died during radiation and hamster 46 was found dead the following morning. Both deaths appeared to be the result of anesthesia overdose, in the case of hamster 46 the response was delayed. The occurrence of anesthesia deaths in this model is anticipated in the experimental design. Hamster 19, in the group treated ip with M40403 at 30 mg/kg twice a day from day −1 to day 15 died on day 12. This death resulted after an extended period of failure to gain weight and may reflect toxicity of this dosing regimen as all animals in this group showed lack of weight gain (see FIGS. 3 and 4 below).

Figure 3:
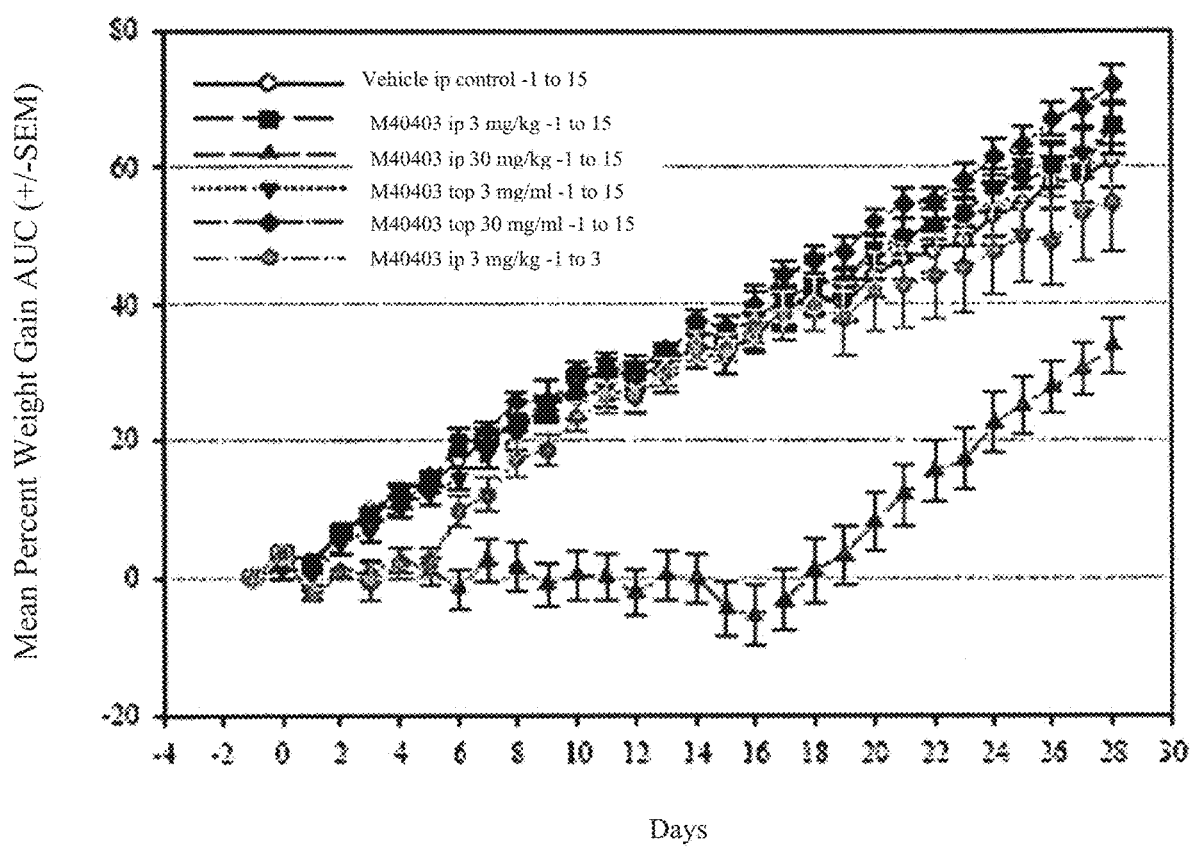
FIG. 3 illustrates the percent daily weight change for the groups treated with intraperitoneal (ip) injection of M40403 (i.e. groups 1, 2, 3, and 6), including the control group, and for the groups treated topically with M40403 (i.e. groups 4 and 5).
Figure 4:
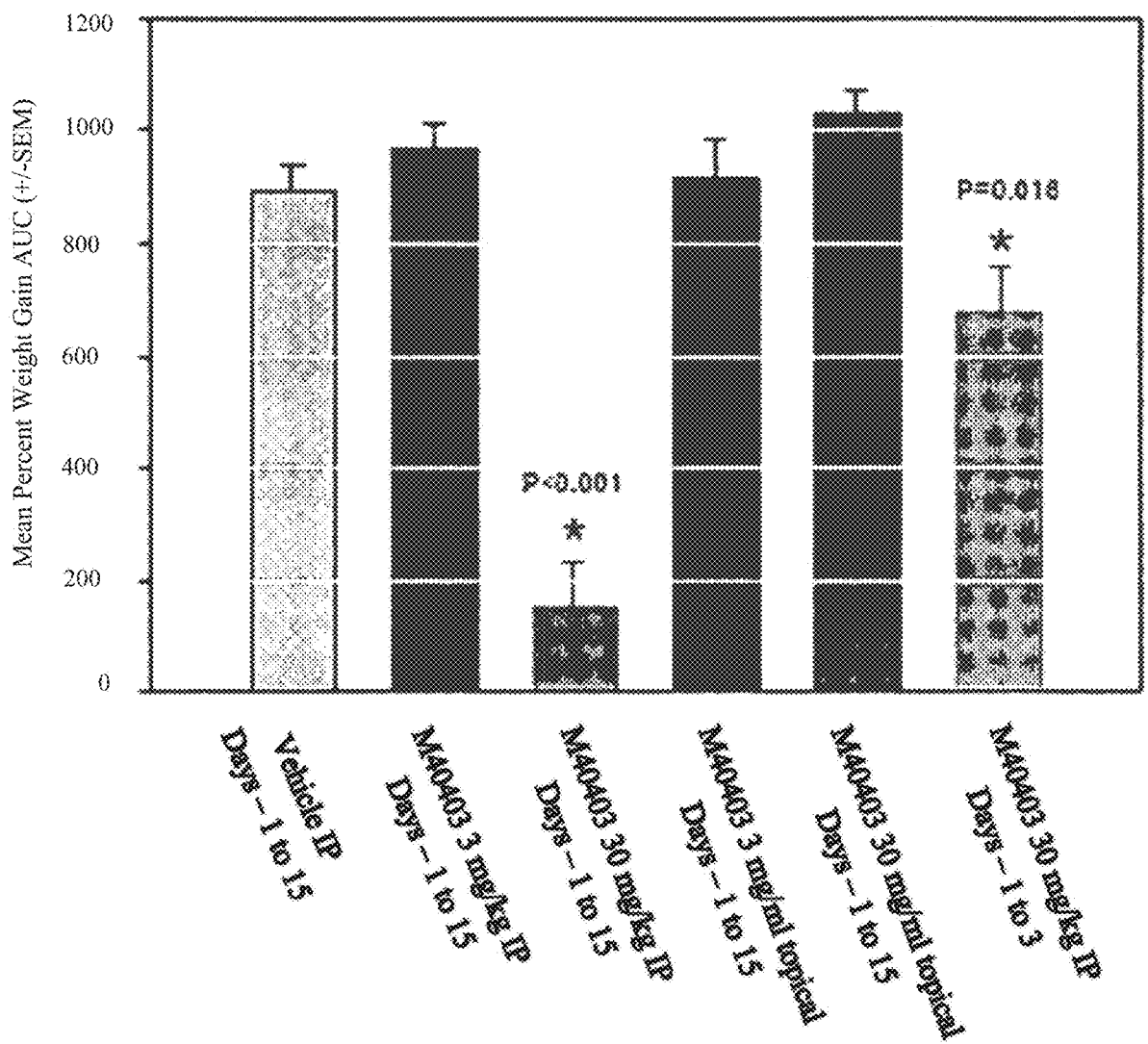
FIG. 4 illustrates the mean percent weight gain for the groups treated ip with M40403 (i.e. groups 1, 2, 3, and 6), including the control group, and for the groups treated topically with M40403 (i.e. groups 4 and 5).

Weight Change (FIGS. 3 and 4).

The percent daily weight change for each group is shown in FIG. 3. The groups treated by ip injection were groups 1, 2, 3 and 6. The control animals (group 1) gained an average of 64.0% of their starting weights by the end of the study. The animals treated ip with M40403 at 3 mg/kg/dose twice daily from day −1 to day 15 (group 2) gained an average of 66.0% of their starting weight during the study. The group treated ip with M40403 at 30 mg/kg/dose twice daily from day −1 to day 15 (group 3) gained an average of 33.9% of their starting weight by day 28. The group treated ip with M40403 at 30 mg/kg/dose twice daily from day 1 to day 3 gained an average of 54.7% of their starting weight during the study. In both groups treated by ip injection with 30 mg/kg M40403, there was a general lack of weight gain during dosing.

In the 2 groups treated topically with M40403 (groups 4 and 5) there was no apparent change in weight gain when compared to the control group. The animals treated topically with M40403 at 3 mg/ml twice daily from day −1 to day 15 gained an average of 65.8% of their starting weight by day 28. The group treated topically with M40403 at 30 mg/ml twice daily from day −1 to day 15 gained an average of 71.9% of their starting weight during the study.

The significance of these differences was evaluated by calculating the mean area under the curve for the percentage weight gain for each animal and comparing the groups using a OneWay ANOVA test. There was a significant difference between the control group and group 3 treated by ip injection with M40403 twice daily (30 mg/kg) on days −1 to 15 ($P<0.001$). There was also a significant difference between the control group and the group treated by ip injection with M40403 twice daily at 30 mg/kg/dose from day −1 to day 3 ($P=0.018$). No other significant differences were seen. The topical treatment groups (groups 4 and 5) showed no significant weight differences when compared with the control group. The AUC data is shown in FIG. 4. Many of the groups with a significant reduction in weight gain are the same groups in which animal deaths were observed.

TABLE 4

| Group Comparison | Day | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| Control v M40403 ip 3 mg/kg day −1 to 15 | 0.099 | 0.630 | 0.950 | 0.286 | 0.983 | 0.630 | 0.436 | 0.571 | 0.754 | 0.325 | 0.516 | 0.070 |
| Control v M40403 ip 30 mg/kg day −1 to 15 | 0.055 | 0.981 | 0.981 | 0.055 | 0.856 | 0.938 | 0.221 | 0.622 | 0.698 | 0.067 | 0.979 | 0.225 |
| Control v M40403 top 3 mg/ml day −1 to 15 | 0.099 | 0.099 | 0.630 | 0.463 | 0.463 | 0.438 | 0.983 | 0.983 | 0.163 | 0.632 | 0.517 | 0.139 |
| Control v M40403 top 30 mg/ml day −1 to 15 | 0.630 | 0.099 | 0.002 | 0.573 | 0.465 | 0.571 | 0.884 | 0.884 | 0.573 | 0.632 | 0.754 | 0.884 |
| Control v M40403 ip 30 mg/kg day −1 to 3 | 0.127 | 0.059 | 0.546 | 0.936 | 0.221 | 0.312 | 0.041 | <0.001 | <0.001 | <0.001 | 0.002 | 0.551 |

Table 4. ACT-02. The significance of group differences observed in daily mucositis scores was determined using the Mann-Whitney rank sum test. This nonparametric statistic is appropriate for the visual mucositis scoring scale. The p values for each calculation are shown.

Figure 6:
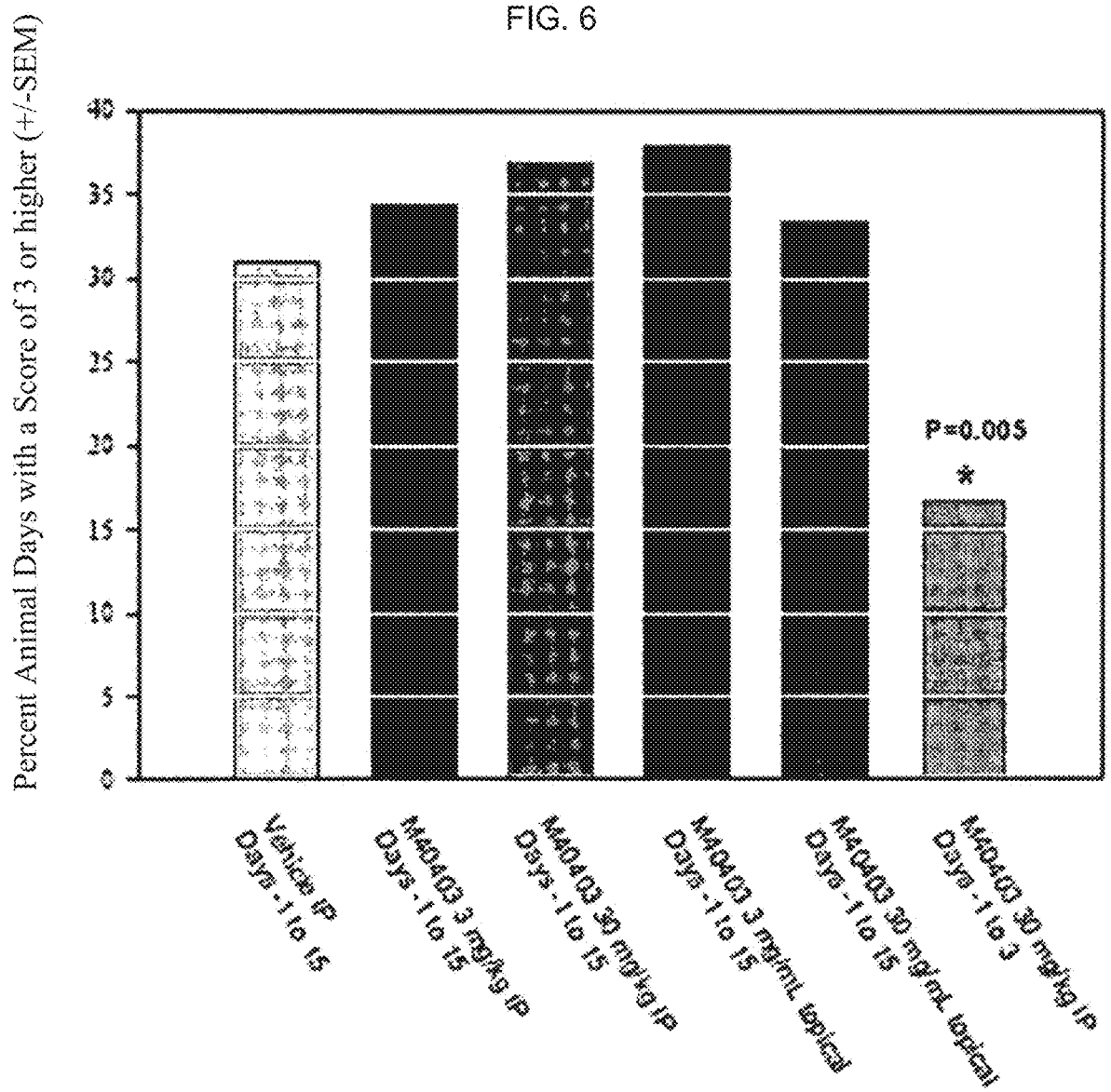
FIG. 6 illustrates the percentage of animal days with a mucositis score of 3 or higher for groups treated ip with M40403 (i.e. groups 1, 2, 3, and 6), including the control group, and for the groups treated topically with M40403 (i.e. groups 4 and 5).

Mucositis (FIGS. 5 & 6, Tables 3 & 4)

Mean daily mucositis scores for each group are shown in FIG. 5. The groups treated by ip injection were groups 1, 2, 3 and 6. The control animals (group 1) had a peak mean mucositis score of 2.8 which occurred on day 16. The animals treated with M40403 at 3 mg/kg/dose ip twice daily from day −1 to day 15 (group 2) had a peak mucositis score of 2.8 on day 18, and the overall progression of mucositis severity in this group was very similar to that observed in the control group. The group treated with M40403 at 30 mg/kg/dose twice daily from day −1 to day 15 (group 3) had a peak mucositis score of 3.0 on day 18 and had a mucositis progression that was indistinguishable from that observed in groups 1 and 2. The group treated with M40403 at 30 mg/kg/dose ip twice daily from day −1 to day 3 had a peak mucositis score of 3.0 on day 14, but from day 16 to day 28, the mucositis severity in this group decreased much more rapidly than the control group suggesting that this schedule of treatment was efficacious.

In the 2 groups treated topically with M40403 (groups 4 and 5) there was no apparent effect of treatment on the course of mucositis. The animals treated topically with M40403 at 3 mg/ml twice daily from day −1 to day 15 had mucositis scores that closely paralleled those in the control group. The group treated topically with M40403 at 30 mg/ml twice daily from day −1 to day 15 showed a reduction of mucositis severity on day 10. However, from day 12 to the end of the study, the scores in this group were only slightly less than those in the control group.

The significance of the reductions in the mucositis scores seen in the groups treated with M40403 were evaluated by calculating the percentage of animal days with a score of 3 or higher. The results of this analysis are shown in FIG. 6 and Table 3. In the control group, the percentage of animal days with a mucositis score of 3 or higher was 31%. Treatment by ip injection with M40403 at 3 mg/kg/dose twice daily from day −1 to day 15 resulted in a percentage of animal days with a score of 3 or higher of 34%. Treatment by ip injection with M40403 at 30 mg/kg/dose twice daily from day to −1 to day 15 resulted in 37% percent of animal days with a score of 3 or higher. Treatment by ip injection with M40403 at 30 mg/kg twice daily from day −1 to day 3 (group 6) resulted in a decrease in the number of animal days with a score of 3 or higher to 17%.

TABLE 3

| Group | Days >= 3 | Days < 3 | Total Days | % Days >= 3 | Chi Sq v control | P Value |
|---|---|---|---|---|---|---|
| Vehicle ip control day −1 to 15 | 52 | 116 | 168 | 0.31 | — | — |
| M40403 ip 3 mg/kg day −1 to 15 | 66 | 126 | 192 | 0.34 | 0.3440 | 0.563 |
| M40403 ip 30 mg/kg day −1 to 15 | 56 | 96 | 152 | 0.37 | 0.9890 | 0.320 |
| M40403 top 3 mg/ml day −1 to 15 | 73 | 119 | 192 | 0.38 | 1.6760 | 0.196 |
| M40403 top 30 mg/ml day −1 to 15 | 64 | 128 | 192 | 0.33 | 0.136 | 0.712 |
| M40403 ip 30 mg/kg day −1 to 3 | 24 | 120 | 144 | 0.17 | 7.83 | 0.005 |

Table 3. ACT-02. Chi-square analysis of the total number of days the animals in each group spent with a mucositis score of 3 or more. This statistic is a measure of severity of ulceration, a clinically important outcome.

In the animals receiving M40403 topically, there were no apparent reductions of mucositis severity at either dosing level. Topical treatment with M40403 at 3 mg/ml twice daily from day −1 to day 15 resulted in an increase in the number of animal days with a score of 3 or higher to 38%. Topical treatment with M40403 at 30 mg/ml twice daily from days −1 to 15 resulted in 33% of animal days with a score of 3 or higher.

When compared using a chi-squared test, the group treated by ip injection with M40403 at 30 mg/kg/dose twice daily on days −1 to day 3 had the greatest reduction in mucositis and significantly fewer days with a score of 3 or higher (P=0.005). No other study group exhibited a reduction in mucositis severity and no group demonstrated a significant difference in mucositis severity by this analysis.

Further analysis of the mucositis scores was performed by comparing the scores for the M40403 treated groups with the control on each day of scoring using the Mann-Whitney Rank Sum test. The results of this analysis are shown in Table 4. The group treated by ip injection with M40403 at 30 mg/kg/dose twice daily on days −1 to day 3 (group 6) had the greatest reduction in mucositis and significantly lower scores than the control group on days 18 (P=0.041), 20 (P<0.001), 22 (P<0.001), 24 (P<0.001) and 26 (P=0.002). No other study group had more than a single day showing a significant lowering of mucositis severity. Given that group 2 received the same dose of drug for a longer duration, these results suggest that the schedule of dosing M40403 is crucial in establishing an effective treatment for mucositis.

Conclusions

1. Based on observations of mortality and body weight, ip injections of M40403, twice daily, at 30 mg/kg appear to show some toxicity. The longer dosing in group 3 resulted in mortality and significant weight loss. When dosed for the shorter period of day −1 to day 3 (group 6), the weight loss was reversed after the cessation of dosing.

2. Topical dosing of M40403 did not appear to have any effect on either weight or mucositis severity. It appears the topical dosing, in the formulation used here, is an ineffective method of delivery of M40403 in this model.

3. The group treated by ip injection with M40403 at 30 mg/kg/dose twice daily on days 1 to 3 had a statistically significant reduction in the number of animal days with a mucositis score of 3 or higher (P=0.005) and significantly lower mucositis scores than the control group on days 18 (P=0.041), 20 (P<0.001), 22 (P<0.001), 24 (P<0.001) and 26 (P=0.002). This result suggests that M40403 may be an effective agent in the treatment of oral mucositis. Further studies of dose and schedule may be required to optimize the efficacy of M40403.

Example 2—Repeat of Day −1 to 3 of 30 mg/kg IV of Example 1 Study

Acute Radiation Model

The acute radiation model in hamsters, developed by the Principal Investigator, has proven to be an accurate, efficient and cost-effective technique to provide a preliminary evaluation of anti-mucositis compounds (9). The course of mucositis in this model is well defined and results in peak scores approximately 14-16 Days following radiation. The acute model has little systemic toxicity, resulting in few hamster deaths, thus permitting the use of smaller groups (N=7-8) for initial efficacy studies. It has also been used to study specific mechanistic elements in the pathogenesis of mucositis. Molecules that show efficacy in the acute radiation model may be further evaluated in the more complex models of fractionated radiation, chemotherapy, or concomitant therapy.

In this study, an acute radiation dose of 40 Gy on day 0 was administered locally to the cheek pouch. Clinically significant mucositis was observed on days 12 through 28.

Protocol Summary

Seventy-two male Syrian Golden Hamsters were divided randomly into 9 groups of 8 animals and given an acute radiation dose of 40 Gy directed to their left buccal cheek pouch. This was accomplished by anesthetizing the animals and everting the left buccal pouch, while protecting the rest of the animal with a lead shield. Test materials were given topically or by ip injection twice daily as detailed in Table 5. Mucositis was evaluated clinically starting on Day 6, and continued on alternate days until day 28.

TABLE 5

Table 1. ACT-03. Study Design

| Group Number | Number of Animals | Treatment | Treatment Schedule* | Volume (mL) |
|---|---|---|---|---|
| 1 | 8 males | Vehicle, ip, bid | Day −1 to 3 | Adjust per body weigh |
| 2 | 8 males | M40403, ip, QD 30 mg/kg | Day −1 to 3 | Adjust per body weigh |
| 3 | 8 males | M40403, ip, bid 3 mg/kg | Day −1 to 3 | Adjust per body weigh |
| 4 | 8 males | M40403, ip, bid 10 mg/kg | Day −1 to 3 | Adjust per body weigh |
| 5 | 8 males | M40403, ip, bid 30 mg/kg | Day −1 to 3 | Adjust per body weigh |
| 6 | 8 males | M40403, ip, QD 30 mg/kg | Day 0 to 3 | Adjust per body weigh |
| 7 | 8 males | M40403, ip, bid 30 mg/kg | Day 0 to 3 | Adjust per body weigh |
| 8 | 8 males | M40403, ip, bid 30 mg/kg | Day 0 | Adjust per body weigh |
| 9 | 8 males | M40403, ip, bid 30 mg/kg | Day 0 and Day 7 | Adjust per body weigh |

*For BID dosing the first dose on day 0 will be performed 30 minutes prior to radiation. The second dose will be given at least 4 hours after radiation. For QD dosing, the dose will be administered on day 0 at 30 minutes prior to irradiation.

Evaluation

Mucositis Evaluation

The grade of mucositis was scored, beginning on day 6, and for every second day thereafter, through and including day 28 (for scoring scheme, see Table 6 and FIG. 8). The effect on mucositis of each drug treatment compared to ip vehicle-treated controls was assessed according to the following parameters:

The difference in the number of days hamsters in each group have ulcerative (score ≥3) mucositis.

On each evaluation day, the number of animals with a blinded mucositis score of ≥3 in each drug treatment group was compared to the vehicle-treated control group.

Differences were compared on a cumulative basis and statistical significance was determined by chi-square analysis. Efficacy, in this analysis, is defined as a significant reduction in the number of days that a group of animals had ulcerations (scores ≥3) when compared to the control group.

TABLE 6

Table 2 ACT-03: Mucositis Scoring.

| Score: | Description: |
|---|---|
| 0 | Pouch completely healthy. No erythema or vasodilation. |
| 1 | Light to severe erythema and vasodilation. No erosion of mucosa. |
| 2 | Severe erythema and vasodilation. Erosion of superficial aspects of mucosa leaving denuded areas. Decreased stippling of mucosa. |
| 3 | Formation of off-white ulcers in one or more places. Ulcers may have a yellow/gray due to pseudomembrane. Cumulative size of ulcers should equal about ¼ of the pouch. Severe erythema and vasodilation. |
| 4 | Cumulative seize of ulcers should equal about ½ of the pouch. Loss of pliability. Severe erythema and vasodilation. |
| 5 | Virtually all of pouch is ulcerated. Loss of pliability (pouch can only partially be extracted from mouth). |

Rank Sum Differences in Daily Mucositis Scores.

For each evaluation day the scores of the control group were compared to those of the treated groups using nonparametric rank sum analysis. Treatment success was considered as a statistically significant lowering of scores in the treated group on 2 or more days from day 6 to day 28.

Weights and Survival

All animals were weighed daily and their survival recorded, in order to assess possible differences in animal weight among treatment groups as an indication for mucositis severity and/or possible toxicity resulting from the treatments.

Study Design

Figure 7:
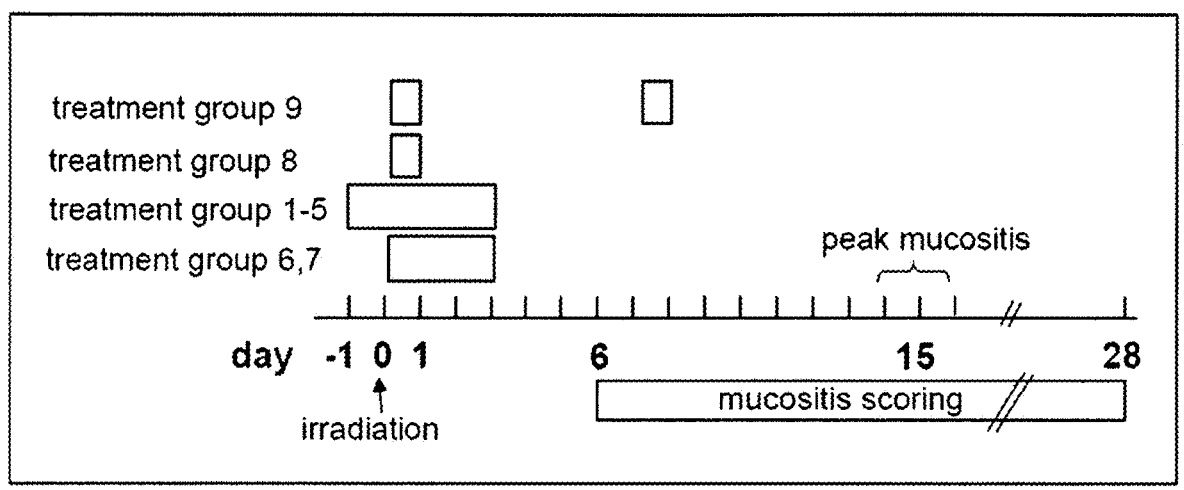
FIG. 7 is a timeline of a study for treatment groups 1-9 to evaluate the effect of M40403, administered by either ip or topical routes. The grade of mucositis was scored, beginning on day 6, and for every second day thereafter, through and including day 28.

All seventy-two (72) male Syrian Golden Hamsters were given an acute radiation dose of 40 Gy directed to their left buccal cheek pouch. This was accomplished by anesthetizing the animals and everting the left buccal pouch, while protecting the rest of the animal with a lead shield. Test materials were given either topically or by ip injection twice daily as detailed in Table 5. Mucositis was evaluated clinically starting on day 6, and continuing on alternate days until day 28. The study timeline is depicted in FIG. 7. Dose levels were determined based on the results of a previous acute toxicity study (data not published), and in the prior mucositis study of Example 1, shown in Table 5.

Material and Methods

Location of Study Performance

The study was performed at Biomodels AAALAC accredited facility in Cambridge Mass. The IACUC approval number 04-0624-2 for this study was obtained from Biomodels IACUC.

Animals

Male LVG Syrian Golden Hamsters (Charles River Laboratories), aged 5 to 6 weeks, with average body weight of 92.7 at study commencement, were used. Animals were individually numbered using an ear punch and housed in small groups of approximately 8 animals per cage. Animals were acclimatized prior to study commencement. During this period of 3 days, the animals were observed daily in order to reject animals that presented in poor condition.

Housing

The study was performed in animal rooms provided with filtered air at a temperature of 70° F.+/−5° F. and 50%+/−20% relative humidity. Animal rooms were set to maintain a minimum of 12 to 15 air changes per hour. The room was on an automatic timer for a light/dark cycle of 12 hours on and 12 hours off with no twilight. Bed-O-Cobs® bedding was used. Bedding was changed a minimum of once per week. Cages, tops, bottles, etc. were washed with a commercial detergent and allowed to air dry. A commercial disinfectant was used to disinfect surfaces and materials introduced into the hood. Floors were swept daily and mopped a minimum of twice weekly with a commercial detergent. Walls and cage racks were sponged a minimum of once per month with a dilute bleach solution. A cage card or label with the appropriate information necessary to identify the study, dose, animal number and treatment group marked all cages. The temperature and relative humidity was recorded during the study, and the records were retained.

Diet

Animals were fed with a Purina Labdiet® 5061 rodent diet and water was provided ad libitum. Animal randomization and allocations.

Animals were randomly and prospectively divided into eight (8) treatment groups prior to irradiation. Each animal was identified by an ear punch corresponding to an individual number. For more consistent identification, ear punch numbering was used rather than tagging, since tags may become dislodged during the course of the study. A cage card was used to identify each cage and was marked with the study number (ACT-03), treatment group number and animal numbers.

Dosing and Drug Application

Dosing solutions were made immediately prior to use. Aseptic technique was used for all preparation procedures. A 26-mM sodium bicarbonate buffer solution was prepared as the vehicle. The resultant pH was approximately 8.1 to 8.3.

Mucositis Induction

Mucositis was induced using a standardized acute radiation protocol. A single dose of radiation (40 Gy/dose) was administered to all animals on day 0. Radiation was generated with a 250 kilovolt potential (15-ma) source at a focal distance of 50 cm, hardened with a 0.35 mm Cu filtration system. Irradiation targeted the left buccal pouch mucosa at a rate of 3.2 Gy/minute. Prior to irradiation, animals were anesthetized with an intra-peritoneal injection of Ketamine (160 mg/kg) and Xylazine (8 mg/kg). The left buccal pouch was everted, fixed and isolated using a lead shield.

Mucositis Scoring

The mucositis score, weight change and survival were measured throughout the study as described above. For the evaluation of mucositis, the animals were anesthetized with isoflurane and the left pouch everted. Mucositis was scored visually by comparison to a validated photographic scale (FIG. 8), ranging from 0 for normal, to 5 for severe ulceration (clinical scoring). In descriptive terms, this scale is defined as follows:

A score of 1-2 is considered to represent a mild stage of the disease, whereas a score of 3-5 is considered to indicate moderate to severe mucositis. Following visual scoring, a photograph was taken of each animal's mucosa using a standardized technique. At the conclusion of the experiment, all films were developed and the photographs randomly numbered. At least two independent trained observers graded the photographs in blinded fashion using the above-described scale (blinded scoring).

Results and Discussion

Survival

Seven deaths occurred during this study, all on the day of radiation (Day 0). Two animals each died in the group treated with M40403 at 30 mg/kg once daily from day −1 to day 3, the group treated with M40403 at 30 mg/kg twice daily from day −1 to day 3 and the group treated with M40403 at 30 mg/kg once daily from day 0 to day 3. One animal died in the group treated with M40403 at 30 mg/kg once daily on day 0 and day 7

Figure 9:
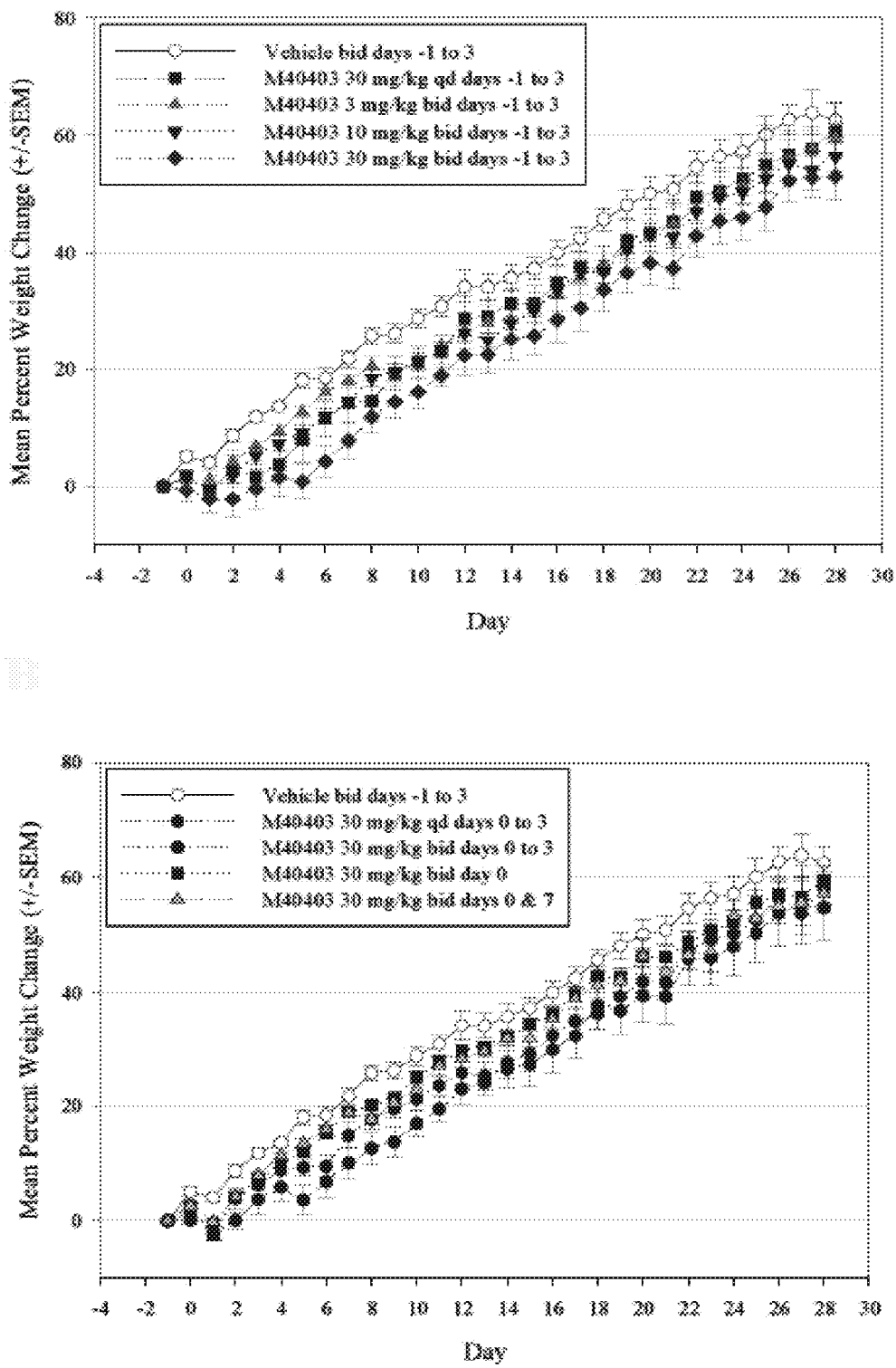
FIG. 9 illustrates the percent daily weight change for the groups treated ip with M40403 (i.e. groups 2-9) and for the control group (i.e. group 1).
Figure 10:
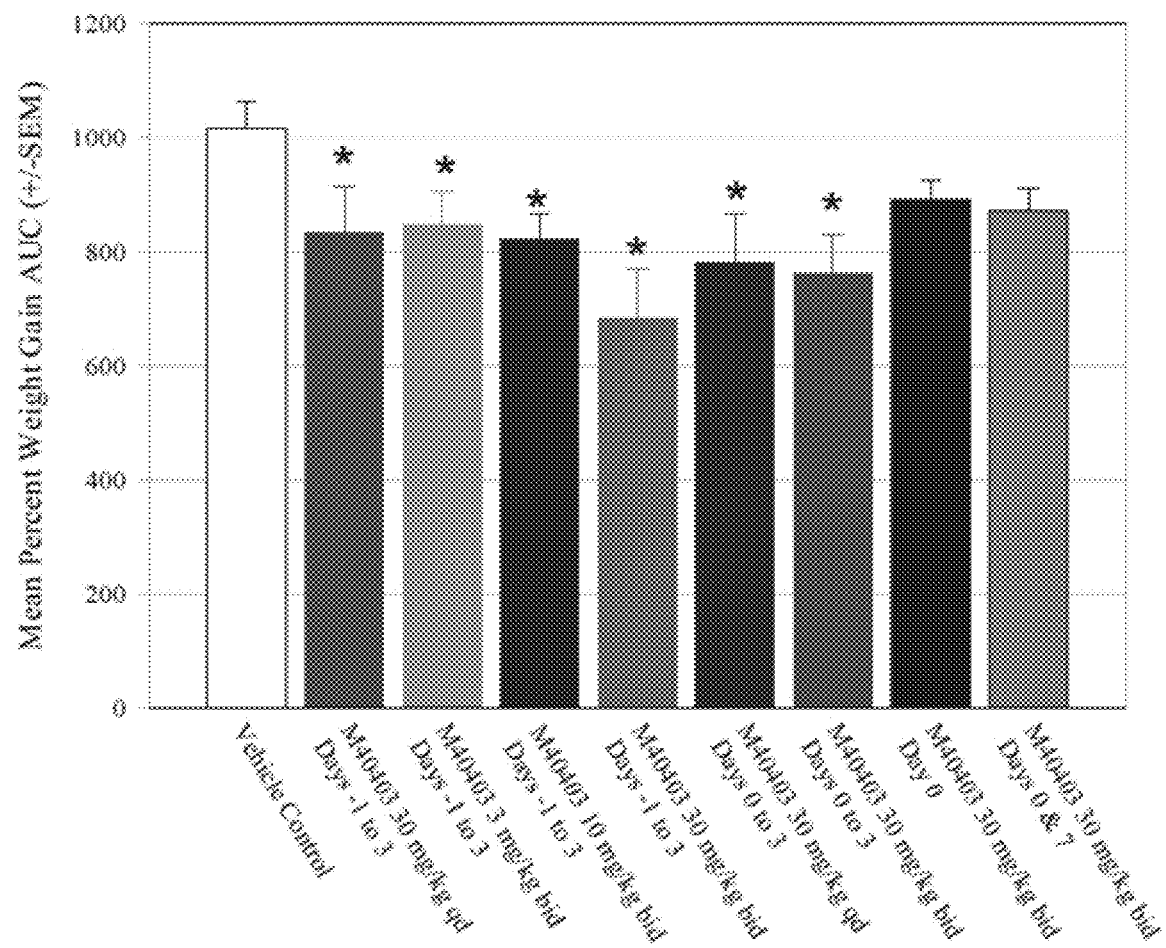
FIG. 10 illustrates the mean percent weight gain for the groups treated ip with M40403 (i.e. groups 2-9) and for the control group (i.e. group 1).

Weight Change (FIGS. 9 and 10).

The percent daily weight change for each group is shown in FIG. 9. The control animals (group 1) gained an average of 62.5% of their starting weights by the end of the study. The animals treated ip with M40403 at 30 mg/kg/dose once daily from day −1 to day 3 (group 2) gained an average of 60.7% of their starting weight during the study. The group treated ip with M40403 at 3 mg/kg/dose twice daily from day −1 to day 3 (group 3) gained an average of 59.3% of their starting weight by day 28. The group treated ip with M40403 at 10 mg/kg/dose twice daily from day −1 to day 3 (group 4) gained an average of 56.2% of their starting weight during the study. The group treated ip with M40403 at 30 mg/kg/dose twice daily from day −1 to day 3 (group 5) gained an average of 52.9% of their starting weight during the study. The group treated ip with M40403 at 30 mg/kg/dose once daily from day 0 to day 3 (group 6) gained an average of 54.8% of their starting weight during the study. The group treated ip with M40403 at 30 mg/kg/dose twice daily from day 0 to day 3 (group 7) gained an average of 58.1% of their starting weight during the study. The group treated ip with M40403 at 30 mg/kg/dose twice daily on day 0 (group 8) gained an average of 59.3% of their starting weight during the study. The group treated ip with M40403 at 30 mg/kg/dose twice daily on day 0 and on day 7 (group 9) gained an average of 57.3% of their starting weight during the study.

The significance of these differences was evaluated by calculating the mean area under the curve for the percentage weight gain for each animal and comparing the groups using a One-Way ANOVA test. There were significant differences between the vehicle control group and the group treated with M40403 at 30 mg/kg/dose once daily from day −1 to day 3 (P=0.039), the group treated with M40403 at 3 mg/kg/dose twice daily from day −1 to day 3 (P=0.040), the group treated with M40403 at 10 mg/kg/dose twice daily from day −1 to day 3 (0.018), the group treated with M40403 at 30 mg/kg/dose twice daily from day −1 to day 3 (P<0.001), the group treated with M40403 at 30 mg/kg/dose once daily from day 0 to day 3 (P=0.009) and the group treated with M40403 at 30 mg/kg/dose twice daily from day 0 to day 3 (P=0.002). The results of this analysis are shown in FIG. 10.

Figure 12:
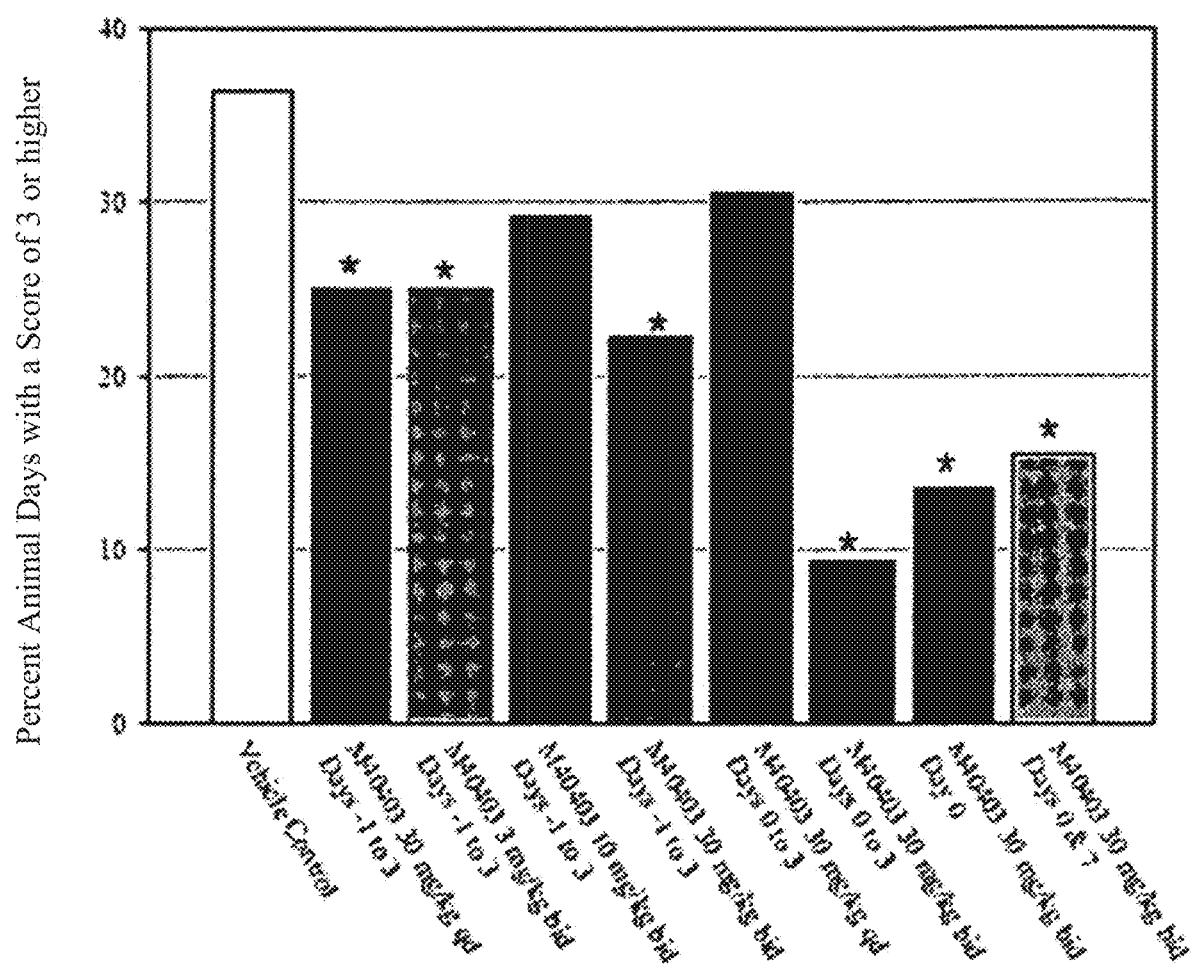
FIG. 12 illustrates the percentage of animal days with a mucositis score of 3 or higher for groups treated ip with M40403 (i.e. groups 2-9) and for the control group (i.e. group 1).

Mucositis (FIGS. 11 & 12, Tables 7 & 8)

Mean daily mucositis scores for each group are shown in FIG. 11. The control animals (group 1) had a peak mean mucositis score of 3.1 on day 16. The animals treated ip with M40403 at 30 mg/kg/dose once daily from day −1 to day 3 (group 2) had a peak mean mucositis score of 2.8 on day 16. The group treated ip with M40403 at 3 mg/kg/dose twice daily from day −1 to day 3 (group 3) had a peak mean mucositis score of 2.9, which occurred on days 16 and 18. The group treated ip with M40403 at 10 mg/kg/dose twice daily from day −1 to day 3 (group 4) had a peak mean mucositis score of 3.0 on day 16. The group treated ip with M40403 at 30 mg/kg/dose twice daily from day −1 to day 3 (group 5) had a peak mean mucositis score of 2.8 on day 16. The group treated ip with M40403 at 30 mg/kg/dose once daily from day 0 to day 3 (group 6) had a peak mean mucositis score of 3.2 on day 16. The group treated ip with M40403 at 30 mg/kg/dose twice daily from day 0 to day 3 (group 7) had a peak mean mucositis score of 2.2 on day 16. The group treated ip with M40403 at 30 mg/kg/dose twice daily on day 0 (group 8) had a peak mean mucositis score of 2.4 on day 14. The group treated ip with M40403 at 30 mg/kg/dose twice daily on day 0 and on day 7 (group 9) had a peak mean mucositis score of 2.4 which occurred on days 16 and 18.

The significance of the reductions in the mucositis scores seen in the groups treated with M40403 were evaluated by calculating the percentage of animal days with a score of 3 or higher. The results of this analysis are shown in FIG. 12 and Table 7. In the control group, the percentage of animal days with a mucositis score of 3 or higher was 36.5%. Treatment by ip injection with M40403 at 30 mg/kg/dose once daily from day −1 to day 3 (group 2) or M40403 at 3 mg/kg/dose twice daily from day −1 to day 3 (group 3) resulted in a percentage of animal days with a score of 3 or higher of 25%. Treatment with M40403 at 10 mg/kg/dose twice daily from day −1 to day 3 (group 4) resulted in a percentage of animal days with a score of 3 or higher of 29.2%. Treatment with M40403 at 30 mg/kg/dose twice daily from day −1 to day 3 (group 5) resulted in a percentage of animal days with a score of 3 or higher of 22.2%. Treatment with M40403 at 30 mg/kg/dose once daily from day 0 to day 3 (group 6) resulted in a percentage of animal days with a score of 3 or higher of 30.6%. Treatment with M40403 at 30 mg/kg/dose twice daily from day 0 to day 3 (group 7) resulted in a percentage of animal days with a score of 3 or higher of 9.4%. Treatment with M40403 at 30 mg/kg/dose twice daily on day 0 (group 8) resulted in a percentage of animal days with a score of 3 or higher of 13.5%. Treatment with M40403 at 30 mg/kg/dose twice daily on day 0 and on day 7 (group 9) resulted in a percentage of animal days with a score of 3 or higher of 15.5%. When compared using a chi-squared test, significant reductions in the number of animal days with a score of 3 or higher were seen in the groups treated with M40403 at 30 mg/kg/dose once daily from day −1 to day 3 (group 2, P=0.034), M40403 at 3 mg/kg/dose twice daily from day −1 to day 3 (group 3, P=0.020), M40403 at 30 mg/kg/dose twice daily from day −1 to day 3 (group 5, P=0.007), M40403 at 30 mg/kg/dose twice daily from day 0 to day 3 (group 7, P<0.001), M40403 at 30 mg/kg/dose twice daily on day 0 (group 8, P<0.001) and M40403 at 30 mg/kg/dose twice daily on day 0 and on day 7 (group 9, P<0.001). This data is shown in FIG. 12 and Table 7.

TABLE 7

| Group | Days >= 3 | Days < 3 | Total Days | % Days >= 3 | Chi Sq v control | P Value |
|---|---|---|---|---|---|---|
| Vehicle ip control bid day −1 to 3 | 70 | 122 | 192 | 36.46% | — | — |
| M40403 ip 30 mg/kg qd day −1 to 3 | 36 | 108 | 144 | 25.00% | 4.4860 | 0.034 |
| M40403 ip 3 mg/kg bid day −1 to 3 | 48 | 144 | 192 | 25.00% | 5.3950 | 0.020 |
| M40403 ip 10 mg/kg bid day −1 to 3 | 56 | 136 | 192 | 29.17% | 1.1996 | 0.158 |
| M40403 ip 30 mg/kg bid day −1 to 3 | 32 | 112 | 144 | 22.22% | 7.229 | 0.007 |
| M40403 ip 30 mg/kg qd day 0 to 3 | 44 | 100 | 144 | 30.56% | 1.029 | 0.310 |
| M40403 ip 30 mg/kg bid day 0 to 3 | 18 | 174 | 192 | 9.38% | 33.3440 | <0.001 |
| M40403 ip 30 mg/kg bid day 0 | 26 | 166 | 192 | 13.54% | 25.681 | <0.001 |
| M40403 ip 30 mg/kg bid day 0 & 7 | 26 | 142 | 168 | 15.48% | 19.113 | <0.001 |

Table 3. ACT-03. Chi-square analysis of the total number of days the animals in each group spent with a mucositis score of three or more. This statistic is a measure of severity of ulceration, a clinically important outcome.

Further analysis of the mucositis scores was performed by comparing the scores for the M40403 treated groups with the control on each day of scoring using the Mann-Whitney Rank Sum test. The results of this analysis are shown in Table 8. The groups treated with M40403 at 30 mg/kg/dose once daily from day −1 to day 3 (group 2), M40403 at 10 mg/kg/dose twice daily from day −1 to day 3 (group 4) and M40403 at 30 mg/kg/dose once daily from day 0 to day 3 (group 6) did not show any days with significant differences relative to controls. The scores for the group treated with M40403 at 3 mg/kg/dose twice daily from day −1 to day 3 (group 3) were significant different from controls on days 14 (P=0.013), 22 (P=0.047) and 28 (P=0.012). The group treated with M40403 at 30 mg/kg/dose twice daily from day −1 to day 3 (group 5) was significant different from controls on days 24 (P=0.048). The group treated with M40403 at 30 mg/kg/dose twice daily from day 0 to day 3 (group 7) had significantly lower scores than the control group on days 14 (P<0.001), 16 (P=0.001), 18 (P=0.007), 20 (P=0.001), 22 (P<0.001), 24 (P=0.006), 26 (P=0.001) and 28 (P=0.012). The group treated with M40403 at 30 mg/kg/dose twice daily on day 0 (group 8) had significantly lower scores than the control group on days 16 (P=0.001), 18 (P=0.033), 20 (P=0.002), 22 (P<0.001), 24 (P=0.010), 26 (P<0.001) and 28 (P=0.009). The group treated with M40403 at 30 mg/kg/dose twice daily on day 0 and on day 7 (group 9) had significantly lower scores than the control group on days 14 (P=0.004), 16 (P=0.047), 20 (P<0.001), 22 (P=0.015) and 26 (P=0.047).

treatment with M40403, or simply accidental death during the anesthesia process

2. The groups treated with M40403 at 30 mg/kg/dose once daily from day −1 to day 3, M40403 at 10 mg/kg/dose twice daily from day −1 to day 3 or M40403 at 30 mg/kg/dose once daily from day 0 to day 3 did not generally show any significant reduction in the course of mucositis relative to controls, although the group treated with M40403 at 30 mg/kg/dose once daily from day −1 to day 3 showed a significant reduction in the number of animals days with a score of 3 or higher (P=0.034).

3. The group treated with M40403 at 3 mg/kg/dose twice daily from day −1 to day 3 had significant lower mucositis scores from controls on days 14 (P=0.013), 22 (P=0.047) and 28 (P=0.012), and had a significant reduction in the number of animals days with a score of 3 or higher (P=0.020).

4. The group treated with M40403 at 30 mg/kg/dose twice daily from day −1 to day 3 had significantly lower scores than the control group on day 24 (P=0.048) and had a significant reduction in the number of animals days with a score of 3 or higher (P=0.007).

5. The group treated with M40403 at 30 mg/kg/dose twice daily from day 0 to day 3 (group 7) had significantly lower scores than the control group on days 14 (P<0.001), 16 (P=0.001), 18 (P=0.007), 20 (P=0.001), 22 (P<0.001), 24 (P=0.006), 26 (P=0.001) and 28 (P=0.012) and had a significant reduction in the number of animals days with a score of 3 or higher (P<0.001).

TABLE 8

| Group Comparison | Day | | | | | | | | | | | |
|---|---|---|---|---|---|---|---|---|---|---|---|---|
| | 6 | 8 | 10 | 12 | 14 | 16 | 18 | 20 | 22 | 24 | 26 | 28 |
| Control v M40403 ip 30 mg/kg qd day −1 to 3 | 0.467 | 0.655 | 0.944 | 0.499 | 0.097 | 0.231 | 0.233 | 0.315 | 0.235 | 0.294 | 0.273 | 0.253 |
| Control v M40403 ip 3 mg/kg bid day −1 to 3 | 0.985 | 0.231 | 0.985 | 0.748 | <u>0.013</u> | 0.297 | 0.865 | 0.459 | <u>0.047</u> | 0.610 | 0.283 | <u>0.012</u> |
| Control v M40403 ip 10 mg/kg bid day −1 to 3 | 0.230 | 0.985 | 0.985 | 0.865 | 0.506 | 0.955 | 0.437 | 0.414 | 0.354 | 0.595 | 0.463 | 0.584 |
| Control v M40403 ip 30 mg/kg bid day −1 to 3 | 0.725 | 0.655 | 0.410 | 0.428 | 0.097 | 0.141 | 0.216 | 0.097 | 0.170 | <u>0.048</u> | 0.053 | 0.066 |
| Control v M40403 ip 30 mg/kg qd day 0 to 3 | 0.961 | 0.944 | 0.798 | 0.834 | 0.361 | 0.870 | 0.592 | 0.981 | 0.437 | 0.388 | 0.362 | 0.798 |
| Control v M40403 ip 30 mg/kg bid day 0 to 3 | 0.776 | 0.555 | 0.472 | 0.940 | <u><0.001</u> | <u>0.001</u> | <u>0.007</u> | <u>0.001</u> | <u><0.001</u> | <u>0.006</u> | <u>0.001</u> | <u>0.012</u> |
| Control v M40403 ip 30 mg/kg bid day 0 | 0.776 | 0.985 | 0.374 | 0.519 | 0.061 | <u>0.001</u> | <u>0.033</u> | <u>0.002</u> | <u><0.001</u> | <u>0.010</u> | <u><0.001</u> | <u>0.009</u> |
| Control v M40403 ip 30 mg/kg bid day 0 & 7 | 0.415 | 0.721 | 0.156 | 0.851 | <u>0.004</u> | <u>0.047</u> | 0.091 | <u><0.001</u> | <u>0.015</u> | 0.163 | <u>0.047</u> | 0.219 |

Table 4. ACT-03. The significance of group differences observed in daily mucositis scores was determined using the Mann-Whitney rank sum test. This nonparametric statistic is appropriate for the visual mucositis scoring scale. The p values for each calculation are shown. Significant improvements are shown underlined.

CONCLUSIONS

1. Based on observations of body weight, ip injections of M40403, appear to show some toxicity. The only groups that did not exhibit some statistically significant reductions in growth rate were those dosed with M40404 on day 0 only or on day 0 and day 7. Some mortality was noted on the day of radiation, but it is not clear whether this was related to 6. The group treated with M40403 at 30 mg/kg/dose twice daily on day 0 (group 8) had significantly lower scores than the control group on days 16 (P=0.001), 18 (P=0.033), 20 (P=0.002), 22 (P<0.001), 24 (P=0.010), 26 (P<0.001) and 28 (P=0.009) and had a significant reduction in the number of animals days with a score of 3 or higher (P<0.001).

7. The group treated with M40403 at 30 mg/kg/dose twice daily on day 0 and on day 7 had significantly lower scores than the control group on days 14 (P=0.004), 16 (P=0.047), 20 (P<0.001), 22 (P=0.015) and 26 (P=0.047) and had a significant reduction in the number of animals days with a score of 3 or higher (P<0.001).

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

REFERENCES CITED

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

1. Knox J J, Puodziunas A L, Feld R. Chemotherapy-induced oral mucositis. Prevention and management. Drugs Aging 2000; 17(4):257-67.
2. Peterson D E. Research advances in oral mucositis. Curr Opin Oncol 1999; 11(4):261-6.
3. Plevova P. Prevention and treatment of chemotherapy- and radiotherapy-induced oral mucositis: a review. Oral Oncol 1999; 35(5):453-70.
4. Sonis S T, Oster G, Fuchs H, Bellm L, Bradford W Z, Edelsberg J, et al. Oral mucositis and the clinical and economic outcomes of hematopoietic stem-cell transplantation. J Clin Oncol 2001; 19(8):2201-5.
5. Eldor A, Fuks Z, Matzner Y, Witte L D, Vlodavsky I. Perturbation of endothelial functions by ionizing irradiation: effects on prostaglandins, chemoattractants and mitogens. Semin Thromb Hemost 1989; 15(2):215-25.
6. Sonis S T, Van Vugt A G, McDonald J, Dotoli E, Schwertschlag U, Szklut P, et al. Mitigating effects of interleukin 11 on consecutive courses of 5-fluorouracil-induced ulcerative mucositis in hamsters. Cytokine 1997; 9(8):605-12.
7. Sonis S T, Van Vugt A G, Brien J P, Muska A D, Bruskin A M, Rose A, et al. Transforming growth factor-beta 3 mediated modulation of cell cycling and attenuation of 5-fluorouracil induced oral mucositis. Oral Oncol 1997; 33(1):47-54.
8. Sonis S T, Peterson R L, Edwards L J, Lucey C A, Wang L, Mason L, et al. Defining mechanisms of action of interleukin-11 on the progression of radiation-induced oral mucositis in hamsters. Oral Oncol 2000; 36(4):373-81.
9. Sonis S T, Tracey C, Shklar G, Jenson J, Florine D. An animal model for mucositis induced by cancer chemotherapy. Oral Surg Oral Med Oral Pathol 1990; 69(4):437-448

APPENDIX 1

Animal Weights

| | | \-1 | 0 | 1 | 2 | 3 | 4 | 5 | 6 | 7 | 8 | 9 | 10 | 11 | 12 | 13 |
|---|---|---|---|---|---|---|---|---|---|---|---|---|---|---|---|---|
| Group | Animal | | | | | | | DAY | | | | | | | | |
| | | | | | | Animal weights from a first study | | | | | | | | | | |
| 1 | 1 | 69 | 92 | 92 | 90 | 101 | 102 | 107 | 110 | 113 | 110 | 118 | 119 | 121 | 110 | 120 |
| 1 | 2 | 94 | 101 | 101 | 108 | 109 | 109 | 116 | 116 | 118 | 122 | 121 | 125 | 126 | 123 | 134 |
| 1 | 3 | 93 | 96 | 96 | 99 | 102 | 105 | 107 | 104 | 112 | 115 | 115 | 118 | 120 | 118 | 118 |
| 1 | 4 | 68 | 92 | 90 | 93 | 96 | 98 | 99 | 101 | 102 | 106 | 106 | 109 | 110 | 132 | 114 |
| 1 | 5 | 98 | 98 | 98 | 102 | 106 | 109 | 113 | 108 | 117 | 123 | 123 | 127 | 129 | 130 | 130 |
| 1 | 6 | 97 | 102 | 101 | 107 | 109 | 111 | 116 | 118 | 121 | 123 | 125 | 127 | 130 | 131 | 130 |
| 1 | 7 | 87 | 95 | 90 | 94 | 97 | 98 | 105 | 104 | 101 | 105 | 105 | 105 | 107 | 110 | 109 |
| 1 | 8 | 91 | 96 | 97 | 100 | 102 | 103 | 105 | 109 | 111 | 115 | 115 | 117 | 119 | 126 | 126 |
| 2 | 9 | 100 | dead | | | | | | | | | | | | | |
| 2 | 10 | 91 | 93 | 90 | 95 | 91 | 93 | 92 | 99 | 101 | 106 | 107 | 107 | 108 | 114 | 115 |
| 2 | 11 | 89 | 89 | 87 | 88 | 83 | 86 | 86 | 91 | 93 | 96 | 99 | 103 | 105 | 110 | 111 |
| 2 | 12 | 98 | 99 | 98 | 109 | 106 | 108 | 116 | 117 | 121 | 103 | 123 | 125 | 126 | 125 | 130 |
| 2 | 13 | 98 | 104 | 102 | 106 | 109 | 110 | 116 | 120 | 123 | 128 | 127 | 129 | 132 | 145 | 139 |
| 2 | 14 | 101 | 102 | 98 | 98 | 97 | 98 | 106 | 110 | 112 | 117 | 119 | 120 | 122 | 128 | 128 |
| 2 | 15 | 76 | 76 | 75 | 74 | 77 | 79 | 81 | 82 | 84 | 86 | 86 | 89 | 89 | 92 | 93 |
| 2 | 16 | 90 | dead | | | | | | | | | | | | | |
| 3 | 17 | 93 | 99 | 98 | 98 | 98 | 103 | 105 | 103 | 106 | 108 | 107 | 111 | 113 | 116 | 118 |
| 3 | 18 | 94 | 95 | 96 | 97 | 98 | 100 | 103 | 107 | 108 | 109 | 107 | 106 | 108 | 115 | 116 |
| 3 | 19 | 96 | 96 | 100 | 101 | 105 | 107 | 109 | 118 | 114 | 115 | 113 | 116 | 119 | 121 | 121 |
| 3 | 20 | 99 | 99 | 102 | 97 | 108 | 105 | 113 | 117 | 120 | 124 | 123 | 125 | 127 | 134 | 134 |
| 3 | 21 | 91 | 93 | 95 | 104 | 99 | 102 | 105 | 107 | 110 | 115 | 113 | 113 | 116 | 120 | 123 |
| 3 | 22 | 105 | 104 | 95 | 110 | 112 | 115 | 120 | 124 | 128 | 132 | 130 | 138 | 138 | 144 | 145 |
| 3 | 23 | 92 | 93 | 93 | 97 | 99 | 102 | 103 | 104 | 106 | 107 | 110 | 112 | 116 | 114 | 117 |
| 3 | 24 | 93 | 91 | 93 | 90 | 98 | 99 | 101 | 105 | 107 | 109 | 107 | 107 | 110 | 101 | 105 |
| 4 | 25 | 96 | 97 | 95 | 93 | 98 | 98 | 102 | 106 | 107 | 110 | 111 | 113 | 115 | 119 | 118 |
| 4 | 26 | 89 | 89 | 88 | 90 | 93 | 92 | 97 | 99 | 101 | 104 | 103 | 102 | 103 | 110 | 108 |
| 4 | 27 | 93 | 98 | 93 | 98 | 102 | 106 | 106 | 107 | 109 | 116 | 118 | 119 | 120 | 123 | 119 |
| 4 | 28 | 99 | 100 | 99 | 98 | 100 | 103 | 106 | 110 | 112 | 115 | 118 | 121 | 122 | 122 | 125 |
| 4 | 29 | 90 | 91 | 90 | 96 | 100 | 102 | 100 | 101 | 104 | 107 | 107 | 108 | 110 | 112 | 111 |
| 4 | 30 | 93 | 98 | 95 | 99 | 102 | 103 | 106 | 111 | 111 | 116 | 116 | 119 | 121 | 125 | 122 |
| 4 | 31 | 93 | 94 | 89 | 91 | 95 | 98 | 99 | 103 | 106 | 108 | 109 | 112 | 116 | 116 | 114 |

APPENDIX 1-continued

Animal Weights

| | | | | | | | | | | | | | | | | |
|---|---|---|---|---|---|---|---|---|---|---|---|---|---|---|---|---|
| 4 | 32 | 91 | 92 | 91 | 95 | 98 | 100 | 102 | 102 | 105 | 109 | 111 | 112 | 114 | 114 | 116 |
| 5 | 33 | 74 | dead | | | | | | | | | | | | | |
| 5 | 34 | 86 | 83 | 84 | 83 | 86 | 88 | 87 | 90 | 94 | 97 | 98 | 100 | 102 | 106 | 106 |
| 5 | 35 | 96 | 98 | 96 | 100 | 101 | 102 | 100 | 103 | 108 | 111 | 116 | 115 | 116 | 119 | 118 |
| 5 | 36 | 90 | 92 | 91 | 94 | 97 | 98 | 95 | 96 | 101 | 104 | 105 | 107 | 109 | 114 | 113 |
| 5 | 37 | 100 | dead | | | | | | | | | | | | | |
| 5 | 38 | 96 | 101 | 100 | 98 | 101 | 103 | 104 | 108 | 110 | 114 | 117 | 119 | 120 | 128 | 129 |
| 5 | 39 | 87 | 84 | 82 | 79 | 78 | 79 | 81 | 84 | 86 | 91 | 93 | 94 | 99 | 97 | 98 |
| 5 | 40 | 89 | 82 | 79 | 78 | 79 | 82 | 81 | 88 | 87 | 91 | 94 | 98 | 100 | 101 | 102 |
| 6 | 41 | 94 | 92 | 98 | 97 | 99 | 102 | 98 | 98 | 103 | 108 | 109 | 110 | 112 | 116 | 115 |
| 6 | 42 | 94 | 95 | 93 | 98 | 99 | 101 | 104 | 103 | 109 | 111 | 113 | 114 | 116 | 119 | 119 |
| 6 | 43 | 101 | 101 | 101 | 107 | 109 | 110 | 115 | 117 | 122 | 126 | 127 | 129 | 130 | 134 | 134 |
| 6 | 44 | 90 | dead | | | | | | | | | | | | | |
| 6 | 45 | 89 | 88 | 88 | 90 | 91 | 96 | 94 | 92 | 95 | 99 | 102 | 102 | 105 | 105 | 102 |
| 6 | 46 | 93 | 94 | 92 | 103 | 102 | 102 | 102 | 104 | 108 | 110 | 112 | 114 | 116 | 119 | 119 |
| 6 | 47 | 99 | 101 | 98 | 97 | 108 | 109 | 111 | 111 | 119 | 118 | 119 | 123 | 126 | 125 | 126 |
| 6 | 48 | 91 | dead | | | | | | | | | | | | | |
| 7 | 49 | 91 | 94 | 91 | 95 | 101 | 104 | 98 | 102 | 106 | 107 | 108 | 113 | 115 | 119 | 120 |
| 7 | 50 | 93 | 95 | 92 | 91 | 93 | 93 | 98 | 104 | 103 | 105 | 106 | 109 | 111 | 115 | 116 |
| 7 | 51 | 90 | 87 | 86 | 87 | 97 | 98 | 95 | 96 | 99 | 101 | 103 | 107 | 108 | 113 | 113 |
| 7 | 52 | 95 | 99 | 95 | 99 | 102 | 104 | 107 | 108 | 113 | 115 | 114 | 113 | 115 | 120 | 120 |
| 7 | 53 | 92 | 93 | 88 | 89 | 91 | 93 | 90 | 93 | 97 | 99 | 101 | 102 | 106 | 109 | 108 |
| 7 | 54 | 98 | 101 | 98 | 102 | 105 | 108 | 101 | 108 | 110 | 112 | 113 | 116 | 119 | 121 | 122 |
| 7 | 55 | 91 | 93 | 90 | 93 | 99 | 101 | 98 | 101 | 104 | 108 | 109 | 111 | 113 | 117 | 118 |
| 7 | 56 | 88 | 87 | 81 | 83 | 78 | 81 | 78 | 80 | 82 | 85 | 86 | 92 | 95 | 94 | 99 |
| 8 | 57 | 94 | 97 | 93 | 99 | 102 | 105 | 105 | 108 | 112 | 113 | 114 | 117 | 119 | 120 | 121 |
| 8 | 58 | 88 | 90 | 84 | 89 | 93 | 95 | 98 | 104 | 105 | 106 | 107 | 111 | 114 | 116 | 118 |
| 8 | 59 | 88 | 92 | 84 | 91 | 93 | 97 | 97 | 100 | 102 | 105 | 103 | 105 | 108 | 110 | 112 |
| 8 | 60 | 86 | 89 | 86 | 96 | 95 | 96 | 99 | 100 | 105 | 106 | 106 | 108 | 111 | 114 | 114 |
| 8 | 61 | 94 | 94 | 91 | 97 | 99 | 103 | 103 | 106 | 110 | 113 | 116 | 117 | 119 | 125 | 124 |
| 8 | 62 | 93 | 94 | 88 | 93 | 98 | 101 | 104 | 108 | 111 | 108 | 112 | 118 | 120 | 122 | 121 |
| 8 | 63 | 91 | 94 | 91 | 96 | 99 | 100 | 103 | 106 | 109 | 110 | 113 | 115 | 117 | 118 | 120 |
| 8 | 64 | 98 | 101 | 96 | 101 | 107 | 107 | 111 | 113 | 117 | 118 | 119 | 125 | 127 | 124 | 124 |
| 9 | 65 | 98 | 101 | 100 | 104 | 108 | 110 | 113 | 115 | 116 | 114 | 117 | 119 | 131 | 124 | 124 |
| 9 | 66 | 94 | 98 | 94 | 98 | 102 | 105 | 107 | 110 | 112 | 113 | 114 | 117 | 118 | 125 | 124 |
| 9 | 67 | 89 | 93 | 90 | 95 | 98 | 101 | 104 | 106 | 108 | 105 | 109 | 112 | 115 | 115 | 116 |
| 9 | 68 | 93 | 96 | 91 | 95 | 100 | 103 | 105 | 104 | 111 | 109 | 112 | 113 | 116 | 117 | 116 |
| 9 | 69 | 98 | 99 | 98 | 102 | 106 | 109 | 110 | 114 | 118 | 119 | 121 | 124 | 129 | 131 | 129 |
| 9 | 70 | 92 | dead | | | | | | | | | | | | | |
| 9 | 71 | 91 | 91 | 89 | 94 | 96 | 100 | 102 | 105 | 106 | 104 | 107 | 110 | 111 | 116 | 120 |
| 9 | 72 | 95 | 96 | 95 | 98 | 101 | 105 | 106 | 109 | 111 | 111 | 114 | 114 | 116 | 116 | 120 |

Animal weights from a second study

| | | | | | | | | | | | | | | | | |
|---|---|---|---|---|---|---|---|---|---|---|---|---|---|---|---|---|
| 1 | 1 | 88 | 92 | 92 | 94 | 96 | 98 | 102 | 103 | 103 | 106 | 108 | 110 | 114 | 113 | 116 |
| 1 | 2 | 89 | 93 | 92 | 96 | 100 | 102 | 103 | 107 | 109 | 110 | 114 | 116 | 119 | 117 | 120 |
| 1 | 3 | 96 | 98 | 98 | 101 | 105 | 108 | 110 | 112 | 115 | 120 | 122 | 125 | 126 | 125 | 123 |
| 1 | 4 | 95 | 97 | 97 | 102 | 103 | 107 | 108 | 111 | 114 | 117 | 118 | 121 | 125 | 123 | 128 |
| 1 | 5 | 88 | 91 | 88 | 91 | 94 | 97 | 98 | 100 | 103 | 105 | 106 | 110 | 112 | 109 | 111 |
| 1 | 6 | 90 | 95 | 93 | 98 | 101 | 104 | 107 | 108 | 111 | 114 | 115 | 122 | 122 | 121 | 124 |
| 1 | 7 | 88 | 89 | 88 | 91 | 94 | 96 | 92 | 99 | 103 | 102 | 104 | 108 | 110 | 108 | 111 |
| 1 | 8 | 92 | AOD | | | | | | | | | | | | | |
| 2 | 9 | 85 | 86 | 86 | 90 | 93 | 96 | 95 | 110 | 104 | 107 | 109 | 111 | 113 | 112 | 113 |
| 2 | 10 | 66 | 89 | 86 | 91 | 94 | 96 | 97 | 100 | 104 | 106 | 107 | 108 | 112 | 112 | 114 |
| 2 | 11 | 68 | 91 | 91 | 94 | 96 | 97 | 98 | 103 | 104 | 105 | 107 | 109 | 112 | 112 | 115 |
| 2 | 12 | 100 | 104 | 102 | 106 | 105 | 112 | 113 | 116 | 121 | 121 | 124 | 129 | 132 | 129 | 132 |
| 2 | 13 | 77 | 81 | 80 | 84 | 87 | 83 | 94 | 95 | 97 | 98 | 101 | 104 | 107 | 108 | 108 |
| 2 | 14 | 92 | 98 | 96 | 101 | 103 | 106 | 108 | 112 | 111 | 115 | 116 | 117 | 118 | 117 | 120 |
| 2 | 15 | 68 | 91 | 69 | 93 | 95 | 95 | 97 | 101 | 102 | 104 | 106 | 109 | 111 | 113 | 115 |
| 2 | 16 | 94 | 97 | 97 | 100 | 102 | 105 | 106 | 113 | 112 | 115 | 116 | 120 | 123 | 123 | 126 |
| 3 | 17 | 90 | 99 | 90 | 96 | 97 | 96 | 96 | 90 | 99 | 90 | 97 | 101 | 100 | 90 | 99 |
| 3 | 18 | 68 | 91 | 86 | 69 | 92 | 94 | 94 | 94 | 98 | 99 | 96 | 97 | 93 | 91 | 93 |
| 3 | 19 | 90 | 93 | 90 | 90 | 92 | 94 | 82 | 80 | 84 | 84 | 85 | 82 | 87 | dead | |
| 3 | 20 | 68 | 91 | 85 | 69 | 82 | 84 | 88 | 79 | 81 | 80 | 76 | 80 | 81 | 80 | 62 |
| 3 | 21 | 101 | 102 | 98 | 100 | 101 | 103 | 101 | 101 | 107 | 108 | 104 | 107 | 108 | 103 | 106 |
| 3 | 22 | 92 | 96 | 87 | 93 | 92 | 95 | 94 | 88 | 91 | 86 | 82 | 83 | 80 | 78 | 80 |
| 3 | 23 | 65 | dead | | | | | | | | | | | | | |
| 3 | 24 | 92 | 95 | 91 | 95 | 97 | 99 | 99 | 100 | 104 | 103 | 100 | 101 | 100 | 98 | 100 |
| 4 | 25 | 86 | 90 | 88 | 91 | 93 | 95 | 99 | 97 | 102 | 105 | 108 | 109 | 105 | 110 | 114 |
| 4 | 26 | 92 | 95 | 93 | 99 | 102 | 103 | 106 | 109 | 112 | 113 | 116 | 121 | 120 | 119 | 123 |
| 4 | 27 | 85 | 87 | 86 | 89 | 90 | 94 | 94 | 98 | 99 | 102 | 119 | 87 | 107 | 105 | 108 |
| 4 | 28 | 94 | 96 | 96 | 101 | 103 | 106 | 107 | 111 | 113 | 115 | 119 | 120 | 127 | 125 | 127 |
| 4 | 29 | 94 | 96 | 96 | 99 | 101 | 104 | 107 | 110 | 112 | 117 | 117 | 123 | 122 | 121 | 123 |
| 4 | 30 | 91 | 94 | 95 | 99 | 102 | 104 | 104 | 100 | 109 | 113 | 115 | 117 | 119 | 118 | 119 |
| 4 | 31 | 93 | 85 | 84 | 38 | 89 | 93 | 94 | 99 | 97 | 98 | 100 | 105 | 105 | 104 | 106 |
| 4 | 32 | 74 | 74 | 75 | 79 | 79 | 82 | 86 | 87 | 92 | 94 | 95 | 103 | 98 | 95 | 98 |
| 5 | 33 | 83 | 83 | 83 | 89 | 89 | 98 | 95 | 98 | 101 | 104 | 105 | 115 | 110 | 108 | 111 |
| 5 | 34 | 79 | 80 | 79 | 83 | 86 | 88 | 90 | 93 | 95 | 102 | 99 | 101 | 104 | 103 | 106 |
| 5 | 35 | 83 | 87 | 85 | 90 | 93 | 95 | 97 | 94 | 101 | 102 | 103 | 105 | 106 | 105 | 109 |

APPENDIX 1-continued

Animal Weights

| 5 | 36 | 84 | 86 | 86 | 91 | 93 | 97 | 100 | 102 | 107 | 111 | 110 | 109 | 115 | 118 | 114 |
|---|---|---|---|---|---|---|---|---|---|---|---|---|---|---|---|---|
| 5 | 37 | 85 | 86 | 85 | 38 | 89 | 91 | 93 | 92 | 99 | 101 | 102 | 106 | 108 | 107 | 111 |
| 5 | 38 | 78 | 79 | 79 | 32 | 84 | 88 | 88 | 97 | 95 | 101 | 99 | 103 | 105 | 102 | 104 |
| 5 | 39 | 85 | 87 | 87 | 90 | 94 | 94 | 99 | 101 | 104 | 106 | 107 | 111 | 112 | 111 | 113 |
| 5 | 40 | 81 | 83 | 82 | 37 | 89 | 90 | 93 | 95 | 97 | 100 | 101 | 107 | 107 | 107 | 109 |
| 6 | 41 | 86 | 87 | 81 | 35 | 93 | 97 | 78 | 82 | 85 | 89 | 91 | 96 | 98 | 100 | 102 |
| 6 | 42 | 91 | 90 | 88 | 93 | 95 | 99 | 102 | 107 | 112 | 114 | 113 | 120 | 122 | 120 | 123 |
| 6 | 43 | 84 | 87 | 84 | 33 | 79 | 79 | 84 | 93 | 89 | 93 | 95 | 98 | 102 | 103 | 107 |
| 6 | 44 | 91 | 94 | 92 | 92 | 93 | 94 | 96 | 101 | 104 | 106 | 103 | 113 | 114 | 114 | 119 |
| 6 | 45 | 78 | dead | | | | | | | | | | | | | |
| 6 | 46 | 86 | 89 | dead | | | | | | | | | | | | |
| 6 | 47 | 89 | 93 | 86 | 91 | 79 | 91 | 92 | 99 | 101 | 105 | 109 | 112 | 114 | 114 | 116 |
| 6 | 48 | 88 | 92 | 87 | 89 | 92 | 86 | 90 | 97 | 100 | 109 | 105 | 111 | 114 | 114 | 118 |

Animal weights from a first study

| Group | Animal | 14 | 15 | 16 | 17 | 18 | 19 | 20 | 21 | 22 | 23 | 24 | 25 | 26 | 27 | 28 |
|---|---|---|---|---|---|---|---|---|---|---|---|---|---|---|---|---|
| 1 | 1 | 120 | 120 | 130 | 132 | 133 | 137 | 138 | 139 | 143 | 140 | 144 | 140 | 149 | 100 | 148 |
| 1 | 2 | 134 | 134 | 138 | 140 | 144 | 148 | 151 | 151 | 168 | 156 | 158 | 160 | 162 | 162 | 164 |
| 1 | 3 | 119 | 123 | 124 | 127 | 130 | 131 | 129 | 133 | 135 | 137 | 139 | 142 | 144 | 142 | 138 |
| 1 | 4 | 115 | 118 | 117 | 120 | 121 | 124 | 126 | 134 | 129 | 132 | 133 | 138 | 138 | 138 | 139 |
| 1 | 5 | 133 | 135 | 138 | 141 | 142 | 148 | 147 | 150 | 153 | 154 | 158 | 165 | 163 | 163 | 159 |
| 1 | 6 | 131 | 131 | 136 | 138 | 141 | 141 | 142 | 143 | 146 | 149 | 149 | 152 | 153 | 171 | 157 |
| 1 | 7 | 111 | 112 | 116 | 116 | 120 | 121 | 122 | 123 | 127 | 128 | 128 | 130 | 134 | 128 | 138 |
| 1 | 8 | 129 | 130 | 130 | 132 | 137 | 137 | 140 | 141 | 145 | 147 | 148 | 150 | 153 | 154 | 154 |
| 2 | 9 | | | | | | | | | | | | | | | |
| 2 | 10 | 116 | 116 | 119 | 121 | 121 | 122 | 124 | 125 | 127 | 129 | 132 | 137 | 133 | 135 | 135 |
| 2 | 11 | 112 | 113 | 118 | 120 | 121 | 124 | 128 | 127 | 133 | 131 | 138 | 160 | 140 | 142 | 143 |
| 2 | 12 | 131 | 133 | 135 | 133 | 142 | 147 | 149 | 152 | 155 | 156 | 158 | 134 | 165 | 164 | 168 |
| 2 | 13 | 140 | 142 | 144 | 147 | 149 | 154 | 150 | 156 | 160 | 162 | 185 | 166 | 186 | 168 | 174 |
| 2 | 14 | 129 | 129 | 132 | 135 | 125 | 138 | 139 | 140 | 144 | 145 | 148 | 150 | 151 | 152 | 155 |
| 2 | 15 | 99 | 95 | 99 | 101 | 101 | 103 | 108 | 106 | 109 | 111 | 109 | 110 | 114 | 115 | 116 |
| 2 | 16 | | | | | | | | | | | | | | | |
| 3 | 17 | 117 | 118 | 119 | 121 | 124 | 124 | 126 | 127 | 129 | 130 | 132 | 133 | 136 | 138 | 139 |
| 3 | 18 | 116 | 118 | 120 | 123 | 125 | 128 | 130 | 132 | 136 | 138 | 140 | 142 | 145 | 149 | 148 |
| 3 | 19 | 122 | 125 | 128 | 131 | 132 | 135 | 137 | 138 | 140 | 143 | 143 | 140 | 147 | 149 | 151 |
| 3 | 20 | 132 | 134 | 138 | 140 | 143 | 145 | 148 | 149 | 152 | 154 | 156 | 160 | 160 | 162 | 165 |
| 3 | 21 | 123 | 125 | 127 | 129 | 132 | 132 | 134 | 136 | 138 | 142 | 143 | 144 | 148 | 147 | 148 |
| 3 | 22 | 149 | 150 | 155 | 158 | 160 | 164 | 166 | 169 | 172 | 174 | 176 | 179 | 181 | 183 | 182 |
| 3 | 23 | 117 | 118 | 117 | 120 | 120 | 126 | 126 | 128 | 130 | 131 | 132 | 136 | 136 | 139 | 140 |
| 3 | 24 | 105 | 110 | 112 | 115 | 117 | 118 | 124 | 126 | 129 | 132 | 134 | 137 | 138 | 138 | 143 |
| 4 | 25 | 121 | 124 | 128 | 130 | 131 | 132 | 133 | 134 | 137 | 139 | 140 | 142 | 145 | 145 | 144 |
| 4 | 26 | 109 | 110 | 112 | 117 | 111 | 117 | 119 | 119 | 121 | 128 | 125 | 126 | 127 | 130 | 128 |
| 4 | 27 | 123 | 124 | 128 | 131 | 130 | 135 | 138 | 137 | 143 | 146 | 145 | 146 | 150 | 156 | 152 |
| 4 | 28 | 128 | 129 | 133 | 135 | 137 | 139 | 140 | 140 | 144 | 145 | 148 | 150 | 152 | 151 | 152 |
| 4 | 29 | 117 | 119 | 121 | 124 | 125 | 129 | 131 | 128 | 133 | 134 | 136 | 140 | 141 | 140 | 142 |
| 4 | 30 | 121 | 126 | 131 | 134 | 134 | 136 | 141 | 141 | 145 | 148 | 149 | 152 | 154 | 158 | 157 |
| 4 | 31 | 117 | 120 | 123 | 125 | 128 | 127 | 131 | 130 | 132 | 132 | 134 | 136 | 138 | 130 | 139 |
| 4 | 32 | 118 | 120 | 125 | 126 | 127 | 130 | 133 | 134 | 137 | 138 | 141 | 143 | 145 | 133 | 148 |
| 5 | 33 | | | | | | | | | | | | | | | |
| 5 | 34 | 107 | 108 | 109 | 111 | 120 | 118 | 120 | 120 | 126 | 129 | 128 | 130 | 134 | 134 | 134 |
| 5 | 35 | 120 | 119 | 123 | 125 | 129 | 129 | 130 | 129 | 134 | 137 | 137 | 139 | 140 | 141 | 142 |
| 5 | 36 | 116 | 117 | 119 | 121 | 120 | 125 | 127 | 127 | 131 | 133 | 133 | 135 | 139 | 134 | 140 |
| 5 | 37 | | | | | | | | | | | | | | | |
| 5 | 38 | 134 | 134 | 138 | 140 | 152 | 144 | 148 | 144 | 149 | 152 | 154 | 156 | 159 | 161 | 161 |
| 5 | 39 | 100 | 103 | 106 | 108 | 117 | 113 | 116 | 115 | 121 | 122 | 123 | 124 | 130 | 132 | 130 |
| 5 | 40 | 104 | 103 | 104 | 105 | 116 | 113 | 112 | 111 | 115 | 117 | 118 | 119 | 125 | 128 | 124 |
| 6 | 41 | 114 | 116 | 117 | 119 | 129 | 125 | 127 | 128 | 136 | 134 | 136 | 140 | 142 | 151 | 144 |
| 6 | 42 | 120 | 121 | 124 | 127 | 133 | 132 | 133 | 133 | 141 | 140 | 142 | 143 | 146 | 149 | 150 |
| 6 | 43 | 135 | 138 | 141 | 142 | 150 | 150 | 154 | 155 | 160 | 160 | 164 | 165 | 172 | 172 | 172 |
| 6 | 44 | | | | | | | | | | | | | | | |
| 6 | 45 | 101 | 98 | 100 | 103 | 105 | 104 | 108 | 106 | 111 | 111 | 111 | 113 | 115 | 114 | 115 |
| 6 | 46 | 122 | 123 | 126 | 128 | 132 | 131 | 134 | 132 | 138 | 139 | 141 | 145 | 146 | 159 | 144 |
| 6 | 47 | 130 | 131 | 135 | 137 | 138 | 140 | 143 | 142 | 147 | 150 | 152 | 153 | 156 | 141 | 160 |
| 6 | 48 | | | | | | | | | | | | | | | |
| 7 | 49 | 127 | 130 | 131 | 133 | 135 | 140 | 141 | 142 | 148 | 149 | 150 | 152 | 156 | 156 | 156 |
| 7 | 50 | 118 | 117 | 124 | 127 | 120 | 128 | 129 | 129 | 135 | 137 | 138 | 140 | 143 | 142 | 146 |
| 7 | 51 | 118 | 121 | 118 | 121 | 125 | 127 | 133 | 131 | 137 | 138 | 138 | 140 | 144 | 146 | 145 |
| 7 | 52 | 124 | 122 | 128 | 131 | 132 | 133 | 137 | 136 | 143 | 142 | 143 | 145 | 148 | 140 | 149 |
| 7 | 53 | 110 | 112 | 117 | 120 | 118 | 121 | 124 | 124 | 128 | 129 | 130 | 133 | 135 | 138 | 137 |
| 7 | 54 | 125 | 126 | 129 | 129 | 135 | 137 | 138 | 138 | 142 | 144 | 146 | 147 | 151 | 145 | 152 |
| 7 | 55 | 120 | 123 | 125 | 127 | 130 | 130 | 132 | 133 | 139 | 140 | 142 | 145 | 148 | 146 | 150 |
| 7 | 56 | 100 | 102 | 105 | 108 | 111 | 112 | 113 | 113 | 116 | 121 | 123 | 124 | 127 | 121 | 130 |
| 8 | 57 | 123 | 125 | 128 | 131 | 138 | 132 | 137 | 137 | 139 | 140 | 143 | 143 | 147 | 147 | 148 |
| 8 | 58 | 119 | 120 | 120 | 124 | 128 | 128 | 131 | 131 | 134 | 134 | 135 | 137 | 139 | 135 | 142 |
| 8 | 59 | 111 | 115 | 118 | 121 | 122 | 118 | 122 | 121 | 123 | 126 | 127 | 131 | 129 | 126 | 127 |

APPENDIX 1-continued

| | | | | | | | | Animal Weights | | | | | | | | |
|---|---|---|---|---|---|---|---|---|---|---|---|---|---|---|---|---|
| 8 | 60 | 117 | 118 | 122 | 124 | 125 | 128 | 131 | 131 | 136 | 138 | 139 | 143 | 145 | 146 | 146 |
| 8 | 61 | 126 | 128 | 126 | 130 | 138 | 137 | 139 | 141 | 142 | 144 | 144 | 146 | 151 | 151 | 153 |
| 8 | 62 | 122 | 126 | 128 | 130 | 134 | 133 | 137 | 138 | 138 | 142 | 145 | 147 | 147 | 154 | 153 |
| 8 | 63 | 123 | 125 | 127 | 131 | 129 | 132 | 135 | 135 | 137 | 138 | 139 | 147 | 143 | 145 | 146 |
| 8 | 64 | 125 | 126 | 127 | 130 | 131 | 135 | 137 | 135 | 139 | 142 | 142 | 144 | 147 | 142 | 151 |
| 9 | 65 | 127 | 126 | 133 | 137 | 135 | 136 | 138 | 139 | 141 | 142 | 144 | 146 | 149 | 148 | 151 |
| 9 | 66 | 127 | 129 | 130 | 134 | 137 | 139 | 141 | 139 | 143 | 145 | 148 | 150 | 152 | 144 | 152 |
| 9 | 67 | 119 | 118 | 123 | 126 | 125 | 126 | 130 | 130 | 132 | 135 | 136 | 137 | 140 | 128 | 143 |
| 9 | 68 | 120 | 119 | 121 | 124 | 129 | 127 | 130 | 129 | 131 | 122 | 133 | 136 | 134 | 122 | 136 |
| 9 | 69 | 133 | 134 | 138 | 141 | 142 | 146 | 152 | 149 | 151 | 153 | 155 | 159 | 162 | 165 | 166 |
| 9 | 70 | | | | | | | | | | | | | | | |
| 9 | 71 | 122 | 122 | 125 | 128 | 128 | 131 | 143 | 134 | 137 | 139 | 139 | 141 | 145 | 142 | 147 |
| 9 | 72 | 120 | 120 | 121 | 124 | 133 | 128 | 129 | 125 | 129 | 132 | 154 | 137 | 138 | 138 | 140 |
| | | | | | | Animal weights from a second study | | | | | | | | | | |
| 1 | 1 | 115 | 115 | 117 | 119 | 119 | 114 | 115 | 116 | 117 | 118 | 121 | 122 | 123 | 124 | 127 |
| 1 | 2 | 124 | 124 | 125 | 129 | 131 | 131 | 135 | 136 | 136 | 138 | 140 | 141 | 147 | 149 | 148 |
| 1 | 3 | 131 | 132 | 137 | 142 | 145 | 144 | 148 | 152 | 153 | 155 | 159 | 161 | 161 | 163 | 169 |
| 1 | 4 | 124 | 124 | 124 | 129 | 130 | 131 | 134 | 138 | 139 | 140 | 143 | 147 | 145 | 149 | 152 |
| 1 | 5 | 111 | 112 | 113 | 117 | 119 | 119 | 123 | 127 | 128 | 131 | 132 | 133 | 136 | 136 | |
| 1 | 6 | 127 | 125 | 124 | 128 | 130 | 130 | 134 | 136 | 139 | 141 | 128 | 147 | 148 | 149 | 153 |
| 1 | 7 | 113 | 112 | 114 | 116 | 117 | 118 | 123 | 123 | 124 | 125 | 145 | 128 | 139 | 133 | 134 |
| 1 | 8 | | | | | | | | | | | | | | | |
| 2 | 9 | 116 | 115 | 121 | 123 | 125 | 127 | 133 | 135 | 138 | 139 | 142 | 144 | 146 | 149 | 152 |
| 2 | 10 | 118 | 117 | 118 | 121 | 123 | 125 | 129 | 130 | 132 | 135 | 139 | 142 | 143 | 147 | 148 |
| 2 | 11 | 119 | 116 | 117 | 119 | 120 | 121 | 125 | 126 | 128 | 129 | 131 | 134 | 134 | 138 | 139 |
| 2 | 12 | 134 | 135 | 135 | 138 | 142 | 140 | 145 | 144 | 150 | 150 | 154 | 155 | 158 | 162 | 160 |
| 2 | 13 | 112 | 111 | 113 | 117 | 119 | 117 | 122 | 125 | 124 | 122 | 129 | 130 | 132 | 136 | 136 |
| 2 | 14 | 118 | 120 | 122 | 123 | 127 | 128 | 131 | 134 | 135 | 136 | 140 | 144 | 142 | 144 | 150 |
| 2 | 15 | 118 | 120 | 121 | 123 | 124 | 126 | 129 | 131 | 132 | 135 | 135 | 137 | 138 | 140 | 142 |
| 2 | 16 | 127 | 126 | 128 | 129 | 131 | 131 | 135 | 136 | 136 | 140 | 143 | 145 | 143 | 113 | 151 |
| 3 | 17 | 99 | 97 | 94 | 90 | 102 | 102 | 100 | 110 | 115 | 117 | 121 | 124 | 124 | 127 | 131 |
| 3 | 18 | 91 | 86 | 84 | 84 | 86 | 91 | 95 | 99 | 101 | 104 | 108 | 111 | 112 | 115 | 118 |
| 3 | 19 | | | | | | | | | | | | | | | |
| 3 | 20 | 83 | 78 | 77 | 79 | 81 | 85 | 89 | 93 | 97 | 99 | 103 | 99 | 108 | 110 | 115 |
| 3 | 21 | 103 | 99 | 99 | 98 | 106 | 107 | 112 | 115 | 119 | 117 | 127 | 128 | 129 | 132 | 135 |
| 3 | 22 | 79 | 74 | 72 | 75 | 79 | 81 | 85 | 88 | 91 | 93 | 97 | 106 | 107 | 108 | 109 |
| 3 | 23 | | | | | | | | | | | | | | | |
| 3 | 24 | 102 | 99 | 101 | 105 | 108 | 110 | 114 | 117 | 121 | 123 | 127 | 130 | 132 | 135 | 138 |
| 4 | 25 | 115 | 116 | 119 | 124 | 125 | 123 | 129 | 131 | 133 | 133 | 137 | 138 | 140 | 145 | 146 |
| 4 | 26 | 123 | 124 | 129 | 134 | 134 | 133 | 141 | 144 | 145 | 143 | 150 | 151 | 152 | 156 | 160 |
| 4 | 27 | 110 | 110 | 111 | 114 | 116 | 114 | 118 | 121 | 123 | 124 | 126 | 130 | 131 | 133 | 136 |
| 4 | 28 | 129 | 127 | 129 | 132 | 132 | 135 | 138 | 142 | 143 | 143 | 128 | 148 | 158 | 148 | 154 |
| 4 | 29 | 125 | 125 | 130 | 132 | 135 | 135 | 142 | 142 | 145 | 149 | 151 | 153 | 157 | 160 | 161 |
| 4 | 30 | 122 | 120 | 126 | 127 | 130 | 127 | 134 | 136 | 139 | 139 | 142 | 142 | 144 | 146 | 149 |
| 4 | 31 | 111 | 109 | 112 | 114 | 116 | 117 | 120 | 123 | 124 | 122 | 129 | 130 | 130 | 133 | 135 |
| 4 | 32 | 107 | 104 | 108 | 111 | 112 | 112 | 116 | 119 | 122 | 126 | 125 | 125 | 124 | 126 | 132 |
| 5 | 33 | 112 | 111 | 114 | 118 | 119 | 120 | 124 | 124 | 124 | 128 | 131 | 132 | 138 | 141 | 140 |
| 5 | 34 | 111 | 110 | 114 | 118 | 119 | 121 | 123 | 127 | 126 | 128 | 132 | 133 | 134 | 137 | 139 |
| 5 | 35 | 120 | 113 | 114 | 116 | 116 | 119 | 124 | 126 | 125 | 128 | 130 | 132 | 137 | 134 | 138 |
| 5 | 36 | 120 | 121 | 124 | 127 | 130 | 132 | 135 | 137 | 139 | 144 | 145 | 148 | 150 | 152 | 158 |
| 5 | 37 | 110 | 108 | 111 | 115 | 117 | 116 | 121 | 123 | 124 | 124 | 129 | 129 | 131 | 134 | 136 |
| 5 | 38 | 107 | 108 | 110 | 114 | 117 | 116 | 122 | 125 | 125 | 128 | 131 | 134 | 133 | 137 | 139 |
| 5 | 39 | 113 | 118 | 121 | 125 | 126 | 127 | 130 | 132 | 132 | 134 | 136 | 137 | 146 | 142 | 148 |
| 5 | 40 | 112 | 110 | 113 | 116 | 116 | 118 | 121 | 123 | 124 | 125 | 128 | 128 | 130 | 133 | 135 |
| 6 | 41 | 108 | 107 | 110 | 112 | 116 | 117 | 120 | 121 | 123 | 125 | 128 | 128 | 130 | 136 | 136 |
| 6 | 42 | 118 | 117 | 115 | 108 | 106 | 104 | 104 | 103 | 134 | 104 | 106 | 108 | 108 | 109 | 110 |
| 6 | 43 | 109 | 108 | 112 | 115 | 115 | 116 | 122 | 124 | 124 | 125 | 127 | 130 | 129 | 131 | 134 |
| 6 | 44 | 120 | 120 | 123 | 125 | 127 | 128 | 132 | 133 | 135 | 137 | 137 | 138 | 136 | 139 | 142 |
| 6 | 45 | | | | | | | | | | | | | | | |
| 6 | 46 | | | | | | | | | | | | | | | |
| 6 | 47 | 124 | 124 | 127 | 129 | 133 | 133 | 137 | 137 | 136 | 138 | 141 | 143 | 142 | 150 | 146 |
| 6 | 48 | 122 | 122 | 126 | 129 | 129 | 131 | 135 | 137 | 138 | 139 | 142 | 145 | 143 | 146 | 149 |

APPENDIX 2

Mucositis Scores
Cheek pouch photographs were scored by 2 independent scorers in a blinded manner resulting in 2 scores for each animal at each time point.

ACT-03 Blinded Scores Mucositis scores from a first study

| Group | Animal | 6 | 8 | 10 | 12 | 14 | 16 | 18 | 20 | 22 | 24 | 26 | 28 |
|---|---|---|---|---|---|---|---|---|---|---|---|---|---|
| 1 | 1 | 0 | 0 | 0 | 2 | 3 | 3 | 3 | 3 | 3 | 2 | 2 | 1 |
| 1 | 1 | 0 | 0 | 0 | 1 | 3 | 3 | 3 | 3 | 3 | 2 | 1 | 1 |
| 1 | 2 | 1 | 0 | 1 | 2 | 3 | 3 | 4 | 3 | 3 | 3 | 2 | 2 |
| 1 | 2 | 0 | 0 | 0 | 2 | 3 | 3 | 3 | 3 | 3 | 3 | 2 | 1 |
| 1 | 3 | 1 | 0 | 1 | 2 | 3 | 4 | 3 | 3 | 3 | 2 | 2 | 2 |
| 1 | 3 | 0 | 0 | 0 | 1 | 3 | 4 | 3 | 3 | 3 | 1 | 2 | 1 |
| 1 | 4 | 1 | 0 | 0 | 2 | 3 | 3 | 3 | 4 | 2 | 2 | 2 | 2 |
| 1 | 4 | 0 | 0 | 0 | 1 | 3 | 3 | 3 | 3 | 2 | 2 | 2 | 1 |
| 1 | 5 | 0 | 1 | 0 | 2 | 3 | 3 | 3 | 3 | 3 | 2 | 2 | 2 |
| 1 | 5 | 0 | 0 | 1 | 2 | 3 | 3 | 3 | 3 | 3 | 1 | 1 | 1 |
| 1 | 6 | 0 | 0 | 1 | 2 | 3 | 3 | 4 | 3 | 2 | 2 | 2 | 2 |
| 1 | 6 | 0 | 0 | 1 | 2 | 3 | 3 | 3 | 3 | 2 | 2 | 2 | 1 |
| 1 | 7 | 0 | 0 | 1 | 2 | 3 | 3 | 2 | 2 | 1 | 1 | 1 | 1 |
| 1 | 7 | 0 | 0 | 1 | 2 | 3 | 3 | 1 | 1 | 1 | 1 | 1 | 1 |
| 1 | 8 | 1 | 0 | 1 | 1 | 2 | 3 | 3 | 3 | 3 | 2 | 2 | 2 |
| 1 | 8 | 0 | 0 | 1 | 0 | 2 | 3 | 3 | 3 | 3 | 2 | 2 | 1 |
| 2 | 9 | dead | | | | | | | | | | | |
| 2 | 9 | | | | | | | | | | | | |
| 2 | 10 | 0 | 0 | 1 | 2 | 2 | 3 | 2 | 2 | 1 | 1 | 1 | 1 |
| 2 | 10 | 0 | 0 | 1 | 1 | 2 | 3 | 2 | 2 | 1 | 1 | 1 | 1 |
| 2 | 11 | 0 | 0 | 1 | 2 | 3 | 3 | 3 | 3 | 3 | 2 | 1 | 1 |
| 2 | 11 | 0 | 0 | 0 | 1 | 3 | 3 | 3 | 3 | 3 | 2 | 2 | 2 |
| 2 | 12 | 0 | 0 | 1 | 1 | 3 | 3 | 3 | 3 | 2 | 2 | 2 | 1 |
| 2 | 12 | 0 | 0 | 0 | 1 | 3 | 3 | 3 | 3 | 2 | 1 | 2 | 1 |
| 2 | 13 | 0 | 0 | 1 | 2 | 3 | 3 | 3 | 3 | 3 | 2 | 2 | 1 |
| 2 | 13 | 0 | 1 | 0 | 2 | 3 | 3 | 3 | 3 | 3 | 2 | 2 | 1 |
| 2 | 14 | 0 | 0 | 1 | 2 | 2 | 3 | 3 | 3 | 2 | 2 | 1 | 0 |
| 2 | 14 | 1 | 1 | 0 | 1 | 2 | 3 | 3 | 3 | 2 | 2 | 2 | 1 |
| 2 | 15 | 0 | 0 | 1 | 2 | 2 | 2 | 2 | 2 | 2 | 1 | 1 | 1 |
| 2 | 15 | 0 | 0 | 0 | 1 | 2 | 2 | 2 | 2 | 2 | 1 | 1 | 2 |
| 2 | 16 | dead | | | | | | | | | | | |
| 2 | 16 | | | | | | | | | | | | |
| 3 | 17 | 0 | 0 | 1 | 1 | 1 | 3 | 3 | 3 | 2 | 2 | 1 | 0 |
| 3 | 17 | 1 | 0 | 1 | 1 | 2 | 3 | 3 | 3 | 2 | 2 | 2 | 1 |
| 3 | 18 | 0 | 0 | 1 | 1 | 2 | 3 | 3 | 3 | 3 | 3 | 2 | 0 |
| 3 | 18 | 1 | 1 | 1 | 1 | 2 | 3 | 3 | 3 | 3 | 3 | 2 | 1 |
| 3 | 19 | 0 | 0 | 1 | 2 | 3 | 3 | 3 | 3 | 2 | 2 | 2 | 0 |
| 3 | 19 | 1 | 1 | 0 | 2 | 3 | 3 | 3 | 3 | 2 | 2 | 1 | 2 |
| 3 | 20 | 0 | 0 | 1 | 1 | 2 | 3 | 4 | 3 | 2 | 1 | 2 | 1 |
| 3 | 20 | 0 | 0 | 1 | 2 | 2 | 3 | 3 | 3 | 2 | 1 | 1 | 2 |
| 3 | 21 | 0 | 0 | 0 | 1 | 2 | 2 | 2 | 2 | 2 | 1 | 2 | 0 |
| 3 | 21 | 0 | 0 | 0 | 1 | 2 | 2 | 2 | 2 | 2 | 2 | 2 | 1 |
| 3 | 22 | 0 | 0 | 1 | 2 | 1 | 2 | 2 | 2 | 1 | 1 | 1 | 0 |
| 3 | 22 | 0 | 1 | 0 | 1 | 2 | 2 | 2 | 2 | 2 | 2 | 1 | 1 |
| 3 | 23 | 0 | 0 | 0 | 3 | 3 | 4 | 4 | 3 | 2 | 2 | 2 | 0 |
| 3 | 23 | 0 | 1 | 0 | 3 | 3 | 4 | 4 | 3 | 2 | 2 | 1 | 1 |
| 3 | 24 | 0 | 0 | 1 | 2 | 3 | 3 | 3 | 3 | 2 | 1 | 2 | 0 |
| 3 | 24 | 1 | 1 | 0 | 2 | 3 | 3 | 3 | 3 | 2 | 1 | 1 | 1 |
| 4 | 25 | 0 | 0 | 1 | 2 | 1 | 1 | 1 | 1 | 1 | 1 | 2 | 1 |
| 4 | 25 | 0 | 0 | 0 | 2 | 1 | 1 | 1 | 1 | 2 | 2 | 1 | 2 |
| 4 | 26 | 0 | 0 | 0 | 0 | 3 | 3 | 3 | 3 | 2 | 1 | 2 | 1 |
| 4 | 26 | 0 | 0 | 0 | 0 | 3 | 3 | 3 | 3 | 2 | 2 | 1 | 2 |
| 4 | 27 | 0 | 0 | 1 | 2 | 2 | 3 | 3 | 3 | 3 | 2 | 2 | 0 |
| 4 | 27 | 0 | 1 | 0 | 2 | 2 | 4 | 3 | 3 | 3 | 2 | 2 | 1 |
| 4 | 28 | 0 | 0 | 2 | 2 | 3 | 3 | 3 | 3 | 3 | 2 | 2 | 1 |
| 4 | 28 | 0 | 0 | 2 | 2 | 3 | 3 | 3 | 3 | 3 | 2 | 2 | 2 |
| 4 | 29 | 0 | 0 | 1 | 2 | 3 | 3 | 4 | 3 | 2 | 2 | 2 | 0 |
| 4 | 29 | 0 | 0 | 0 | 1 | 3 | 4 | 3 | 3 | 2 | 2 | 1 | 1 |
| 4 | 30 | 0 | 0 | 1 | 2 | 3 | 3 | 3 | 3 | 2 | 2 | 2 | 0 |
| 4 | 30 | 0 | 0 | 0 | 1 | 3 | 4 | 3 | 3 | 2 | 2 | 2 | 2 |
| 4 | 31 | 0 | 0 | 1 | 2 | 3 | 3 | 2 | 2 | 2 | 2 | 2 | 1 |
| 4 | 31 | 0 | 0 | 0 | 2 | 3 | 3 | 2 | 2 | 2 | 2 | 1 | 2 |
| 4 | 32 | 0 | 0 | 1 | 2 | 3 | 3 | 3 | 3 | 3 | 2 | 2 | 1 |
| 4 | 32 | 0 | 0 | 0 | 2 | 3 | 4 | 3 | 3 | 3 | 2 | 1 | 2 |
| 5 | 33 | dead | | | | | | | | | | | |
| 5 | 33 | | | | | | | | | | | | |
| 5 | 34 | 0 | 0 | 0 | 2 | 3 | 3 | 3 | 2 | 2 | 1 | 1 | 0 |
| 5 | 34 | 0 | 0 | 0 | 2 | 3 | 3 | 3 | 2 | 2 | 2 | 1 | 1 |
| 5 | 35 | 0 | 0 | 1 | 2 | 3 | 3 | 3 | 3 | 2 | 2 | 2 | 1 |
| 5 | 35 | 0 | 0 | 0 | 2 | 3 | 4 | 3 | 3 | 2 | 2 | 1 | 2 |
| 5 | 36 | 0 | 0 | 1 | 2 | 2 | 2 | 2 | 2 | 0 | 1 | 1 | 1 |

APPENDIX 2-continued

Mucositis Scores
Cheek pouch photographs were scored by 2 independent scorers in a blinded manner resulting in 2 scores for each animal at each time point.

| | | | | | | | | | | | | | |
|---|---|---|---|---|---|---|---|---|---|---|---|---|---|
| 5 | 36 | 0 | 0 | 0 | 1 | 2 | 2 | 2 | 2 | 1 | 1 | 0 | 2 |
| 5 | 37 | dead | | | | | | | | | | | |
| 5 | 37 | | | | | | | | | | | | |
| 5 | 38 | 0 | 0 | 0 | 2 | 2 | 2 | 2 | 2 | 2 | 0 | 2 | 0 |
| 5 | 38 | 1 | 0 | 0 | 1 | 2 | 2 | 1 | 2 | 1 | 0 | 1 | 1 |
| 5 | 39 | 0 | 0 | 0 | 1 | 3 | 3 | 3 | 3 | 3 | 1 | 1 | 0 |
| 5 | 39 | 0 | 1 | 0 | 0 | 3 | 3 | 3 | 3 | 3 | 0 | 1 | 1 |
| 5 | 40 | 1 | 0 | 2 | 1 | 2 | 3 | 3 | 3 | 3 | 2 | 2 | 0 |
| 5 | 40 | 0 | 1 | 1 | 1 | 2 | 3 | 3 | 3 | 3 | 2 | 2 | 1 |
| 6 | 41 | 0 | 0 | 1 | 1 | 1 | 3 | 3 | 3 | 3 | 2 | 2 | 0 |
| 6 | 41 | 1 | 0 | 1 | 0 | 3 | 3 | 3 | 3 | 3 | 2 | 2 | 1 |
| 6 | 42 | 0 | 0 | 1 | 2 | 3 | 3 | 3 | 4 | 2 | 2 | 2 | 1 |
| 6 | 42 | 0 | 0 | 1 | 1 | 3 | 3 | 3 | 3 | 2 | 2 | 1 | 2 |
| 6 | 43 | 0 | 0 | 0 | 2 | 3 | 3 | 2 | 2 | 2 | 2 | 2 | 1 |
| 6 | 43 | 1 | 0 | 0 | 2 | 3 | 3 | 2 | 2 | 2 | 1 | 2 | 2 |
| 6 | 44 | dead | | | | | | | | | | | |
| 6 | 44 | | | | | | | | | | | | |
| 6 | 45 | 0 | 0 | 1 | 2 | 2 | 4 | 4 | 4 | 4 | 4 | 3 | 2 |
| 6 | 45 | 1 | 0 | 0 | 2 | 2 | 4 | 4 | 4 | 4 | 4 | 3 | 2 |
| 6 | 46 | 0 | 0 | 0 | 2 | 3 | 3 | 3 | 3 | 2 | 2 | 2 | 0 |
| 6 | 46 | 0 | 0 | 0 | 2 | 3 | 3 | 3 | 3 | 2 | 2 | 2 | 1 |
| 6 | 47 | 0 | 0 | 1 | 2 | 2 | 3 | 2 | 2 | 0 | 2 | 2 | 2 |
| 6 | 47 | 0 | 1 | 0 | 0 | 2 | 3 | 2 | 2 | 1 | 2 | 1 | 1 |
| 6 | 48 | dead | | | | | | | | | | | |
| 6 | 48 | | | | | | | | | | | | |
| 7 | 49 | 0 | 0 | 1 | 2 | 2 | 1 | 1 | 1 | 0 | 1 | 1 | 1 |
| 7 | 49 | 0 | 1 | 0 | 2 | 2 | 1 | 0 | 0 | 1 | 0 | 1 | 1 |
| 7 | 50 | 0 | 0 | 0 | 2 | 2 | 2 | 3 | 1 | 1 | 0 | 0 | 0 |
| 7 | 50 | 1 | 0 | 0 | 2 | 2 | 1 | 3 | 0 | 2 | 1 | 1 | 1 |
| 7 | 51 | 0 | 0 | 1 | 1 | 2 | 3 | 1 | 2 | 1 | 0 | 0 | 0 |
| 7 | 51 | 1 | 0 | 0 | 0 | 2 | 3 | 2 | 1 | 2 | 0 | 1 | 1 |
| 7 | 52 | 0 | 0 | 0 | 2 | 2 | 2 | 2 | 2 | 1 | 0 | 0 | 0 |
| 7 | 52 | 1 | 1 | 0 | 2 | 2 | 2 | 1 | 0 | 2 | 1 | 1 | 1 |
| 7 | 53 | 0 | 0 | 1 | 1 | 2 | 3 | 3 | 3 | 2 | 1 | 1 | 0 |
| 7 | 53 | 0 | 1 | 0 | 0 | 2 | 3 | 3 | 3 | 2 | 2 | 1 | 1 |
| 7 | 54 | 0 | 0 | 2 | 2 | 2 | 3 | 3 | 3 | 2 | 0 | 1 | 0 |
| 7 | 54 | 0 | 0 | 0 | 2 | 2 | 3 | 3 | 3 | 1 | 2 | 1 | 2 |
| 7 | 55 | 0 | 0 | 0 | 2 | 3 | 2 | 2 | 2 | 2 | 1 | 2 | 0 |
| 7 | 55 | 0 | 0 | 0 | 2 | 3 | 2 | 2 | 1 | 2 | 2 | 1 | 2 |
| 7 | 56 | 0 | 0 | 1 | 2 | 2 | 2 | 1 | 1 | 1 | 2 | 2 | 0 |
| 7 | 56 | 0 | 0 | 1 | 1 | 2 | 2 | 1 | 1 | 1 | 2 | 1 | 1 |
| 8 | 57 | 0 | 0 | 0 | 2 | 3 | 3 | 3 | 3 | 1 | 1 | 0 | 1 |
| 8 | 57 | 0 | 1 | 0 | 2 | 3 | 3 | 3 | 3 | 1 | 2 | 0 | 2 |
| 8 | 58 | 1 | 0 | 0 | 2 | 2 | 2 | 2 | 2 | 1 | 1 | 1 | 1 |
| 8 | 58 | 1 | 0 | 0 | 2 | 2 | 2 | 2 | 2 | 1 | 2 | 0 | 1 |
| 8 | 59 | 0 | 0 | 1 | 2 | 1 | 1 | 1 | 1 | 1 | 1 | 2 | 0 |
| 8 | 59 | 1 | 0 | 0 | 2 | 1 | 2 | 1 | 2 | 1 | 1 | 2 | 1 |
| 8 | 60 | 0 | 0 | 1 | 1 | 3 | 3 | 3 | 1 | 1 | 0 | 0 | 0 |
| 8 | 60 | 0 | 0 | 0 | 1 | 3 | 3 | 3 | 2 | 1 | 2 | 0 | 1 |
| 8 | 61 | 0 | 0 | 1 | 2 | 2 | 2 | 3 | 2 | 1 | 1 | 1 | 0 |
| 8 | 61 | 0 | 0 | 0 | 2 | 2 | 2 | 3 | 1 | 1 | 1 | 1 | 1 |
| 8 | 62 | 0 | 0 | 0 | 2 | 3 | 2 | 1 | 2 | 2 | 0 | 1 | 0 |
| 8 | 62 | 0 | 0 | 0 | 1 | 3 | 2 | 2 | 1 | 2 | 2 | 0 | 1 |
| 8 | 63 | 0 | 0 | 1 | 2 | 2 | 2 | 1 | 2 | 2 | 0 | 1 | 0 |
| 8 | 63 | 1 | 0 | 1 | 2 | 2 | 2 | 1 | 1 | 2 | 2 | 0 | 1 |
| 8 | 64 | 0 | 0 | 1 | 2 | 3 | 3 | 3 | 3 | 2 | 0 | 2 | 0 |
| 8 | 64 | 1 | 0 | 0 | 2 | 3 | 3 | 3 | 3 | 2 | 1 | 0 | 1 |
| 9 | 65 | 0 | 0 | 1 | 2 | 2 | 3 | 3 | 2 | 2 | 0 | 2 | 1 |
| 9 | 65 | 1 | 0 | 0 | 2 | 2 | 3 | 3 | 2 | 2 | 1 | 1 | 2 |
| 9 | 66 | 0 | 0 | 0 | 2 | 2 | 2 | 2 | 2 | 0 | 1 | 1 | 0 |
| 9 | 66 | 1 | 0 | 0 | 1 | 1 | 1 | 1 | 1 | 1 | 2 | 0 | 1 |
| 9 | 67 | 0 | 0 | 0 | 2 | 1 | 1 | 2 | 1 | 0 | 0 | 1 | 0 |
| 9 | 67 | 1 | 0 | 0 | 1 | 1 | 1 | 1 | 1 | 1 | 1 | 0 | 1 |
| 9 | 68 | 1 | 1 | 2 | 2 | 2 | 3 | 3 | 2 | 1 | 1 | 2 | 0 |
| 9 | 68 | 1 | 0 | 0 | 1 | 2 | 3 | 3 | 1 | 2 | 2 | 1 | 1 |
| 9 | 69 | 0 | 0 | 0 | 2 | 3 | 3 | 3 | 3 | 3 | 3 | 2 | 1 |
| 9 | 69 | 1 | 1 | 0 | 1 | 3 | 3 | 3 | 3 | 3 | 3 | 1 | 2 |
| 9 | 70 | | | | | | | | | | | | |
| 9 | 70 | | | | | | | | | | | | |
| 9 | 71 | 0 | 0 | 1 | 2 | 2 | 2 | 2 | 2 | 2 | 1 | 2 | 0 |
| 9 | 71 | 0 | 0 | 0 | 2 | 2 | 2 | 2 | 2 | 2 | 2 | 1 | 2 |
| 9 | 72 | 0 | 0 | 0 | 2 | 3 | 4 | 3 | 1 | 2 | 2 | 2 | 1 |
| 9 | 72 | 0 | 0 | 0 | 2 | 3 | 3 | 3 | 2 | 2 | 1 | 1 | 2 |

APPENDIX 2-continued

Mucositis Scores
Cheek pouch photographs were scored by 2 independent scorers in a blinded manner resulting in 2 scores for each animal at each time point.

| ACT-03 Blinded Scores Mucositis scores from a second study | | | | | | | | | | | | | |
|---|---|---|---|---|---|---|---|---|---|---|---|---|
| 1 | 1 | 0 | 1 | 1 | 2 | 2 | 2 | 2 | 2 | 2 | 1 | 0 | 0 |
| 1 | 1 | 0 | 1 | 1 | 2 | 2 | 2 | 2 | 2 | 2 | 1 | 0 | 0 |
| 1 | 2 | 0 | 1 | 1 | 2 | 3 | 3 | 2 | 2 | 2 | 2 | 2 | 1 |
| 1 | 2 | 0 | 1 | 1 | 2 | 3 | 3 | 2 | 2 | 2 | 2 | 2 | 1 |
| 1 | 3 | 0 | 1 | 1 | 2 | 3 | 3 | 3 | 3 | 3 | 2 | 2 | 2 |
| 1 | 3 | 0 | 1 | 1 | 2 | 3 | 3 | 3 | 3 | 3 | 2 | 2 | 2 |
| 1 | 4 | 0 | 1 | 1 | 2 | 3 | 3 | 3 | 3 | 3 | 2 | 2 | 1 |
| 1 | 4 | 0 | 1 | 1 | 2 | 3 | 3 | 3 | 3 | 3 | 2 | 2 | 1 |
| 1 | 5 | 0 | 1 | 2 | 2 | 3 | 3 | 3 | 3 | 3 | 2 | 2 | 1 |
| 1 | 5 | 0 | 1 | 2 | 2 | 3 | 3 | 3 | 3 | 3 | 2 | 2 | 1 |
| 1 | 6 | 0 | 0 | 1 | 2 | 3 | 3 | 3 | 3 | 3 | 3 | 2 | 2 |
| 1 | 6 | 0 | 0 | 1 | 2 | 3 | 3 | 3 | 3 | 3 | 3 | 2 | 2 |
| 1 | 7 | 1 | 1 | 1 | 1 | 2 | 3 | 3 | 3 | 2 | 2 | 2 | 1 |
| 1 | 7 | 1 | 1 | 1 | 1 | 2 | 3 | 3 | 3 | 2 | 2 | 2 | 1 |
| 1 | 8 | | | | | | | | | | | | |
| 1 | 8 | | | | | | | | | | | | |
| 2 | 9 | 0 | 1 | 1 | 2 | 3 | 3 | 3 | 3 | 2 | 2 | 2 | 2 |
| 2 | 9 | 0 | 1 | 1 | 2 | 3 | 3 | 3 | 3 | 2 | 2 | 2 | 2 |
| 2 | 10 | 1 | 0 | 1 | 2 | 3 | 3 | 3 | 3 | 3 | 2 | 2 | 2 |
| 2 | 10 | 1 | 0 | 1 | 2 | 3 | 3 | 3 | 3 | 3 | 2 | 2 | 2 |
| 2 | 11 | 0 | 1 | 1 | 1 | 3 | 3 | 3 | 3 | 3 | 3 | 2 | 2 |
| 2 | 11 | 0 | 1 | 1 | 1 | 3 | 3 | 3 | 3 | 3 | 3 | 2 | 2 |
| 2 | 12 | 1 | 1 | 1 | 2 | 3 | 3 | 3 | 3 | 3 | 3 | 2 | 1 |
| 2 | 12 | 1 | 1 | 1 | 2 | 3 | 3 | 3 | 3 | 3 | 3 | 2 | 1 |
| 2 | 13 | 1 | 1 | 1 | 1 | 3 | 3 | 3 | 2 | 2 | 2 | 3 | 2 |
| 2 | 13 | 0 | 1 | 1 | 1 | 3 | 3 | 3 | 2 | 2 | 2 | 3 | 2 |
| 2 | 14 | 0 | 1 | 2 | 2 | 3 | 3 | 3 | 3 | 2 | 2 | 2 | 1 |
| 2 | 14 | 0 | 1 | 2 | 2 | 3 | 3 | 3 | 3 | 2 | 2 | 2 | 1 |
| 2 | 15 | 1 | 1 | 1 | 1 | 1 | 2 | 2 | 1 | 2 | 2 | 2 | 2 |
| 2 | 15 | 0 | 1 | 1 | 1 | 1 | 2 | 2 | 1 | 2 | 2 | 2 | 2 |
| 2 | 16 | 1 | 0 | 1 | 2 | 2 | 2 | 3 | 3 | 3 | 2 | 1 | 1 |
| 2 | 16 | 1 | 0 | 1 | 2 | 2 | 2 | 3 | 3 | 3 | 2 | 1 | 1 |
| 3 | 17 | 0 | 1 | 1 | 2 | 2 | 3 | 3 | 3 | 3 | 3 | 2 | 2 |
| 3 | 17 | 0 | 1 | 1 | 2 | 2 | 3 | 3 | 3 | 3 | 3 | 2 | 2 |
| 3 | 18 | 1 | 1 | 1 | 2 | 3 | 3 | 3 | 3 | 3 | 3 | 1 | 1 |
| 3 | 18 | 1 | 1 | 1 | 2 | 3 | 3 | 3 | 3 | 3 | 3 | 1 | 1 |
| 3 | 19 | 1 | 1 | 1 | 1 | | | | | | | | |
| 3 | 19 | 1 | 1 | 1 | 1 | | | | | | | | |
| 3 | 20 | 1 | 1 | 1 | 1 | 3 | 3 | 3 | 3 | 3 | 3 | 3 | 2 |
| 3 | 20 | 1 | 1 | 1 | 1 | 3 | 3 | 3 | 3 | 3 | 3 | 3 | 2 |
| 3 | 21 | 0 | 1 | 1 | 1 | 3 | 3 | 3 | 3 | 3 | 3 | 2 | 2 |
| 3 | 21 | 0 | 1 | 1 | 1 | 3 | 3 | 3 | 3 | 3 | 3 | 2 | 2 |
| 3 | 22 | 1 | 1 | 2 | 2 | 3 | 3 | 3 | 3 | 2 | 2 | 2 | 1 |
| 3 | 22 | 1 | 1 | 2 | 2 | 3 | 3 | 3 | 3 | 2 | 2 | 2 | 1 |
| 3 | 23 | | | | | | | | | | | | |
| 3 | 23 | | | | | | | | | | | | |
| 3 | 24 | 0 | 0 | 1 | 1 | 2 | 2 | 3 | 2 | 2 | 1 | 1 | 1 |
| 3 | 24 | 0 | 0 | 1 | 1 | 2 | 2 | 3 | 2 | 2 | 1 | 1 | 1 |

What is claimed is:

1. A method comprising parenterally administering a dose of a pentaaza macrocyclic ring complex to a mammal to lessen the severity of a mucositis affecting the mucosal lining of the gastrointestinal tract, wherein the mammal is afflicted with cancer and the dose of the pentaaza macrocyclic ring complex is administered on the day before or the day of, but prior to or simultaneous with the mammal receiving either or both of (i) a dose of chemotherapy treatment, or (ii) a dose of radiation therapy, the dose of the pentaaza macrocyclic ring complex being therapeutically sufficient, without requiring the administration of any additional doses of the pentaaza macrocyclic ring complex after either or both of the dose of chemotherapy treatment or dose of radiation therapy, to lessen the severity of the mucositis affecting the mucosal lining of the gastrointestinal tract resulting from the delivered chemotherapy and/or radiation dose, and wherein the pentaaza macrocyclic ring complex is a compound represented by the formula:

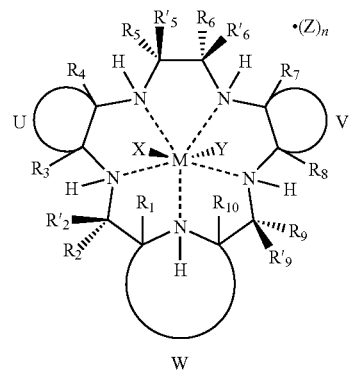

wherein
W is an unsubstituted pyridino moiety;
U and V are trans-cyclohexanyl fused rings;

$R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each independently selected from the group consisting of hydrogen, alkenyl, alkenylcycloalkenyl, alkenylcycloalkyl, alkyl, alkylcycloalkenyl, alkylcycloalkyl, alkynyl, aralkyl, aryl, cycloalkenyl, cycloalkyl, cycloalkylalkyl, cycloalkylcycloalkyl, cycloalkenylalkyl, and heterocyclyl, and aralkyl radicals and radicals attached to the α-carbon or α-amino acids, M is $Mn^{2+}$ or $Mn^{3+}$;

and X, Y and Z are independently selected from the group consisting of halide, oxo, aquo, hydroxo, alcohol, phenol, dioxygen, peroxo, hydroperoxo, alkylperoxo, arylperoxo, ammonia, alkylamino, arylamino, heterocycloalkyl amino, heterocycloaryl amino, amine oxides, hydrazine, alkyl hydrazine, aryl hydrazine, nitric oxide, cyanide, cyanate, thiocyanate, isocyanate, isothiocyanate, alkyl nitrile, aryl nitrile, alkyl isonitrile, aryl isonitrile, nitrate, nitrite, azido, alkyl sulfonic acid, aryl sulfonic acid, alkyl sulfoxide, aryl sulfoxide, alkyl aryl sulfoxide, alkyl sulfenic acid, aryl sulfenic acid, alkyl sulfinic acid, aryl sulfinic acid, alkyl thiol carboxylic acid, aryl thiol carboxylic acid, alkyl thiol thiocarboxylic acid, aryl thiol thiocarboxylic acid, alkyl carboxylic acid, aryl carboxylic acid, urea, alkyl urea, aryl urea, alkyl aryl urea, thiourea, alkyl thiourea, aryl thiourea, alkyl aryl thiourea, sulfate, sulfite, bisulfate, bisulfite, thiosulfate, thiosulfite, hydrosulfite, alkyl phosphine, aryl phosphine, alkyl phosphine oxide, aryl phosphine oxide, alkyl aryl phosphine oxide, alkyl phosphine sulfide, aryl phosphine sulfide, alkyl aryl phosphine sulfide, alkyl phosphonic acid, aryl phosphonic acid, alkyl phosphinic acid, aryl phosphinic acid, alkyl phosphinous acid, aryl phosphinous acid, phosphate, thiophosphate, phosphite, pyrophosphite, triphosphate, hydrogen phosphate, dihydrogen phosphate, alkyl guanidino, aryl guanidino, alkyl aryl guanidino, alkyl carbamate, aryl carbamate, alkyl aryl carbamate, alkyl thiocarbamate, aryl thiocarbamate, alkylaryl thiocarbamate, alkyl dithiocarbamate, aryl dithiocarbamate, alkylaryl dithiocarbamate, bicarbonate, carbonate, perchlorate, chlorate, chlorite, hypochlorite, perbromate, bromate, bromite, hypobromite, tetrahalomanganate, tetrafluoroborate, hexafluoroantimonate, hypophosphite, iodate, periodate, metaborate, tetraaryl borate, tetra alkyl borate, tartrate, salicylate, succinate, citrate, ascorbate, saccharinate, amino acid, hydroxamic acid, thiotosylate, and anions of ion exchange resins, or the corresponding anions thereof;

or X, Y and Z are independently selected from the group consisting of charge-neutralizing anions which are derived from any monodentate or polydentate coordinating ligand and a ligand system and the corresponding anion thereof;

or X, Y and Z are independently attached to one or more of $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$;

and n is an integer from 0 to 3.

2. A method in accordance with claim 1, wherein M is $Mn^{2+}$.

3. A method in accordance with claim 1, wherein $R_1$, $R_2$, $R'_2$, $R_3$, $R_4$, $R_5$, $R'_5$, $R_6$, $R'_6$, $R_7$, $R_8$, $R_9$, $R'_9$, and $R_{10}$ are each hydrogen.

4. A method in accordance with claim 1, wherein the mammal is a human patient.

5. A method in accordance with claim 1, wherein the pentaaza macrocyclic ring complex is administered prior to or simultaneous with the dose of chemotherapy.

6. A method in accordance with claim 1, wherein the pentaaza macrocyclic ring complex is administered to the mammal prior to the mammal receiving the dose of chemotherapy.

7. A method in accordance with claim 5, wherein the pentaaza macrocyclic ring complex is administered to the mammal simultaneously with the mammal receiving the dose of chemotherapy.

8. A method in accordance with claim 1, wherein the pentaaza macrocyclic ring complex is administered prior to or simultaneous with the dose of radiation therapy.

9. A method in accordance with claim 8, wherein the pentaaza macrocyclic ring complex is administered to the mammal prior to the mammal receiving a dose of radiation therapy.

10. A method in accordance with claim 8, wherein the pentaaza macrocyclic ring complex is administered to the mammal simultaneously with the mammal receiving the dose of radiation therapy.

11. A method in accordance with claim 1, wherein an initial dose of the pentaaza macrocyclic ring complex is administered prior to onset of injury to the mucosal lining resulting from the delivered chemotherapy and/or radiation dose.

12. A method in accordance with claim 1, wherein the pentaaza macrocyclic ring complex is administered intravenously or subcutaneously.

13. A method in accordance with claim 12, wherein the pentaaza macrocyclic ring complex is administered intravenously.

14. A method in accordance with claim 1, wherein the mammal is afflicted with a tumor of the head and/or neck.

* * * * *